(12) United States Patent
Freeman et al.

(10) Patent No.: US 7,604,592 B2
(45) Date of Patent: Oct. 20, 2009

(54) METHOD AND APPARATUS FOR A POINT OF CARE DEVICE

(75) Inventors: Dominique M. Freeman, La Honda, CA (US); Dirk Boecker, Palo Alto, CA (US); Don Alden, Sunnyvale, CA (US); Ganapati Mauze, Sunnyvale, CA (US)

(73) Assignee: Pelikan Technologies, Inc., Palo Alto, CA (US)

( * ) Notice: Subject to any disclaimer, the term of this patent is extended or adjusted under 35 U.S.C. 154(b) by 280 days.

(21) Appl. No.: 10/560,272

(22) PCT Filed: Jun. 14, 2004

(86) PCT No.: PCT/US2004/019129

§ 371 (c)(1),
(2), (4) Date: Aug. 16, 2006

(87) PCT Pub. No.: WO2004/112602

PCT Pub. Date: Dec. 29, 2004

(65) Prior Publication Data

US 2006/0276724 A1    Dec. 7, 2006

(51) Int. Cl.
*A61B 5/00* (2006.01)
(52) U.S. Cl. ........................ 600/309; 600/310; 600/345; 600/584
(58) Field of Classification Search ................. 600/309, 600/310, 345, 347, 584; 436/95; 422/68.1, 422/82.05, 82.06, 82.07, 82.08
See application file for complete search history.

(56) References Cited

U.S. PATENT DOCUMENTS

| | | | |
|---|---|---|---|
| 2,801,633 A | 8/1957 | Mauze et al. | |
| 3,358,689 A | 12/1967 | Higgins | 128/329 |
| 3,494,358 A | 2/1970 | Grossenbacher | 128/218 |
| 3,626,929 A | 12/1971 | Sanz | 128/2 R |
| 3,742,954 A | 7/1973 | Strickland | 128/302 |
| 3,832,776 A | 9/1974 | Sawyer | 30/272 |
| 3,953,172 A | 4/1976 | Shapiro | 23/230 |
| 4,224,125 A | 9/1980 | Nakamura | 204/195 B |
| 4,230,118 A | 10/1980 | Holman et al. | 128/314 |
| 4,338,174 A | 7/1982 | Tamura | 204/195 |
| 4,340,669 A | 7/1982 | Bauer | 435/14 |
| 4,353,984 A | 10/1982 | Yamada | 435/14 |
| 4,360,016 A | 11/1982 | Sarrine | 128/763 |
| 4,391,905 A | 7/1983 | Bauer | 435/14 |

(Continued)

FOREIGN PATENT DOCUMENTS

DE    4420232    12/1995

(Continued)

*Primary Examiner*—Eric F Winakur
(74) *Attorney, Agent, or Firm*—Paul Davis; Goodwin Procter LLP

(57) ABSTRACT

A plurality of Point-of-Care (POC) tests on a single cartridge (300) is provided such that sequential or nonsequential tests may be performed in an integrated fashion without changing the test cartridge. Each cartridge can contain a penetrating member sensor (302) combination in a radial disk format, interrogated and read by a single illumination/detection device. Alternatively a series of tests can be measured electrochemically and reported. Only those tests, which are required at the time, the sample is taken need to be reported, though all tests are carried out.

20 Claims, 10 Drawing Sheets

U.S. PATENT DOCUMENTS

| | | | | |
|---|---|---|---|---|
| 4,391,906 A | 7/1983 | Bauer | 435/14 |
| 4,414,975 A | 11/1983 | Ryder | 128/314 |
| 4,420,564 A | 12/1983 | Tsuji | 435/288 |
| 4,426,451 A | 1/1984 | Columbus | 436/518 |
| 4,426,884 A | 1/1984 | Polchaninoff | 73/172 |
| 4,469,110 A | 9/1984 | Slama | 128/770 |
| 4,517,978 A | 5/1985 | Levin | 128/314 |
| 4,539,988 A | 9/1985 | Shirley | 128/314 |
| 4,545,382 A | 10/1985 | Higgins | 128/635 |
| 4,553,541 A | 11/1985 | Burns | 128/314 |
| 4,577,630 A | 3/1986 | Nitzsche | 128/314 |
| 4,580,564 A | 4/1986 | Anderson | 502/8 |
| 4,580,565 A | 4/1986 | Cornell | 128/314 |
| 4,590,411 A | 5/1986 | Kelly | 318/687 |
| 4,595,479 A | 6/1986 | Kimura | 204/294 |
| 4,608,997 A | 9/1986 | Conway | 128/763 |
| 4,615,340 A | 10/1986 | Cronenberg | 128/635 |
| 4,616,649 A | 10/1986 | Burns | 128/314 |
| 4,619,754 A | 10/1986 | Niki | 204/290 |
| 4,622,974 A | 11/1986 | Coleman | 128/634 |
| 4,624,253 A | 11/1986 | Burns | 128/314 |
| 4,637,393 A | 1/1987 | Ray | 128/305 |
| 4,643,189 A | 2/1987 | Mintz | 128/314 |
| 4,648,408 A | 3/1987 | Hutcheson | 128/770 |
| 4,653,511 A | 3/1987 | Goch | 128/763 |
| 4,676,244 A | 6/1987 | Enstrom | 128/314 |
| 4,677,979 A | 7/1987 | Burns | 128/314 |
| 4,711,245 A | 12/1987 | Higgins | 128/635 |
| 4,712,548 A | 12/1987 | Enstrom | 128/314 |
| 4,715,374 A | 12/1987 | Maggio | 128/314 |
| 4,735,203 A | 4/1988 | Ryder | 128/314 |
| 4,758,323 A | 7/1988 | Davis | 204/403 |
| 4,794,926 A | 1/1989 | Munsch et al. | 606/183 |
| 4,814,142 A | 3/1989 | Gleisner | 422/56 |
| 4,814,661 A | 3/1989 | Ratzlaff | 310/328 |
| 4,820,010 A | 4/1989 | Sciefres | 385/43 |
| 4,820,399 A | 4/1989 | Senda | 204/403 |
| 4,824,639 A | 4/1989 | Hildenbrand | 422/56 |
| RE32,922 E | 5/1989 | Levin | 128/314 |
| 4,827,763 A | 5/1989 | Bourland | 73/172 |
| 4,830,959 A | 5/1989 | McNeil | 435/53 |
| 4,836,904 A | 6/1989 | Armstron | 204/294 |
| 4,844,095 A | 7/1989 | Chiodo | 128/314 |
| 4,850,973 A | 7/1989 | Jordan | 604/157 |
| 4,857,274 A | 8/1989 | Simon | 422/72 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,882,013 A | 11/1989 | Turner | 204/1 |
| 4,883,068 A | 11/1989 | Dechow | 128/760 |
| 4,886,499 A | 12/1989 | Cirelli | 604/131 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |
| 4,897,173 A | 1/1990 | Nankai | 204/403 |
| 4,900,424 A | 2/1990 | Birch | 204/409 |
| 4,911,794 A | 3/1990 | Parce | 204/1 T |
| 4,920,977 A | 5/1990 | Haynes | 128/770 |
| 4,945,045 A | 7/1990 | Forrest | 435/25 |
| 4,948,727 A | 8/1990 | Cass | 435/18 |
| 4,952,515 A | 8/1990 | Gleisner | 436/169 |
| 4,953,552 A | 9/1990 | DeMarzo | 128/635 |
| 4,966,671 A | 10/1990 | Nylander | 204/153.14 |
| 4,976,724 A | 12/1990 | Nieto | 606/182 |
| 4,983,178 A | 1/1991 | Schnell | 606/181 |
| 4,990,154 A | 2/1991 | Brown | 606/182 |
| 4,999,582 A | 3/1991 | Parks | 324/438 |
| 5,010,772 A | 4/1991 | Bourland | 73/862.04 |
| 5,010,774 A | 4/1991 | Kikuo | 73/862.04 |
| 5,014,718 A | 5/1991 | Mitchen | 128/771 |
| 5,019,974 A | 5/1991 | Beckers | 364/413.02 |
| 5,026,388 A | 6/1991 | Ingalz | 606/182 |
| 5,029,583 A | 7/1991 | Meserol | |
| 5,047,044 A | 9/1991 | Smith et al. | |
| 5,054,499 A | 10/1991 | Swierczek | 128/770 |
| 5,059,789 A | 10/1991 | Salcudean | 250/206.1 |
| 5,060,174 A | 10/1991 | Gross | 702/139 |
| 5,070,886 A | 12/1991 | Mitchen | 128/771 |
| 5,074,872 A | 12/1991 | Brown | 606/182 |
| 5,089,112 A | 2/1992 | Skotheim | 204/403 |
| 5,092,842 A | 3/1992 | Bechtold | 604/135 |
| 5,100,427 A | 3/1992 | Crossman | 606/182 |
| 5,100,428 A | 3/1992 | Mumford | 606/182 |
| 5,104,380 A | 4/1992 | Holman | 604/117 |
| 5,104,619 A | 4/1992 | Castro | 422/56 |
| 5,108,564 A | 4/1992 | Szuminsky | 204/153.12 |
| 5,108,889 A | 4/1992 | Smith et al. | |
| 5,116,759 A | 5/1992 | Klainer | 435/288 |
| 5,120,420 A | 6/1992 | Nankai | 204/403 |
| 5,122,244 A | 6/1992 | Hoenes | 204/153 |
| 5,126,034 A | 6/1992 | Carter | 204/403 |
| 5,128,015 A | 7/1992 | Szuminsky | 204/403 |
| 5,128,171 A | 7/1992 | Gleisner | 427/2 |
| 5,133,730 A | 7/1992 | Biro | 606/182 |
| 5,139,685 A | 8/1992 | Castro | 210/767 |
| 5,141,868 A | 8/1992 | Shanks | 435/288 |
| 5,156,611 A | 10/1992 | Haynes | 606/181 |
| 5,163,442 A | 11/1992 | Ono | 128/760 |
| 5,170,364 A | 12/1992 | Gross | 702/139 |
| D332,490 S | 1/1993 | Brown et al. | D24/146 |
| 5,178,142 A | 1/1993 | Harjunmaa | 128/633 |
| 5,181,910 A | 1/1993 | Scanlon | 604/67 |
| 5,181,914 A | 1/1993 | Zook | 604/307 |
| 5,183,042 A | 2/1993 | Harjunmaa | 128/633 |
| 5,185,256 A | 2/1993 | Nankai | 435/174 |
| 5,187,100 A | 2/1993 | Matzinger | 436/16 |
| 5,192,415 A | 3/1993 | Yoshioka | 204/403 |
| 5,196,025 A | 3/1993 | Ranalletta | 606/182 |
| 5,201,324 A | 4/1993 | Swierczek | 128/770 |
| 5,205,920 A | 4/1993 | Oyama | 204/403 |
| 5,212,879 A | 5/1993 | Biro | 29/437 |
| 5,216,597 A | 6/1993 | Beckers | 364/413.02 |
| 5,217,480 A | 6/1993 | Haber | 606/182 |
| 5,228,972 A | 7/1993 | Osaka | 204/415 |
| 5,229,282 A | 7/1993 | Yoshioka | 435/177 |
| 5,230,866 A | 7/1993 | Shartle | 422/103 |
| 5,231,993 A | 8/1993 | Haber et al. | 128/770 |
| 5,250,066 A | 10/1993 | Lambert | 606/181 |
| 5,251,126 A | 10/1993 | Kahn | 365/413.11 |
| 5,253,656 A | 10/1993 | Rincoe | 128/782 |
| 5,256,998 A | 10/1993 | Becker | 335/229 |
| 5,264,103 A | 11/1993 | Yoshioka | 204/403 |
| 5,264,105 A | 11/1993 | Gregg | 204/403 |
| 5,264,106 A | 11/1993 | McAleer | 204/403 |
| 5,266,179 A | 11/1993 | Nankai | 204/401 |
| D342,573 S | 12/1993 | Cerola | D24/147 |
| 5,272,087 A | 12/1993 | El Murr | 435/291 |
| 5,277,181 A | 1/1994 | Mendelson | 128/633 |
| 5,282,822 A | 2/1994 | Macors | 606/182 |
| 5,286,362 A | 2/1994 | Hoenes | 204/403 |
| 5,286,364 A | 2/1994 | Yacynych | 204/418 |
| 5,288,636 A | 2/1994 | Pollmann | 435/288 |
| 5,304,192 A | 4/1994 | Crouse | 606/181 |
| 5,304,193 A | 4/1994 | Zhadanov | 606/182 |
| 5,312,590 A | 5/1994 | Gunasingham | 422/56 |
| 5,314,441 A | 5/1994 | Cusack | 606/182 |
| 5,314,442 A | 5/1994 | Morita | 606/182 |
| 5,316,012 A | 5/1994 | Siegal | 128/744 |
| 5,318,583 A | 6/1994 | Rabenau | 606/182 |
| 5,320,607 A | 6/1994 | Ishibashi | 604/115 |
| 5,324,302 A | 6/1994 | Crouse | 606/181 |
| 5,324,303 A | 6/1994 | Strong | 606/181 |
| 5,332,479 A | 7/1994 | Uenoyama | 204/153.12 |
| 5,350,392 A | 9/1994 | Purcell | 606/182 |

| | | | | | | | |
|---|---|---|---|---|---|---|---|
| 5,352,351 A | 10/1994 | White | 204/406 | 5,628,890 A | 5/1997 | Carter | 204/403 |
| 5,354,287 A | 10/1994 | Wacks | 604/232 | 5,640,954 A | 6/1997 | Pfeiffer | 128/635 |
| 5,354,447 A | 10/1994 | Uenoyama | 204/403 | 5,643,306 A | 7/1997 | Schraga | 606/182 |
| 5,356,420 A | 10/1994 | Czernecki | 606/182 | 5,645,555 A | 7/1997 | Davis | 606/182 |
| 5,360,410 A | 11/1994 | Wacks | 604/232 | 5,650,062 A | 7/1997 | Ikeda | 205/778 |
| 5,366,469 A | 11/1994 | Steg | 606/182 | 5,653,863 A | 8/1997 | Genshaw | 205/777.5 |
| 5,366,470 A | 11/1994 | Ramel | 606/183 | 5,657,760 A | 8/1997 | Ying et al. | 128/660.03 |
| 5,366,609 A | 11/1994 | White | 204/403 | 5,658,444 A | 8/1997 | Black | 204/415 |
| 5,371,687 A | 12/1994 | Holmes | 364/514 | 5,662,127 A | 9/1997 | De Vaughn | 128/765 |
| 5,375,397 A | 12/1994 | Ferrand | 54/66 | 5,662,672 A | 9/1997 | Pambianchi | 606/181 |
| 5,378,628 A | 1/1995 | Graetzel | 435/288 | 5,676,143 A | 10/1997 | Simonsen | 128/633 |
| 5,382,346 A | 1/1995 | Uenoyama | 204/403 | 5,680,858 A | 10/1997 | Hansen | 128/635 |
| 5,383,885 A | 1/1995 | Bland | 606/182 | 5,680,872 A | 10/1997 | Sesekura | 128/760 |
| 5,389,534 A | 2/1995 | Gentezkow | 435/180 | 5,682,884 A | 11/1997 | Hill | 128/637 |
| 5,393,903 A | 2/1995 | Graetzel | 556/137 | 5,683,562 A | 11/1997 | Schaffar | 204/403 |
| 5,395,387 A | 3/1995 | Burns | 606/181 | 5,695,947 A | 12/1997 | Guo | 435/11 |
| 5,397,334 A | 3/1995 | Schenk | 606/182 | 5,700,695 A | 12/1997 | Yassinzadeh | 436/180 |
| 5,401,376 A | 3/1995 | Foos | 204/415 | 5,705,045 A | 1/1998 | Park | 204/403 |
| 5,402,798 A | 4/1995 | Swierczek | 128/770 | 5,708,247 A | 1/1998 | McAleer | 204/403 |
| 5,405,511 A | 4/1995 | White | 204/153.1 | 5,709,668 A | 1/1998 | Wacks | 604/232 |
| 5,407,545 A | 4/1995 | Hirose | 204/153.12 | 5,709,699 A | 1/1998 | Warner | 606/181 |
| 5,407,554 A | 4/1995 | Saurer | 204/403 | 5,710,011 A | 1/1998 | Forrow | 435/25 |
| 5,407,818 A | 4/1995 | Gentezkow | 435/180 | 5,720,862 A | 2/1998 | Hamamoto | 204/403 |
| 5,409,583 A | 4/1995 | Yoshioka | 204/153.12 | 5,720,924 A | 2/1998 | Eikmeier | 422/102 |
| 5,409,664 A | 4/1995 | Allen | | D392,391 S | 3/1998 | Douglas et al. | D24/225 |
| 5,410,059 A | 4/1995 | Fraser | 546/10 | 5,723,284 A | 3/1998 | Ye | 435/4 |
| 5,423,847 A | 6/1995 | Strong et al. | 606/182 | 5,727,548 A | 3/1998 | Hill | 128/637 |
| 5,436,161 A | 7/1995 | Bergstrom | 435/291 | 5,730,753 A | 3/1998 | Morita | 606/181 |
| 5,437,999 A | 8/1995 | Diebold | 435/288 | 5,733,300 A | 3/1998 | Pambianchi | 606/181 |
| 5,438,271 A | 8/1995 | White | 324/444 | D393,716 S | 4/1998 | Brenneman et al. | D24/147 |
| 5,443,701 A | 8/1995 | Willner | 204/153 | D393,717 S | 4/1998 | Brenneman et al. | D24/147 |
| 5,445,920 A | 8/1995 | Saito | 430/311 | 5,738,244 A | 4/1998 | Charlton et al. | 221/26 |
| D362,719 S | 9/1995 | Kaplan | D24/147 | 5,741,228 A | 4/1998 | Lambrecht | 604/93 |
| 5,454,828 A | 10/1995 | Schraga | 606/181 | 5,741,634 A | 4/1998 | Nozoe | 435/4 |
| 5,456,875 A | 10/1995 | Lambert | 264/328.1 | RE35,803 E | 5/1998 | Lange | 606/182 |
| 5,464,418 A | 11/1995 | Schraga | 606/182 | 5,746,217 A | 5/1998 | Erickson | 128/760 |
| 5,471,102 A | 11/1995 | Becker | 310/50 | 5,746,898 A | 5/1998 | Preidel | 204/403 |
| 5,476,474 A | 12/1995 | Davis | 606/182 | 5,755,733 A | 5/1998 | Morita | 606/182 |
| 5,480,387 A | 1/1996 | Gabriel | 604/134 | 5,759,364 A | 6/1998 | Charlton | 204/403 |
| 5,487,748 A | 1/1996 | Marshall | 606/182 | 5,762,770 A | 6/1998 | Pritchard | 204/403 |
| 5,496,453 A | 3/1996 | Uenoyama | 205/777.5 | 5,770,086 A | 6/1998 | Indriksons et al. | |
| 5,498,542 A | 3/1996 | Corey | 435/283.1 | 5,770,369 A | 6/1998 | Meade | 435/6 |
| 5,507,288 A | 4/1996 | Bocker | 128/633 | 5,772,586 A | 6/1998 | Heinonen | 600/300 |
| 5,508,171 A | 4/1996 | Walling | 205/777.5 | 5,772,677 A | 6/1998 | Mawhirt | 606/181 |
| 5,509,410 A | 4/1996 | Hill | 128/637 | 5,773,270 A | 6/1998 | D'Orazio | 435/177 |
| 5,510,266 A | 4/1996 | Bonner et al. | 436/43 | 5,776,719 A | 7/1998 | Douglas | 435/28 |
| 5,512,159 A | 4/1996 | Yoshioka | 204/403 | 5,782,770 A | 7/1998 | Mooradian et al. | 600/476 |
| 5,514,152 A | 5/1996 | Smith | | 5,782,852 A | 7/1998 | Foggia | 606/182 |
| 5,518,006 A | 5/1996 | Mawhirt | 128/770 | 5,788,652 A | 8/1998 | Rahn | 600/577 |
| 5,524,636 A | 6/1996 | Sarvazyan | 128/774 | 5,794,219 A | 8/1998 | Brown | 705/37 |
| 5,525,511 A | 6/1996 | D'Costa | 435/287.9 | 5,795,725 A | 8/1998 | Buechler | 435/7.1 |
| 5,527,333 A | 6/1996 | Nikkels | 606/182 | 5,795,774 A | 8/1998 | Matsumoto | 435/287.9 |
| 5,527,334 A | 6/1996 | Kanner | 606/182 | 5,797,940 A | 8/1998 | Mawhirt | 606/167 |
| 5,540,709 A | 7/1996 | Ramel | 606/183 | 5,797,942 A | 8/1998 | Schraga | 606/182 |
| 5,543,326 A | 8/1996 | Heller | 435/287.9 | 5,798,030 A | 8/1998 | Raguse | 204/403 |
| 5,545,174 A | 8/1996 | Schenk | 606/182 | 5,798,031 A | 8/1998 | Charlton | 204/403 |
| 5,547,702 A | 8/1996 | Gleisner | 427/2.13 | 5,800,781 A | 9/1998 | Gavin | 422/73 |
| 5,554,166 A | 9/1996 | Lange | 606/182 | 5,801,057 A | 9/1998 | Smart | 436/68 |
| 5,558,834 A | 9/1996 | Chu | 422/55 | 5,807,375 A | 9/1998 | Gross | 604/890.1 |
| 5,569,286 A | 10/1996 | Peckham | 606/181 | 5,820,551 A | 10/1998 | Hill | 600/347 |
| 5,569,287 A | 10/1996 | Tezuka | 606/182 | 5,822,715 A | 10/1998 | Worthington | 702/19 |
| 5,571,132 A | 11/1996 | Mawhirt | 606/182 | 5,824,491 A | 10/1998 | Priest | 435/28 |
| 5,575,895 A | 11/1996 | Ikeda | 204/403 | 5,828,943 A | 10/1998 | Brown | 434/258 |
| 5,582,697 A | 12/1996 | Ikeda | 204/403 | 5,830,219 A | 11/1998 | Bird et al. | 606/130 |
| 5,584,846 A | 12/1996 | Mawhirt | 606/181 | 5,832,448 A | 11/1998 | Brown | 705/2 |
| 5,593,852 A | 1/1997 | Heller | 435/14 | 5,840,020 A | 11/1998 | Heinonen | 600/309 |
| 5,609,749 A | 3/1997 | Yamauchi | 205/777.5 | 5,840,171 A | 11/1998 | Birch | 205/335 |
| 5,613,978 A | 3/1997 | Harding | 606/181 | 5,849,174 A | 12/1998 | Sanghera | 205/775 |
| 5,620,279 A | 4/1997 | Genshaw | 204/402 | 5,853,373 A | 12/1998 | Griffith | 600/554 |
| 5,624,537 A | 4/1997 | Turner | 204/403 | D403,975 S | 1/1999 | Douglas et al. | D10/81 |
| D379,516 S | 5/1997 | Rutter | D24/146 | 5,857,983 A | 1/1999 | Douglas | 600/538 |
| 5,628,764 A | 5/1997 | Schraga | 606/182 | 5,860,922 A | 1/1999 | Gordon et al. | 600/431 |
| 5,628,765 A | 5/1997 | Morita | 606/182 | 5,866,353 A | 2/1999 | Berneth | 435/26 |

| Patent | Date | Name | Ref |
|---|---|---|---|
| 5,868,135 A | 2/1999 | Kaufman | 128/630 |
| 5,868,772 A | 2/1999 | LeVaughn | 606/181 |
| 5,869,972 A | 2/1999 | Birch | 324/439 |
| 5,871,494 A | 2/1999 | Simons et al. | |
| 5,872,713 A | 2/1999 | Douglas | 702/85 |
| 5,873,887 A | 2/1999 | King | 606/182 |
| 5,876,957 A | 3/1999 | Douglas | 435/28 |
| 5,879,163 A | 3/1999 | Brown | 434/236 |
| 5,879,310 A | 3/1999 | Sopp | 600/578 |
| 5,879,373 A | 3/1999 | Roper | 606/344 |
| 5,882,494 A | 3/1999 | van Antwerp | 204/403 |
| 5,885,211 A | 3/1999 | Eppstein | 600/309 |
| 5,887,133 A | 3/1999 | Brown | 395/200.3 |
| RE36,191 E | 4/1999 | Solomon | 395/308 |
| 5,893,870 A | 4/1999 | Talen | 606/201 |
| 5,897,493 A | 4/1999 | Brown | 600/300 |
| 5,899,855 A | 5/1999 | Brown | 600/301 |
| 5,899,915 A | 5/1999 | Saadat | |
| 5,900,130 A | 5/1999 | Benvegnu | 204/453 |
| 5,906,921 A | 5/1999 | Ikeda | 435/25 |
| D411,619 S | 6/1999 | Duchon | D24/146 |
| 5,913,310 A | 6/1999 | Brown | 128/897 |
| 5,916,156 A | 6/1999 | Hildenbrand | 600/347 |
| 5,916,229 A | 6/1999 | Evans | 606/171 |
| 5,916,230 A | 6/1999 | Brenneman | 606/172 |
| 5,918,603 A | 7/1999 | Brown | 128/897 |
| 5,921,963 A | 7/1999 | Erez | 604/192 |
| 5,922,188 A | 7/1999 | Ikeda | 204/777.5 |
| RE36,268 E | 8/1999 | Szuminsky | 205/777.5 |
| 5,933,136 A | 8/1999 | Brown | 345/327 |
| 5,935,075 A | 8/1999 | Casscells et al. | 600/474 |
| 5,942,102 A | 8/1999 | Hodges | 205/775 |
| 5,951,300 A | 9/1999 | Brown | 434/236 |
| 5,951,492 A | 9/1999 | Douglas | 600/583 |
| 5,951,493 A | 9/1999 | Douglas et al. | 600/583 |
| 5,951,836 A | 9/1999 | McAleer | 204/403 |
| 5,954,738 A | 9/1999 | LeVaughn | 606/181 |
| 5,956,501 A | 9/1999 | Brown | 395/500.32 |
| 5,958,199 A | 9/1999 | Miyamoto | 204/403 |
| 5,960,403 A | 9/1999 | Brown | 705/2 |
| 5,964,718 A | 10/1999 | Duchon | 600/583 |
| 5,965,380 A | 10/1999 | Heller | 435/14 |
| 5,972,199 A | 10/1999 | Heller | 205/777.5 |
| 5,972,715 A | 10/1999 | Celentano | 436/164 |
| 5,974,124 A | 10/1999 | Schlueter | 379/106.02 |
| 5,983,193 A | 11/1999 | Heinonen | 705/2 |
| 5,985,116 A | 11/1999 | Ikeda | 204/403 |
| 5,985,559 A | 11/1999 | Brown | 435/6 |
| 5,993,400 A | 11/1999 | Rincoe | 600/595 |
| 5,997,476 A | 12/1999 | Brown | 600/300 |
| 5,997,561 A | 12/1999 | Boecker | 606/182 |
| 5,997,817 A | 12/1999 | Crismore | 422/58 |
| 5,997,818 A | 12/1999 | Hackner | 422/681 |
| 6,001,067 A | 12/1999 | Shults | 600/584 |
| 6,015,392 A | 1/2000 | Douglas | 600/583 |
| 6,020,110 A | 2/2000 | Williams | 430/315 |
| 6,022,324 A | 2/2000 | Skinner | 600/566 |
| 6,022,366 A | 2/2000 | Schraga | 606/182 |
| 6,023,686 A | 2/2000 | Brown | 705/37 |
| 6,030,399 A | 2/2000 | Ignotz | 606/167 |
| 6,030,827 A | 2/2000 | Davis | 435/287 |
| 6,032,119 A | 2/2000 | Brown | 705/2 |
| 6,033,421 A | 3/2000 | Theiss | 606/186 |
| 6,033,866 A | 3/2000 | Guo | 435/14 |
| 6,041,253 A | 3/2000 | Kost | 604/20 |
| 6,048,352 A | 4/2000 | Douglas | 606/181 |
| D424,696 S | 5/2000 | Ray et al. | D24/169 |
| 6,056,701 A | 5/2000 | Duchon | 600/583 |
| 6,060,327 A | 5/2000 | Keen | 436/518 |
| 6,061,128 A | 5/2000 | Zweig | 356/243.4 |
| 6,063,039 A | 5/2000 | Cunningham | 600/573 |
| 6,066,103 A | 5/2000 | Duchon | 600/583 |
| 6,066,296 A | 5/2000 | Brady | 422/63 |
| 6,067,463 A | 5/2000 | Jeng | 600/336 |
| 6,068,615 A | 5/2000 | Brown | 604/207 |
| D426,638 S | 6/2000 | Ray et al. | D24/169 |
| 6,071,249 A | 6/2000 | Cunningham | 600/578 |
| 6,071,250 A | 6/2000 | Douglas | 600/583 |
| 6,071,251 A | 6/2000 | Cunningham | 600/584 |
| 6,074,360 A | 6/2000 | Haar et al. | 604/57 |
| 6,077,408 A | 6/2000 | Miyamoto | 204/403 |
| 6,080,172 A | 6/2000 | Fujiwara | 606/166 |
| 6,083,710 A | 7/2000 | Heller | 435/14 |
| 6,086,545 A | 7/2000 | Roe | 600/570 |
| 6,086,562 A | 7/2000 | Jacobsen | 604/156 |
| 6,090,078 A | 7/2000 | Erskine | 604/198 |
| 6,093,146 A | 7/2000 | Filangeri | 600/300 |
| 6,101,478 A | 8/2000 | Brown | 705/2 |
| 6,103,033 A | 8/2000 | Say | 156/73.1 |
| 6,107,083 A | 8/2000 | Collins | 435/288 |
| 6,113,578 A | 9/2000 | Brown | 604/207 |
| 6,120,676 A | 9/2000 | Heller | 205/777.5 |
| 6,121,009 A | 9/2000 | Heller | 435/14 |
| 6,122,536 A | 9/2000 | Sun | 600/341 |
| 6,129,823 A | 10/2000 | Hughes | 204/403.01 |
| 6,133,837 A | 10/2000 | Riley | 340/573.1 |
| 6,134,461 A | 10/2000 | Say | 600/345 |
| 6,144,837 A | 11/2000 | Quy | 434/307 R |
| 6,151,586 A | 11/2000 | Brown | 705/14 |
| 6,153,069 A | 11/2000 | Pottgen | 204/403 |
| RE36,991 E | 12/2000 | Yamamoto | 204/403 |
| 6,155,267 A | 12/2000 | Nelson | 128/899 |
| 6,155,992 A | 12/2000 | Henning et al. | 600/583 |
| 6,157,442 A | 12/2000 | Raskas | 356/39 |
| 6,161,095 A | 12/2000 | Brown | 705/2 |
| 6,162,611 A | 12/2000 | Heller | 435/14 |
| 6,167,362 A | 12/2000 | Brown | 703/11 |
| 6,167,386 A | 12/2000 | Brown | 705/37 |
| 6,168,563 B1 | 1/2001 | Brown | 600/301 |
| 6,171,325 B1 | 1/2001 | Mauze et al. | 606/171 |
| 6,175,752 B1 | 1/2001 | Say | 600/345 |
| 6,177,000 B1 | 1/2001 | Peterson | 205/777.5 |
| 6,177,931 B1 | 1/2001 | Alexander et al. | |
| 6,186,145 B1 | 2/2001 | Brown | 128/897 |
| 6,190,612 B1 | 2/2001 | Berger | 422/82.07 |
| 6,191,852 B1 | 2/2001 | Paffhausen | 356/244 |
| 6,192,891 B1 | 2/2001 | Gravel | 128/920 |
| 6,194,900 B1 | 2/2001 | Freeman | 324/321 |
| 6,197,257 B1 | 3/2001 | Raskas | 422/82.05 |
| 6,206,841 B1 | 3/2001 | Cunningham et al. | 600/584 |
| 6,210,272 B1 | 4/2001 | Brown | 463/1 |
| 6,212,417 B1 | 4/2001 | Ikeda | 204/403.14 |
| 6,214,804 B1 | 4/2001 | Felgner | 514/44 |
| 6,221,238 B1 | 4/2001 | Grundig | 205/777.5 |
| 6,225,078 B1 | 5/2001 | Ikeda | 435/25 |
| 6,230,501 B1 | 5/2001 | Bailey | 62/51.1 |
| 6,233,471 B1 | 5/2001 | Berner | 600/345 |
| 6,233,539 B1 | 5/2001 | Brown | 703/11 |
| 6,240,393 B1 | 5/2001 | Brown | 705/1 |
| 6,241,862 B1 | 6/2001 | McAleer | 204/403 |
| 6,245,060 B1 | 6/2001 | Loomis | 606/9 |
| 6,246,992 B1 | 6/2001 | Brown | 705/2 |
| 6,248,065 B1 | 6/2001 | Brown | 600/300 |
| 6,251,260 B1 | 6/2001 | Heller | 205/777.5 |
| 6,254,831 B1 | 7/2001 | Barnard | 422/82.08 |
| 6,256,533 B1 | 7/2001 | Vuzhakov | 604/21 |
| 6,258,229 B1 | 7/2001 | Winarta | 204/403 |
| 6,258,254 B1 | 7/2001 | Miyamoto | 205/777.5 |
| 6,268,161 B1 | 7/2001 | Han | 435/14 |
| 6,270,455 B1 | 8/2001 | Brown | 600/300 |
| 6,270,637 B1 | 8/2001 | Crismore | 204/403 |
| 6,272,359 B1 | 8/2001 | Kivela | 455/567 |
| 6,281,006 B1 | 8/2001 | Heller | 435/287.9 |
| 6,283,982 B1 | 9/2001 | Levaughn | 606/172 |
| 6,284,478 B1 | 9/2001 | Heller | 435/14 |
| 6,285,448 B1 | 9/2001 | Kuenstner | 356/39 |

| Patent No. | Date | Name | Class |
|---|---|---|---|
| 6,290,683 B1 | 9/2001 | Erez | 604/273 |
| 6,294,897 B1 | 9/2001 | Champlin | 320/153 |
| 6,295,506 B1 | 9/2001 | Heinonen | 702/104 |
| 6,299,757 B1 | 10/2001 | Feldman | 205/775 |
| 6,302,844 B1 | 10/2001 | Walker | 600/300 |
| 6,302,855 B1 | 10/2001 | Lav | 600/584 |
| 6,305,804 B1 | 10/2001 | Rice | 351/221 |
| 6,306,347 B1 | 10/2001 | Mason | 422/58 |
| 6,309,535 B1 | 10/2001 | Williams | 205/777.5 |
| 6,312,612 B1 | 11/2001 | Sherman | 216/2 |
| 6,322,574 B1 | 11/2001 | Lloyd | 606/181 |
| 6,329,161 B1 | 12/2001 | Heller | 435/14 |
| 6,330,426 B2 | 12/2001 | Brown | 434/307 R |
| 6,331,163 B1 | 12/2001 | Kaplan | 600/486 |
| 6,334,363 B1 | 1/2002 | Testud | 73/862 |
| 6,334,778 B1 | 1/2002 | Brown | 434/258 |
| 6,334,856 B1 | 1/2002 | Allen | 604/191 |
| 6,338,790 B1 | 1/2002 | Feldman | 205/777.5 |
| 6,349,229 B1 | 2/2002 | Watanabe | 600/345 |
| 6,350,273 B1 | 2/2002 | Minagawa | 606/186 |
| 6,350,451 B1 | 2/2002 | Horn | 424/184.1 |
| 6,352,523 B1 | 3/2002 | Brown | 604/207 |
| 6,353,753 B1 | 3/2002 | Flock | 600/473 |
| 6,364,889 B1 | 4/2002 | Kheiri et al. | 606/181 |
| 6,368,273 B1 | 4/2002 | Brown | 600/300 |
| 6,375,469 B1 | 4/2002 | Brown | 434/236 |
| 6,379,301 B1 | 4/2002 | Worthington | 600/309 |
| 6,379,324 B1 | 4/2002 | Gartstein | 604/22 |
| 6,381,577 B1 | 4/2002 | Brown | 705/2 |
| 6,387,709 B1 | 5/2002 | Mason | 436/164 |
| 6,399,394 B1 | 6/2002 | Dahm | 436/180 |
| 6,413,410 B1 | 7/2002 | Hodges | 205/775 |
| 6,413,411 B1 | 7/2002 | Pottgen | 205/777.5 |
| 6,421,633 B1 | 7/2002 | Heinonen | 703/11 |
| 6,423,014 B1 | 7/2002 | Churchill et al. | |
| 6,428,664 B1 | 8/2002 | Bhullar | 204/403.03 |
| 6,436,256 B1 | 8/2002 | Williams | 204/403.06 |
| 6,436,721 B1 | 8/2002 | Kuo | 436/514 |
| 6,440,645 B1 | 8/2002 | Yon-Hin | 430/322 |
| 6,451,040 B1 | 9/2002 | Purcell | 606/181 |
| 6,458,258 B2 | 10/2002 | Taniike | 204/403 |
| 6,462,162 B2 | 10/2002 | van Antwerp | 528/77 |
| 6,464,649 B1 | 10/2002 | Duchon | 600/583 |
| 6,471,903 B2 | 10/2002 | Sherman | 264/328.1 |
| 6,475,436 B1 | 11/2002 | Schabbach | 422/64 |
| 6,475,750 B1 | 11/2002 | Han et al. | 435/14 |
| 6,477,394 B2 | 11/2002 | Rice | 600/318 |
| 6,477,424 B1 | 11/2002 | Thompson | 607/60 |
| 6,484,046 B1 | 11/2002 | Say | 600/345 |
| 6,494,830 B1 | 12/2002 | Wessel | 600/300 |
| 6,501,404 B2 | 12/2002 | Walker | 341/143 |
| 6,503,231 B1 | 1/2003 | Prausnitz | 604/272 |
| 6,503,381 B1 | 1/2003 | Gotoh | 204/403.14 |
| 6,506,168 B1 | 1/2003 | Fathallah | 600/578 |
| 6,508,785 B1 | 1/2003 | Eppstein | 604/113 |
| 6,514,270 B1 | 2/2003 | Schraga | 606/182 |
| 6,514,460 B1 | 2/2003 | Fendrock | 422/55 |
| 6,519,241 B1 | 2/2003 | Theimer | 370/338 |
| 6,520,326 B2 | 2/2003 | McIvor | 206/305 |
| 6,527,778 B2 | 3/2003 | Athanasiou | 606/80 |
| 6,530,892 B1 | 3/2003 | Kelly | 600/583 |
| 6,530,937 B1 | 3/2003 | Schraga | 606/182 |
| 6,533,949 B1 | 3/2003 | Yeshurun | 216/11 |
| 6,537,207 B1 | 3/2003 | Rice | 600/121 |
| 6,537,242 B1 | 3/2003 | Palmer | 604/22 |
| 6,537,292 B1 | 3/2003 | Lee | 606/182 |
| 6,540,672 B1 | 4/2003 | Simonsen | 600/300 |
| 6,540,675 B2 | 4/2003 | Aceti | 600/309 |
| 6,540,762 B1 | 4/2003 | Bertling | 606/182 |
| 6,540,891 B1 | 4/2003 | Stewart | 204/403.14 |
| 6,541,266 B2 | 4/2003 | Modzelewski | 436/95 |
| 6,547,954 B2 | 4/2003 | Ikeda | 205/777.5 |
| 6,549,796 B2 | 4/2003 | Sohrab | 600/345 |
| 6,551,494 B1 | 4/2003 | Heller | 205/777.5 |
| 6,553,244 B2 | 4/2003 | Lesho | 600/347 |
| 6,554,381 B2 | 4/2003 | Locher | 347/7 |
| 6,555,061 B1 | 4/2003 | Leong | 422/58 |
| 6,558,320 B1 | 5/2003 | Causey | 600/300 |
| 6,558,361 B1 | 5/2003 | Yeshurun | 604/272 |
| 6,558,402 B1 | 5/2003 | Chelak | 606/182 |
| 6,558,528 B1 | 5/2003 | Matzinger | 205/777.5 |
| 6,560,471 B1 | 5/2003 | Heller | 600/347 |
| 6,561,978 B1 | 5/2003 | Conn | 600/309 |
| 6,561,989 B2 | 5/2003 | Whitson | 600/573 |
| 6,562,210 B1 | 5/2003 | Bhullar | 204/403.3 |
| 6,565,509 B1 | 5/2003 | Say | 600/365 |
| 6,565,808 B2 | 5/2003 | Hudak | 422/58 |
| 6,569,157 B1 | 5/2003 | Shain | 606/12 |
| 6,571,651 B1 | 6/2003 | Hodges | 73/864.72 |
| 6,572,566 B2 | 6/2003 | Effenhauser | 600/584 |
| 6,574,490 B2 | 6/2003 | Abbink | 600/316 |
| 6,575,905 B2 | 6/2003 | Knobbe | 600/365 |
| 6,576,101 B1 | 6/2003 | Heller | 204/403.14 |
| 6,576,117 B1 | 6/2003 | Iketaki | 205/777.5 |
| 6,576,416 B2 | 6/2003 | Haviland | 435/4 |
| 6,582,573 B2 | 6/2003 | Douglas | 204/403.1 |
| 6,587,705 B1 | 7/2003 | Kim | 600/347 |
| 6,589,260 B1 | 7/2003 | Schmelzeisen-R | 606/181 |
| 6,589,261 B1 | 7/2003 | Abulhaj | 606/181 |
| 6,591,125 B1 | 7/2003 | Buse | 600/347 |
| 6,592,745 B1 | 7/2003 | Feldman | 205/777.5 |
| 6,595,919 B2 | 7/2003 | Berner | 600/365 |
| 6,599,407 B2 | 7/2003 | Taniike | 204/403.1 |
| 6,599,693 B1 | 7/2003 | Webb | 435/4 |
| 6,602,205 B1 | 8/2003 | Erickson | 600/573 |
| 6,602,268 B2 | 8/2003 | Kuhr | 606/181 |
| 6,602,678 B2 | 8/2003 | Kwon | 435/14 |
| 6,604,050 B2 | 8/2003 | Trippel | 702/19 |
| 6,607,494 B1 | 8/2003 | Fowler | 600/570 |
| 6,607,658 B1 | 8/2003 | Heller | 205/777.5 |
| 6,616,616 B2 | 9/2003 | Fritz | 600/583 |
| 6,616,819 B1 | 9/2003 | Liamos | 204/403.02 |
| 6,618,934 B1 | 9/2003 | Feldman | 29/830 |
| 6,620,112 B2 | 9/2003 | Klitmose | 600/583 |
| 6,623,501 B2 | 9/2003 | Heller | 606/181 |
| 6,626,851 B2 | 9/2003 | Hirao | 600/576 |
| 6,635,222 B2 | 10/2003 | Kent | 422/22 |
| 6,638,772 B1 | 10/2003 | Douglas | 436/518 |
| 6,641,533 B2 | 11/2003 | Causey | 600/300 |
| 6,645,142 B2 | 11/2003 | Braig | 600/300 |
| 6,645,219 B2 | 11/2003 | Roe | 606/182 |
| 6,645,368 B1 | 11/2003 | Beatty | 205/792 |
| 6,650,915 B2 | 11/2003 | Routt | 600/319 |
| 6,652,720 B1 | 11/2003 | Mansouri | 204/403.11 |
| 6,656,702 B1 | 12/2003 | Yugawa | 435/26 |
| 6,659,966 B2 | 12/2003 | Essenpreis | 600/583 |
| 6,660,018 B2 | 12/2003 | Lum | 606/181 |
| 6,671,527 B2 | 12/2003 | Peterson | 600/316 |
| 6,679,841 B2 | 1/2004 | Bojan | 600/309 |
| 6,679,852 B1 | 1/2004 | Schmelzeisen-R | 600/583 |
| 6,706,000 B2 | 3/2004 | Perez | 600/583 |
| 6,706,049 B2 | 3/2004 | Moerman | 606/181 |
| 6,706,159 B2 | 3/2004 | Moerman | 204/403.03 |
| 6,706,232 B2 | 3/2004 | Hasegawa | 264/403.09 |
| 6,713,660 B1 | 3/2004 | Roe | 604/361 |
| 6,719,887 B2 | 4/2004 | Hasegawa | 204/403.09 |
| 6,719,923 B2 | 4/2004 | Stiene | 252/511 |
| 6,721,586 B2 | 4/2004 | Kiser | 600/345 |
| 6,723,046 B2 | 4/2004 | Lichtenstein | 600/300 |
| 6,723,111 B2 | 4/2004 | Abulhaj | 606/181 |
| 6,723,371 B2 | 4/2004 | Chih-hui | 472/2.13 |
| 6,723,500 B2 | 4/2004 | Yu | 435/4 |
| 6,726,818 B2 | 4/2004 | Cui et al. | 204/403.01 |
| 6,733,493 B2 | 5/2004 | Gruzdev | 606/9 |
| 6,736,777 B2 | 5/2004 | Kim | 600/365 |
| 6,740,215 B1 | 5/2004 | Nakaminami et al. | 204/403.14 |

| Patent | Date | Name | Class |
|---|---|---|---|
| 6,743,211 B1 | 6/2004 | Prausnitz | 604/239 |
| 6,743,635 B2 | 6/2004 | Neel | 436/95 |
| 6,749,618 B2 | 6/2004 | Levaughn | 606/182 |
| 6,749,792 B2 | 6/2004 | Olson | 264/328.1 |
| 6,751,491 B2 | 6/2004 | Lew | 600/345 |
| 6,752,817 B2 | 6/2004 | Flora | 606/181 |
| 6,759,190 B2 | 7/2004 | Lin | 435/4 |
| 6,764,496 B2 | 7/2004 | Schraga | 606/182 |
| 6,764,581 B1 | 7/2004 | Forrow | 204/403 |
| 6,767,441 B1 | 7/2004 | Cai | 204/403.03 |
| 6,773,671 B1 | 8/2004 | Lewis | 422/58 |
| 6,776,888 B2 | 8/2004 | Yamamoto | 204/403.06 |
| 6,780,645 B2 | 8/2004 | Hayter | 436/8 |
| 6,780,647 B2 | 8/2004 | Fujiwara | 436/169 |
| 6,783,502 B2 | 8/2004 | Orloff | 600/583 |
| 6,783,537 B1 | 8/2004 | Kuhr | 606/182 |
| 6,784,274 B2 | 8/2004 | van Antwerp | 528/77 |
| 6,786,874 B2 | 9/2004 | Grace | 600/573 |
| 6,787,013 B2 | 9/2004 | Chang | 204/412 |
| 6,787,109 B2 | 9/2004 | Haar | 422/82.05 |
| 6,790,327 B2 | 9/2004 | Ikeda | 204/403.1 |
| 6,790,599 B1 | 9/2004 | Madou | 430/320 |
| 6,792,791 B2 | 9/2004 | Sato | 73/1.02 |
| 6,793,632 B2 | 9/2004 | Sohrab | 600/573 |
| 6,793,633 B2 | 9/2004 | Douglas | 600/583 |
| 6,793,802 B2 | 9/2004 | Lee | 205/777.5 |
| 6,797,150 B2 | 9/2004 | Kermani | 205/777.5 |
| 6,800,488 B2 | 10/2004 | Khan | 436/166 |
| 6,801,041 B2 | 10/2004 | Karinka | 324/44 |
| 6,801,804 B2 | 10/2004 | Miller | 604/20 |
| 6,802,199 B2 | 10/2004 | Hilgers | 72/370.1 |
| 6,802,811 B1 | 10/2004 | Slepian | 600/309 |
| 6,802,957 B2 | 10/2004 | Jung | 205/777.5 |
| 6,805,780 B1 | 10/2004 | Ryu | 204/403.01 |
| 6,808,499 B1 | 10/2004 | Churchill | 600/587 |
| 6,808,908 B2 | 10/2004 | Yao | 435/181 |
| 6,808,937 B2 | 10/2004 | Ligler | 436/518 |
| 6,809,807 B1 | 10/2004 | Erickson | 356/213 |
| 6,811,406 B2 | 11/2004 | Grubge | |
| 6,811,557 B2 | 11/2004 | Schraga | 606/182 |
| 6,811,659 B2 | 11/2004 | Vachon | 204/224 |
| 6,811,753 B2 | 11/2004 | Hirao | 422/101 |
| 6,811,792 B2 | 11/2004 | Roser | 424/423 |
| 6,812,031 B1 | 11/2004 | Carlsson | 436/52 |
| 6,814,843 B1 | 11/2004 | Bhullar | 204/403.01 |
| 6,814,844 B2 | 11/2004 | Bhullar | 204/403.1 |
| 6,814,845 B2 | 11/2004 | Wilson | 204/486 |
| 6,815,186 B2 | 11/2004 | Clark | 435/183 |
| 6,816,742 B2 | 11/2004 | Kim | 600/345 |
| 6,818,180 B2 | 11/2004 | Douglas | 422/58 |
| 6,821,483 B2 | 11/2004 | Phillips | 422/58 |
| 6,823,750 B2 | 11/2004 | Hodges | 73/864.72 |
| 6,825,047 B1 | 11/2004 | Woudenberg | 436/518 |
| 6,827,250 B2 | 12/2004 | Uhland | 228/110.1 |
| 6,827,829 B2 | 12/2004 | Kawanaka | 204/403.02 |
| 6,830,551 B1 | 12/2004 | Uchigaki | 600/584 |
| 6,830,668 B2 | 12/2004 | Musho | 204/400 |
| 6,830,669 B2 | 12/2004 | Miyazaki | 204/409 |
| 6,833,540 B2 | 12/2004 | MacKenzie | 250/214 |
| 6,835,184 B1 | 12/2004 | Sage | 604/46 |
| 6,835,553 B2 | 12/2004 | Han | 435/14 |
| 6,837,858 B2 | 1/2005 | Cunningham | 600/573 |
| 6,837,976 B2 | 1/2005 | Cai | 204/403.14 |
| 6,837,988 B2 | 1/2005 | Leong | 205/792 |
| 6,840,912 B2 | 1/2005 | Kloepfer et al. | 600/583 |
| 6,841,052 B2 | 1/2005 | Musho | 204/401 |
| 6,843,254 B2 | 1/2005 | Tapper | 128/898 |
| 6,844,149 B2 | 1/2005 | Goldman | 435/4 |
| 6,847,451 B2 | 1/2005 | Pugh | 356/436 |
| 6,849,052 B2 | 2/2005 | Uchigaki et al. | |
| 6,849,168 B2 | 2/2005 | Crumly | 204/416 |
| 6,849,216 B2 | 2/2005 | Rappin | 264/134 |
| 6,850,790 B2 | 2/2005 | Berner et al. | 600/347 |
| 6,869,418 B2 | 3/2005 | Marano-Ford | 604/192 |
| 6,872,200 B2 | 3/2005 | Mann | 604/890.1 |
| 6,875,208 B2 | 4/2005 | Santini | 604/890.1 |
| 6,875,223 B2 | 4/2005 | Argauer | 606/181 |
| 6,875,613 B2 | 4/2005 | Shartle | 436/63 |
| 6,878,120 B2 | 4/2005 | Roe | 600/583 |
| 6,878,251 B2 | 4/2005 | Hodges | 204/403.14 |
| 6,878,255 B1 | 4/2005 | Wang | 204/452 |
| 6,878,262 B2 | 4/2005 | Taniike | 205/777.5 |
| 6,880,968 B1 | 4/2005 | Haar | 374/131 |
| 6,881,203 B2 | 4/2005 | Delmore | 604/272 |
| 6,881,322 B2 | 4/2005 | Tokunaga | 205/775 |
| 6,881,378 B1 | 4/2005 | Zimmer | 422/58 |
| 6,881,541 B2 | 4/2005 | Petersen et al. | |
| 6,881,550 B2 | 4/2005 | Phillips | 435/14 |
| 6,881,551 B2 | 4/2005 | Heller | 435/14 |
| 6,881,578 B2 | 4/2005 | Otake | 436/44 |
| 6,882,940 B2 | 4/2005 | Potts | 702/23 |
| 6,884,592 B2 | 4/2005 | Matzinger | 435/7.1 |
| 6,885,196 B2 | 4/2005 | Taniike | 324/444 |
| 6,885,883 B2 | 4/2005 | Parris | 600/347 |
| 6,887,239 B2 | 5/2005 | Elstrom | 606/41 |
| 6,887,253 B2 | 5/2005 | Schraga | 606/181 |
| 6,887,254 B1 | 5/2005 | Curie | 606/181 |
| 6,887,426 B2 | 5/2005 | Phillips | 422/56 |
| 6,887,709 B2 | 5/2005 | Leong | 436/8 |
| 6,889,069 B2 | 5/2005 | Routt | 600/319 |
| 6,890,319 B1 | 5/2005 | Crocker | 604/131 |
| 6,890,421 B2 | 5/2005 | Ohara | 205/777.5 |
| 6,890,484 B2 | 5/2005 | Bautista | 422/58 |
| 6,891,936 B2 | 5/2005 | Kai | 379/106.02 |
| 6,892,085 B2 | 5/2005 | McIvor | 600/347 |
| 6,893,396 B2 | 5/2005 | Schulze | 600/300 |
| 6,893,545 B2 | 5/2005 | Gotoh | 204/403.5 |
| 6,893,552 B1 | 5/2005 | Wang | 205/777.5 |
| 6,895,263 B2 | 5/2005 | Shin | 600/316 |
| 6,895,264 B2 | 5/2005 | Rice | 600/319 |
| 6,895,265 B2 | 5/2005 | Silver | 600/345 |
| 6,896,793 B2 | 5/2005 | Erdosy | 205/775 |
| 6,897,788 B2 | 5/2005 | Khair | 340/870.16 |
| 6,902,905 B2 | 6/2005 | Burson | 435/14 |
| 6,904,301 B2 | 6/2005 | Raskas | 600/310 |
| 6,905,733 B2 | 6/2005 | Russel | 427/393.5 |
| 6,908,008 B2 | 6/2005 | Pugh | 221/135 |
| 6,908,535 B2 | 6/2005 | Rankin | 204/406 |
| 6,908,591 B2 | 6/2005 | MacPhee | 422/22 |
| 6,908,593 B1 | 6/2005 | Shartle | 422/58 |
| 6,911,130 B2 | 6/2005 | Brenneman | 204/400 |
| 6,911,131 B2 | 6/2005 | Miyazaki | 204/403.14 |
| 6,911,621 B2 | 6/2005 | Bhullar | 219/121.69 |
| 6,916,410 B2 | 7/2005 | Katsuki | 204/403 |
| 6,918,874 B1 | 7/2005 | Hatch | 600/365 |
| 6,918,901 B1 | 7/2005 | Theeuwes et al. | |
| 6,918,918 B1 | 7/2005 | Schraga | 600/365 |
| 6,922,576 B2 | 7/2005 | Raskas | 600/316 |
| 6,922,578 B2 | 7/2005 | Eppstein | 600/347 |
| 6,923,764 B2 | 8/2005 | Aceti | 600/309 |
| 6,923,894 B2 | 8/2005 | Huang | 204/403.06 |
| 6,923,936 B2 | 8/2005 | Swanson | 422/22 |
| 6,924,093 B2 | 8/2005 | Haviland | 435/4 |
| 6,925,317 B1 | 8/2005 | Samuels | 600/344 |
| 6,925,393 B1 | 8/2005 | Kalatz | 702/27 |
| 6,929,649 B2 | 8/2005 | Pugh | 606/182 |
| 6,929,650 B2 | 8/2005 | Fukuzawa | 606/182 |
| 6,931,327 B2 | 8/2005 | Goode | 702/22 |
| 6,931,328 B2 | 8/2005 | Braig | 702/23 |
| 6,939,310 B2 | 9/2005 | Matzinger | 600/573 |
| 6,939,312 B2 | 9/2005 | Hodges | 600/583 |
| 6,939,450 B2 | 9/2005 | Karinka | 204/409 |
| 6,940,591 B2 | 9/2005 | Sopp | 356/244 |
| 6,942,518 B2 | 9/2005 | Liamos | 439/495 |
| 6,942,769 B2 | 9/2005 | Cheng | 204/400 |
| 6,942,770 B2 | 9/2005 | Cai | 204/403.04 |

| Patent | Date | Name | Class |
|---|---|---|---|
| 6,944,486 B2 | 9/2005 | Braig | 600/310 |
| 6,945,943 B2 | 9/2005 | Pugh | 600/584 |
| 6,946,067 B2 | 9/2005 | Hodges | 205/792 |
| 6,946,098 B2 | 9/2005 | Miekka | 422/22 |
| 6,946,299 B2 | 9/2005 | Neel | 436/95 |
| 6,949,111 B2 | 9/2005 | Schraga | 606/182 |
| 6,949,221 B2 | 9/2005 | Kiser | 422/56 |
| 6,951,631 B1 | 10/2005 | Catt | 422/56 |
| 6,951,728 B2 | 10/2005 | Qian | 435/14 |
| 6,952,603 B2 | 10/2005 | Gerber | 600/310 |
| 6,952,604 B2 | 10/2005 | DeNuzzio | 600/345 |
| 6,953,693 B2 | 10/2005 | Neel | 436/149 |
| 6,954,662 B2 | 10/2005 | Freger | 600/316 |
| 6,958,072 B2 | 10/2005 | Schraga | 606/182 |
| 6,958,129 B2 | 10/2005 | Galen | 422/57 |
| 6,958,809 B2 | 10/2005 | Sterling | 356/39 |
| 6,959,211 B2 | 10/2005 | Rule | 600/310 |
| 6,959,247 B2 | 10/2005 | Neel | 702/19 |
| 6,960,287 B2 | 11/2005 | Charlton | 205/775 |
| 6,960,289 B2 | 11/2005 | Hodges | 205/778 |
| 6,964,871 B2 | 11/2005 | Bell | 436/95 |
| 6,965,791 B1 | 11/2005 | Hitchcock | 600/345 |
| 6,966,880 B2 | 11/2005 | Boecker | 600/583 |
| 6,966,977 B2 | 11/2005 | Hasegawa | 204/403.07 |
| 6,967,105 B2 | 11/2005 | Nomura | 436/169 |
| 6,968,375 B1 | 11/2005 | Brown | 709/224 |
| 6,969,359 B2 | 11/2005 | Duchon | 600/583 |
| 6,969,450 B2 | 11/2005 | Taniike | 204/403.01 |
| 6,969,451 B2 | 11/2005 | Shin | 204/412 |
| 6,973,706 B2 | 12/2005 | Say | 29/595 |
| 6,975,893 B2 | 12/2005 | Say | 600/347 |
| 6,977,032 B2 | 12/2005 | Hasegawa | 204/403.05 |
| 6,979,544 B2 | 12/2005 | Keen | 435/6 |
| 6,979,571 B2 | 12/2005 | Modzelewski | 436/164 |
| 6,982,027 B2 | 1/2006 | Yagi | 204/403.06 |
| 6,982,431 B2 | 1/2006 | Modlin et al. | |
| 6,983,176 B2 | 1/2006 | Gardner | 600/310 |
| 6,983,177 B2 | 1/2006 | Rule | 600/310 |
| 6,984,307 B2 | 1/2006 | Zweig | 205/777.5 |
| 6,986,777 B2 | 1/2006 | Kim | 606/182 |
| 6,986,869 B2 | 1/2006 | Tuohy | 422/56 |
| 6,988,996 B2 | 1/2006 | Roe | 600/584 |
| 6,989,243 B2 | 1/2006 | Yani | 435/14 |
| 6,989,891 B2 | 1/2006 | Braig | 356/39 |
| 6,990,365 B1 | 1/2006 | Parker | 600/328 |
| 6,990,366 B2 | 1/2006 | Say | 600/345 |
| 6,990,367 B2 | 1/2006 | Kiser | 600/345 |
| 6,990,849 B2 | 1/2006 | Bohm | 73/53.01 |
| 6,991,918 B2 | 1/2006 | Keith | 435/31 |
| 6,991,940 B2 | 1/2006 | Carroll | 436/514 |
| 6,994,825 B2 | 2/2006 | Haviland | 422/58 |
| 6,997,317 B2 | 2/2006 | Catelli | 206/438 |
| 6,997,343 B2 | 2/2006 | May | 221/232 |
| 6,997,344 B2 | 2/2006 | Brown | 221/258 |
| 6,997,936 B2 | 2/2006 | Marshall | 606/181 |
| 6,998,247 B2 | 2/2006 | Monfre | 435/14 |
| 6,998,248 B2 | 2/2006 | Yani | 435/14 |
| 6,999,810 B2 | 2/2006 | Berner | 600/345 |
| 7,001,343 B2 | 2/2006 | Erickson | 600/573 |
| 7,001,344 B2 | 2/2006 | Freeman | 600/583 |
| 7,003,337 B2 | 2/2006 | Harjunmaa | 600/316 |
| 7,003,340 B2 | 2/2006 | Say | 600/345 |
| 7,003,341 B2 | 2/2006 | Say | 600/345 |
| 7,004,928 B2 | 2/2006 | Aceti | 604/191 |
| 7,005,048 B1 | 2/2006 | Watanabe | 204/403.04 |
| 7,005,273 B2 | 2/2006 | Heller | 435/25 |
| 7,005,459 B2 | 2/2006 | Hekal | 523/102 |
| 7,005,857 B2 | 2/2006 | Stiene | 324/449 |
| 7,006,857 B2 | 2/2006 | Braig | 600/345 |
| 7,006,858 B2 | 2/2006 | Silver | 600/345 |
| 7,008,384 B2 | 3/2006 | Tapper | 600/573 |
| 7,010,432 B2 | 3/2006 | Kermani | 702/19 |
| 7,011,630 B2 | 3/2006 | Desai | 600/309 |
| 7,011,954 B2 | 3/2006 | Ouyang | 435/7.9 |
| 7,014,615 B2 | 3/2006 | Erickson | 600/573 |
| 7,015,262 B2 | 3/2006 | Leong | 523/205 |
| 7,016,713 B2 | 3/2006 | Gardner | 600/310 |
| 7,018,568 B2 | 3/2006 | Tierney | 252/511 |
| 7,018,848 B2 | 3/2006 | Douglas | 436/524 |
| 7,022,217 B2 | 4/2006 | Hodges | 205/777.5 |
| 7,022,218 B2 | 4/2006 | Taniike | 205/777.5 |
| 7,022,286 B2 | 4/2006 | Lemke | 422/67 |
| 7,024,236 B2 | 4/2006 | Ford | 600/345 |
| 7,024,248 B2 | 4/2006 | Penner | 607/60 |
| 7,024,399 B2 | 4/2006 | Sumner | 706/45 |
| 7,025,425 B2 | 4/2006 | Kovatchev | 300/365 |
| 7,025,774 B2 | 4/2006 | Freeman | 606/181 |
| 7,027,848 B2 | 4/2006 | Robinson | 600/310 |
| 7,029,444 B2 | 4/2006 | Shin | 600/365 |
| 7,033,322 B2 | 4/2006 | Silver | 600/486 |
| 7,033,371 B2 | 4/2006 | Alden | 606/181 |
| 7,039,560 B2 | 5/2006 | Kawatahara | 702/187 |
| 7,041,057 B1 | 5/2006 | Faupel | 600/365 |
| 7,041,063 B2 | 5/2006 | Abreu | 600/549 |
| 7,041,068 B2 | 5/2006 | Freeman | 600/583 |
| 7,041,254 B2 | 5/2006 | Haviland | 422/58 |
| 7,041,468 B2 | 5/2006 | Drucker | 435/14 |
| 7,043,287 B1 | 5/2006 | Khalil | 600/310 |
| 7,044,911 B2 | 5/2006 | Drinan | 600/300 |
| 7,045,054 B1 | 5/2006 | Buck | 205/778 |
| 7,045,097 B2 | 5/2006 | Kovacs | 422/82.08 |
| 7,045,310 B2 | 5/2006 | Buck | 435/7.93 |
| 7,045,361 B2 | 5/2006 | Heiss | 436/172 |
| 7,047,070 B2 | 5/2006 | Wilkinson | 604/20 |
| 7,047,795 B2 | 5/2006 | Sato | 73/64.56 |
| 7,049,130 B2 | 5/2006 | Carroll | 435/287.2 |
| 7,050,843 B2 | 5/2006 | Shartle | 600/345 |
| 7,051,495 B2 | 5/2006 | Lang | 53/475 |
| 7,052,268 B2 | 5/2006 | Powell | 425/542 |
| 7,052,591 B2 | 5/2006 | Gao | 204/490 |
| 7,052,652 B2 | 5/2006 | Zanzucchi | 422/82.05 |
| 7,052,864 B2 | 5/2006 | Durkop | 435/25 |
| 7,054,682 B2 | 5/2006 | Young | 604/20 |
| 7,054,759 B2 | 5/2006 | Fukunaga | 702/23 |
| D523,555 S | 6/2006 | Loerwald | D24/146 |
| 7,056,425 B2 | 6/2006 | Hasegawa | 204/403.04 |
| 7,056,495 B2 | 6/2006 | Roser | 424/45 |
| 7,058,437 B2 | 6/2006 | Buse | 600/347 |
| 7,060,059 B2 | 6/2006 | Keith | 604/504 |
| 7,060,192 B2 | 6/2006 | Yuzhakov | 216/11 |
| 7,061,593 B2 | 6/2006 | Braig | 356/39 |
| 7,063,234 B2 | 6/2006 | Giraud | 221/271 |
| 7,063,774 B2 | 6/2006 | Bhullar | 204/403.02 |
| 7,063,775 B2 | 6/2006 | Yamaoka | 204/403.06 |
| 7,063,776 B2 | 6/2006 | Huang | 204/403.14 |
| 7,066,884 B2 | 6/2006 | Custer | 600/309 |
| 7,066,885 B2 | 6/2006 | Erickson | 600/309 |
| 7,070,564 B2 | 7/2006 | Matzinger | 600/300 |
| 7,070,680 B2 | 7/2006 | Bae | 204/403.04 |
| 7,073,246 B2 | 7/2006 | Bhullar | 29/595 |
| 7,074,307 B2 | 7/2006 | Simpson | 204/403.04 |
| 7,074,308 B2 | 7/2006 | Mao | 204/403.14 |
| 7,077,328 B2 | 7/2006 | Krishnaswamy | 235/472.01 |
| 7,077,828 B2 | 7/2006 | Kuhr | 604/207 |
| 7,078,480 B2 | 7/2006 | Nagel | 530/322 |
| 7,081,188 B1 | 7/2006 | Cho | 204/403.04 |
| 7,083,712 B2 | 8/2006 | Morita | 205/775 |
| 7,086,277 B2 | 8/2006 | Tess | 73/53.01 |
| 7,087,149 B1 | 8/2006 | Muguruma | 205/778 |
| 7,090,764 B2 | 8/2006 | Iyengar | 205/775 |
| 7,096,053 B2 | 8/2006 | Loeb | 600/317 |
| 7,096,124 B2 | 8/2006 | Sterling | 702/23 |
| 7,097,631 B2 | 8/2006 | Trautman | 604/46 |
| 7,098,038 B2 | 8/2006 | Fukuoka | 436/164 |
| 7,103,578 B2 | 9/2006 | Beck | 705/75 |
| 7,105,066 B2 | 9/2006 | Schraga | 606/182 |

| Patent No. | Date | Name | Class |
|---|---|---|---|
| 7,107,253 B1 | 9/2006 | Sumner | 706/45 |
| 7,108,680 B2 | 9/2006 | Rohr | 604/151 |
| 7,108,778 B2 | 9/2006 | Simpson | 205/778 |
| 7,109,271 B2 | 9/2006 | Liu | 525/283 |
| 7,110,112 B2 | 9/2006 | Uchida | 356/364 |
| 7,110,803 B2 | 9/2006 | Shults | 600/347 |
| 7,112,265 B1 | 9/2006 | McAleer | 204/403.09 |
| 7,112,451 B2 | 9/2006 | Takahashi | 436/514 |
| 7,115,362 B2 | 10/2006 | Douglas | 435/4 |
| 7,118,351 B2 | 10/2006 | Effenhauser | 417/208 |
| 7,118,667 B2 | 10/2006 | Lee | 205/777.5 |
| 7,118,668 B1 | 10/2006 | Edelbrock | 205/777.5 |
| 7,118,916 B2 | 10/2006 | Matzinger | 436/34 |
| 7,118,919 B2 | 10/2006 | Yatscoff | 436/56 |
| 7,120,483 B2 | 10/2006 | Russell | 600/345 |
| 7,122,102 B2 | 10/2006 | Wogoman | 204/400 |
| 7,122,110 B2 | 10/2006 | Deng | 205/777.5 |
| 7,122,111 B2 | 10/2006 | Tokunaga | 205/792 |
| 7,125,481 B2 | 10/2006 | Musho | 205/775 |
| 7,129,038 B2 | 10/2006 | Gopalan | 435/4 |
| RE39,390 E | 11/2006 | Hasegawa | 204/403.09 |
| D531,725 S | 11/2006 | Loerwald | D24/146 |
| 7,131,342 B2 | 11/2006 | Hodges | 73/864.72 |
| 7,131,984 B2 | 11/2006 | Sato | 606/182 |
| 7,132,041 B2 | 11/2006 | Deng | 205/777.5 |
| 7,133,710 B2 | 11/2006 | Acosta | 600/316 |
| 7,134,999 B2 | 11/2006 | Brauker | 600/309 |
| 7,135,100 B1 | 11/2006 | Lau | 204/403.14 |
| 7,137,957 B2 | 11/2006 | Erickson | 600/573 |
| 7,138,041 B2 | 11/2006 | Su | 204/403.04 |
| 7,138,089 B2 | 11/2006 | Aitken | 422/82.01 |
| 7,141,058 B2 | 11/2006 | Briggs | 606/181 |
| 7,144,404 B2 | 12/2006 | Whitson | 606/181 |
| 7,144,485 B2 | 12/2006 | Hsu | 204/403.02 |
| 7,144,495 B2 | 12/2006 | Teodorezyk | 205/792 |
| 7,144,496 B2 | 12/2006 | Meserol | 205/792 |
| 7,147,825 B2 | 12/2006 | Matsuda | 422/58 |
| 7,150,755 B2 | 12/2006 | Levaughn | 606/181 |
| 7,150,975 B2 | 12/2006 | Tamada | 435/14 |
| 7,150,995 B2 | 12/2006 | Xie | 436/67 |
| 7,153,696 B2 | 12/2006 | Fukuoka | 436/164 |
| 7,155,371 B2 | 12/2006 | Kawatahara | 702/187 |
| 7,160,251 B2 | 1/2007 | Neel | 600/365 |
| 7,160,313 B2 | 1/2007 | Galloway | 606/167 |
| 7,160,678 B1 | 1/2007 | Kayyem et al. | |
| 7,163,616 B2 | 1/2007 | Vreeke | 205/777.5 |
| 7,166,074 B2 | 1/2007 | Reghabi | 600/365 |
| 7,167,734 B2 | 1/2007 | Khalil | 600/310 |
| 7,167,818 B2 | 1/2007 | Brown | 703/11 |
| 7,225,535 B2 | 6/2007 | Feldman et al. | |
| 7,226,461 B2 | 6/2007 | Boecker et al. | |
| 2001/0011157 A1 | 8/2001 | Latterell | 600/576 |
| 2001/0016682 A1 | 8/2001 | Berner | 600/345 |
| 2001/0017269 A1 | 8/2001 | Heller | 205/777.5 |
| 2001/0027328 A1 | 10/2001 | Lum | 606/186 |
| 2001/0054319 A1 | 12/2001 | Heller | 73/849 |
| 2002/0016606 A1 | 2/2002 | Moerman | 606/181 |
| 2002/0019748 A1 | 2/2002 | Brown | 705/2 |
| 2002/0025469 A1 | 2/2002 | Heller | 429/43 |
| 2002/0029058 A1 | 3/2002 | Levaughn | 606/181 |
| 2002/0040230 A1 | 4/2002 | Kuhr | 606/181 |
| 2002/0042090 A1 | 4/2002 | Heller | 435/14 |
| 2002/0044890 A1 | 4/2002 | Black | 422/56 |
| 2002/0052618 A1 | 5/2002 | Haar | 606/181 |
| 2002/0053523 A1 | 5/2002 | Liamos | 205/787 |
| 2002/0057993 A1 | 5/2002 | Maisey | 422/82.01 |
| 2002/0076349 A1 | 6/2002 | Aitken | 422/58 |
| 2002/0078091 A1 | 6/2002 | Vu | 707/513 |
| 2002/0081559 A1 | 6/2002 | Brown | 434/307 R |
| 2002/0081588 A1 | 6/2002 | Lumley-Woodyear | 435/6 |
| 2002/0084196 A1 | 7/2002 | Liamos | 205/792 |
| 2002/0087056 A1 | 7/2002 | Aceti | |
| 2002/0092612 A1 | 7/2002 | Davies | 156/292 |
| 2002/0120216 A1 | 8/2002 | Fritz | 600/583 |
| 2002/0120261 A1 | 8/2002 | Morris | 606/41 |
| 2002/0130042 A1 | 9/2002 | Moerman | 204/403.01 |
| 2002/0133377 A1 | 9/2002 | Brown | 705/3 |
| 2002/0136667 A1 | 9/2002 | Subramanian | 422/100 |
| 2002/0136863 A1 | 9/2002 | Subramanian | 428/156 |
| 2002/0137998 A1 | 9/2002 | Smart | 600/347 |
| 2002/0138040 A1 | 9/2002 | Flora | 604/116 |
| 2002/0148739 A2 | 10/2002 | Liamos | 205/787 |
| 2002/0160520 A1 | 10/2002 | Orloff | 436/72 |
| 2002/0161289 A1 | 10/2002 | Hopkins | 600/322 |
| 2002/0168290 A1 | 11/2002 | Yuzhakov | 422/56 |
| 2002/0176984 A1 | 11/2002 | Smart | 428/336 |
| 2002/0177761 A1 | 11/2002 | Orloff | 600/309 |
| 2002/0188224 A1 | 12/2002 | Roe | 600/584 |
| 2003/0018282 A1 | 1/2003 | Effenhauser | 600/583 |
| 2003/0018300 A1 | 1/2003 | Duchon | 604/164.01 |
| 2003/0028125 A1 | 2/2003 | Yuzhakov | |
| 2003/0028126 A1 | 2/2003 | List | 600/583 |
| 2003/0050537 A1 | 3/2003 | Wessel | 600/300 |
| 2003/0050573 A1 | 3/2003 | Kuhr | 600/567 |
| 2003/0050656 A1 | 3/2003 | Schraga | 606/182 |
| 2003/0060730 A1 | 3/2003 | Perez | 600/576 |
| 2003/0069753 A1 | 4/2003 | Brown | 705/2 |
| 2003/0073089 A1 | 4/2003 | Mauze | 435/6 |
| 2003/0073229 A1 | 4/2003 | Greenstein | 435/287.2 |
| 2003/0073931 A1 | 4/2003 | Boecker | 600/573 |
| 2003/0083685 A1 | 5/2003 | Freeman | 606/181 |
| 2003/0083686 A1 | 5/2003 | Freeman | 606/181 |
| 2003/0088160 A1 | 5/2003 | Halleck | 600/300 |
| 2003/0088191 A1 | 5/2003 | Freeman et al. | 600/583 |
| 2003/0089730 A1 | 5/2003 | May | 221/232 |
| 2003/0093010 A1 | 5/2003 | Essenpreis | 600/583 |
| 2003/0100040 A1 | 5/2003 | Bonnecaze | 435/14 |
| 2003/0106810 A1 | 6/2003 | Douglas | 205/777.5 |
| 2003/0109777 A1 | 6/2003 | Kloepfer | 600/367 |
| 2003/0111357 A1 | 6/2003 | Black | 205/775 |
| 2003/0113827 A1 | 6/2003 | Burkoth | 435/14 |
| 2003/0116447 A1 | 6/2003 | Sturridge | 205/777.5 |
| 2003/0135333 A1 | 7/2003 | Aceti | 702/31 |
| 2003/0139653 A1 | 7/2003 | Manser | 600/300 |
| 2003/0143113 A2 | 7/2003 | Yuzhakov | 422/56 |
| 2003/0144608 A1 | 7/2003 | Kojima | 600/583 |
| 2003/0144609 A1 | 7/2003 | Kennedy | 600/583 |
| 2003/0146110 A1 | 8/2003 | Karinka | 205/777.5 |
| 2003/0149348 A1 | 8/2003 | Raskas | 600/310 |
| 2003/0149377 A1 | 8/2003 | Erickson | 600/573 |
| 2003/0153900 A1 | 8/2003 | Aceti | 604/890.1 |
| 2003/0159944 A1 | 8/2003 | Pottgen | 205/777.5 |
| 2003/0163351 A1 | 8/2003 | Brown | 705/2 |
| 2003/0178322 A1 | 9/2003 | Iyengar | 205/775 |
| 2003/0191415 A1 | 10/2003 | Moerman | 600/584 |
| 2003/0195435 A1 | 10/2003 | Williams | 600/583 |
| 2003/0195540 A1 | 10/2003 | Moerman | 606/181 |
| 2003/0199744 A1 | 10/2003 | Buse | 600/347 |
| 2003/0199789 A1 | 10/2003 | Boecker | 600/575 |
| 2003/0199790 A1 | 10/2003 | Boecker | 600/576 |
| 2003/0199791 A1 | 10/2003 | Boecker | 600/576 |
| 2003/0199891 A1 | 10/2003 | Argauer | 606/181 |
| 2003/0199893 A1 | 10/2003 | Boecker | 606/181 |
| 2003/0199894 A1 | 10/2003 | Boecker | 606/181 |
| 2003/0199895 A1 | 10/2003 | Boecker | 606/181 |
| 2003/0199896 A1 | 10/2003 | Boecker | 606/181 |
| 2003/0199897 A1 | 10/2003 | Boecker | 606/181 |
| 2003/0199898 A1 | 10/2003 | Boecker | 606/181 |
| 2003/0199899 A1 | 10/2003 | Boecker | 606/181 |
| 2003/0199900 A1 | 10/2003 | Boecker | 606/181 |
| 2003/0199901 A1 | 10/2003 | Boecker | 606/181 |
| 2003/0199902 A1 | 10/2003 | Boecker | 606/181 |
| 2003/0199903 A1 | 10/2003 | Boecker | 606/181 |
| 2003/0199904 A1 | 10/2003 | Boecker | 606/181 |
| 2003/0199905 A1 | 10/2003 | Boecker | 606/181 |
| 2003/0199906 A1 | 10/2003 | Boecker | 606/181 |

| Pub. No. | Date | Inventor | Class |
|---|---|---|---|
| 2003/0199907 A1 | 10/2003 | Boecker | 606/181 |
| 2003/0199908 A1 | 10/2003 | Boecker | 606/181 |
| 2003/0199909 A1 | 10/2003 | Boecker | 606/181 |
| 2003/0199910 A1 | 10/2003 | Boecker | 606/181 |
| 2003/0199911 A1 | 10/2003 | Boecker | 606/181 |
| 2003/0199912 A1 | 10/2003 | Pugh | 606/182 |
| 2003/0201194 A1 | 10/2003 | Heller | 205/777.5 |
| 2003/0203352 A1 | 10/2003 | Haviland | 435/4 |
| 2003/0206828 A1 | 11/2003 | Bell | 422/44 |
| 2003/0208140 A1 | 11/2003 | Pugh | 600/584 |
| 2003/0212344 A1 | 11/2003 | Yuzhakov | 600/583 |
| 2003/0212345 A1 | 11/2003 | McAllister | 600/584 |
| 2003/0212346 A1 | 11/2003 | McAllister | 600/584 |
| 2003/0212347 A1 | 11/2003 | Sohrab | 600/584 |
| 2003/0212423 A1 | 11/2003 | Pugh | 606/181 |
| 2003/0212424 A1 | 11/2003 | Briggs | 606/181 |
| 2003/0212579 A1 | 11/2003 | Brown | 705/2 |
| 2003/0216767 A1 | 11/2003 | List | 606/181 |
| 2003/0217918 A1 | 11/2003 | Davies | 204/403.14 |
| 2003/0220552 A1 | 11/2003 | Reghabi | 600/365 |
| 2003/0220663 A1 | 11/2003 | Fletcher | 606/182 |
| 2003/0223906 A1 | 12/2003 | McAllister | 422/58 |
| 2003/0225317 A1 | 12/2003 | Schell | 600/300 |
| 2003/0225429 A1 | 12/2003 | Garthe | 606/182 |
| 2003/0225430 A1 | 12/2003 | Schraga | 606/182 |
| 2003/0228637 A1 | 12/2003 | Wang | 435/7.9 |
| 2003/0229514 A2 | 12/2003 | Brown | 705/2 |
| 2003/0232370 A1 | 12/2003 | Trifiro | 435/6 |
| 2003/0233055 A1 | 12/2003 | Erickson | 600/573 |
| 2003/0233112 A1 | 12/2003 | Alden et al. | 606/181 |
| 2003/0233113 A1 | 12/2003 | Alden et al. | 606/182 |
| 2004/0006285 A1 | 1/2004 | Douglas | 600/583 |
| 2004/0007585 A1 | 1/2004 | Griffith | 221/232 |
| 2004/0009100 A1 | 1/2004 | Simons | 422/102 |
| 2004/0010279 A1 | 1/2004 | Freeman | 606/182 |
| 2004/0015064 A1 | 1/2004 | Parsons | 600/347 |
| 2004/0019250 A1 | 1/2004 | Catelli | 600/1 |
| 2004/0019259 A1 | 1/2004 | Brown | 600/300 |
| 2004/0026243 A1 | 2/2004 | Davies | 204/403.14 |
| 2004/0030353 A1 | 2/2004 | Schmelzeisen-R | 606/201 |
| 2004/0031682 A1 | 2/2004 | Wilsey | 204/403.1 |
| 2004/0034318 A1 | 2/2004 | Fritz | 604/19 |
| 2004/0038045 A1 | 2/2004 | Smart | 428/446 |
| 2004/0039303 A1 | 2/2004 | Wurster | 600/584 |
| 2004/0039342 A1 | 2/2004 | Eppstein | 604/200 |
| 2004/0039407 A1 | 2/2004 | Schraga | 606/181 |
| 2004/0039408 A1 | 2/2004 | Abulhaj | 606/181 |
| 2004/0049219 A1 | 3/2004 | Briggs | 606/181 |
| 2004/0049220 A1 | 3/2004 | Boecker | 606/181 |
| 2004/0050694 A1 | 3/2004 | Yang | 204/403.02 |
| 2004/0054267 A1 | 3/2004 | Feldman | 604/316 |
| 2004/0055898 A1 | 3/2004 | Heller et al. | 205/777.5 |
| 2004/0059256 A1 | 3/2004 | Perez | 600/583 |
| 2004/0060818 A1 | 4/2004 | Feldman | 204/403.01 |
| 2004/0061841 A1 | 4/2004 | Black | 355/30 |
| 2004/0064068 A1 | 4/2004 | DeNuzzio | 600/583 |
| 2004/0087990 A1 | 5/2004 | Boecker | 606/181 |
| 2004/0092842 A1 | 5/2004 | Boecker | 600/575 |
| 2004/0092994 A1 | 5/2004 | Briggs | 606/181 |
| 2004/0092995 A1 | 5/2004 | Boecker | 606/181 |
| 2004/0096991 A1 | 5/2004 | Zhang | 436/518 |
| 2004/0098009 A1 | 5/2004 | Boecker | 606/181 |
| 2004/0098010 A1 | 5/2004 | Davison | 606/181 |
| 2004/0102803 A1 | 5/2004 | Boecker | 606/183 |
| 2004/0106855 A1 | 6/2004 | Brown | 600/301 |
| 2004/0106858 A1 | 6/2004 | Say | 600/345 |
| 2004/0106859 A1 | 6/2004 | Say | 600/345 |
| 2004/0106860 A1 | 6/2004 | Say | 600/345 |
| 2004/0106904 A1 | 6/2004 | Gonnelli | 604/173 |
| 2004/0106941 A1 | 6/2004 | Roe | 606/181 |
| 2004/0107116 A1 | 6/2004 | Brown | 705/2 |
| 2004/0115754 A1 | 6/2004 | Chang | 435/14 |
| 2004/0115831 A1 | 6/2004 | Meathrel | 436/514 |
| 2004/0116780 A1 | 6/2004 | Brown | 600/300 |
| 2004/0116829 A1 | 6/2004 | Raney | 600/573 |
| 2004/0117207 A1 | 6/2004 | Brown | 705/2 |
| 2004/0117208 A1 | 6/2004 | Brown | 705/2 |
| 2004/0117209 A1 | 6/2004 | Brown | 705/2 |
| 2004/0117210 A1 | 6/2004 | Brown | 705/2 |
| 2004/0122339 A1 | 6/2004 | Roe | |
| 2004/0127818 A1 | 7/2004 | Roe | 600/583 |
| 2004/0127819 A1 | 7/2004 | Roe | 600/583 |
| 2004/0127928 A1 | 7/2004 | Whitson | 606/181 |
| 2004/0127929 A1 | 7/2004 | Roe | 606/181 |
| 2004/0132167 A1 | 7/2004 | Rule | 435/287.1 |
| 2004/0133125 A1 | 7/2004 | Miyashita | 600/573 |
| 2004/0133127 A1 | 7/2004 | Roe | 600/583 |
| 2004/0137640 A1 | 7/2004 | Hirao | 436/514 |
| 2004/0138541 A1 | 7/2004 | Ward | 600/345 |
| 2004/0138588 A1 | 7/2004 | Saikley | 600/583 |
| 2004/0138688 A1 | 7/2004 | Giraud | 606/181 |
| 2004/0146958 A1 | 7/2004 | Bae | 435/14 |
| 2004/0154932 A1 | 8/2004 | Deng | 205/777.5 |
| 2004/0157017 A1 | 8/2004 | Mauze | 428/35.7 |
| 2004/0157149 A1 | 8/2004 | Hofmann | 430/131 |
| 2004/0157319 A1 | 8/2004 | Keen | 435/287.2 |
| 2004/0157338 A1 | 8/2004 | Burke | 436/147 |
| 2004/0157339 A1 | 8/2004 | Burke | 436/149 |
| 2004/0158137 A1 | 8/2004 | Eppstein | 600/347 |
| 2004/0158271 A1 | 8/2004 | Hamamoto | 606/181 |
| 2004/0161737 A1 | 8/2004 | Yang | 435/5 |
| 2004/0162473 A1 | 8/2004 | Sohrab | 600/345 |
| 2004/0162474 A1 | 8/2004 | Kiser | 600/345 |
| 2004/0162506 A1 | 8/2004 | Duchon | 600/583 |
| 2004/0162573 A1 | 8/2004 | Keheiri | 606/182 |
| 2004/0167383 A1 | 8/2004 | Kim | 600/365 |
| 2004/0171057 A1 | 9/2004 | Yang | 435/6 |
| 2004/0171968 A1 | 9/2004 | Katsuki | 600/583 |
| 2004/0172000 A1 | 9/2004 | Roe | 604/361 |
| 2004/0173472 A1 | 9/2004 | Jung | 205/777.5 |
| 2004/0173488 A1 | 9/2004 | Griffin | 206/363 |
| 2004/0176705 A1 | 9/2004 | Stevens | 600/584 |
| 2004/0176732 A1 | 9/2004 | Frazier | 604/345 |
| 2004/0178066 A1 | 9/2004 | Miyazaki | 204/403.01 |
| 2004/0178067 A1 | 9/2004 | Miyazaki | 204/403.1 |
| 2004/0178216 A1 | 9/2004 | Brickwood | 221/268 |
| 2004/0180379 A1 | 9/2004 | van Duyne | 435/7.1 |
| 2004/0182703 A1 | 9/2004 | Bell | 204/403.11 |
| 2004/0185568 A1 | 9/2004 | Matsumoto | 436/8 |
| 2004/0186359 A1 | 9/2004 | Beaudoin | 600/310 |
| 2004/0186394 A1 | 9/2004 | Roe | 600/598 |
| 2004/0186500 A1 | 9/2004 | Koilke | 606/181 |
| 2004/0193201 A1 | 9/2004 | Kim | 606/181 |
| 2004/0193377 A1 | 9/2004 | Brown | 702/19 |
| 2004/0194302 A1 | 10/2004 | Bhullar | 29/847 |
| 2004/0197231 A1 | 10/2004 | Katsuki | 422/68.1 |
| 2004/0197821 A1 | 10/2004 | Bauer | 437/7.1 |
| 2004/0199062 A1 | 10/2004 | Petersson | 600/316 |
| 2004/0199409 A1 | 10/2004 | Brown | 705/3 |
| 2004/0200720 A1 | 10/2004 | Musho | 204/403.01 |
| 2004/0200721 A1 | 10/2004 | Bhullar | 204/403.1 |
| 2004/0202576 A1 | 10/2004 | Aceti | 422/82.05 |
| 2004/0204662 A1 | 10/2004 | Perez | 600/583 |
| 2004/0206625 A1 | 10/2004 | Bhullar | 204/403.1 |
| 2004/0206636 A1 | 10/2004 | Hodges | 205/792 |
| 2004/0206658 A1 | 10/2004 | Hammerstedt | 206/524.1 |
| 2004/0209307 A1 | 10/2004 | Valkirs | 435/7.1 |
| 2004/0209350 A1 | 10/2004 | Sakata | 435/287.1 |
| 2004/0209354 A1 | 10/2004 | Mathies | 435/287.2 |
| 2004/0210279 A1 | 10/2004 | Gruzdev | 607/89 |
| 2004/0211666 A1 | 10/2004 | Pamidi | 204/403.01 |
| 2004/0214253 A1 | 10/2004 | Paek | 435/7.92 |
| 2004/0215224 A1 | 10/2004 | Sakata | 606/181 |
| 2004/0215225 A1 | 10/2004 | Nakayama | 606/182 |
| 2004/0216516 A1 | 11/2004 | Sato | 73/64.56 |
| 2004/0217019 A1 | 11/2004 | Cai | 205/792 |

| Pub. No. | Date | Name | Class |
|---|---|---|---|
| 2004/0219500 A1 | 11/2004 | Brown | 434/307 R |
| 2004/0219535 A1 | 11/2004 | Bell | 435/6 |
| 2004/0220456 A1 | 11/2004 | Eppstein | 600/309 |
| 2004/0220495 A1 | 11/2004 | Cahir | 600/562 |
| 2004/0220564 A1 | 11/2004 | Ho | 606/47 |
| 2004/0220603 A1 | 11/2004 | Rutynowski | 606/181 |
| 2004/0222092 A1 | 11/2004 | Musho | 204/401 |
| 2004/0224369 A1 | 11/2004 | Cai | 435/7.7 |
| 2004/0225230 A1 | 11/2004 | Liamos | 600/583 |
| 2004/0225311 A1 | 11/2004 | Levaughn | 606/181 |
| 2004/0225312 A1 | 11/2004 | Orloff | 606/182 |
| 2004/0230216 A1 | 11/2004 | Levaughn | 606/181 |
| 2004/0231984 A1 | 11/2004 | Lauks | 204/416 |
| 2004/0232009 A1 | 11/2004 | Okuda | 205/789 |
| 2004/0236250 A1 | 11/2004 | Hodges | 600/583 |
| 2004/0236251 A1 | 11/2004 | Roe | 600/583 |
| 2004/0236268 A1 | 11/2004 | Mitragotri | 604/20 |
| 2004/0236362 A1 | 11/2004 | Shraga | 606/181 |
| 2004/0238357 A1 | 12/2004 | Bhullar | 204/400 |
| 2004/0238358 A1 | 12/2004 | Forrow | 204/403 |
| 2004/0238359 A1 | 12/2004 | Ikeda | 204/403.1 |
| 2004/0241746 A1 | 12/2004 | Adlassnig | 435/7.1 |
| 2004/0242977 A1 | 12/2004 | Dosmann | 600/315 |
| 2004/0243164 A1 | 12/2004 | D'Agostino | 606/181 |
| 2004/0243165 A1 | 12/2004 | Koike | 606/181 |
| 2004/0245101 A1 | 12/2004 | Willner | 204/403 |
| 2004/0248282 A1 | 12/2004 | Sobha | 435/287.2 |
| 2004/0248312 A1 | 12/2004 | Vreeke | 436/95 |
| 2004/0249254 A1 | 12/2004 | Racchini | 600/347 |
| 2004/0249310 A1 | 12/2004 | Shartle | 600/583 |
| 2004/0249311 A1 | 12/2004 | Haar | 600/584 |
| 2004/0249405 A1 | 12/2004 | Watanabe | 606/181 |
| 2004/0249406 A1 | 12/2004 | Griffin | 606/182 |
| 2004/0251131 A1 | 12/2004 | Ueno | 204/403 |
| 2004/0253634 A1 | 12/2004 | Wang | 435/7.1 |
| 2004/0254434 A1 | 12/2004 | Goodnow | 600/365 |
| 2004/0254599 A1 | 12/2004 | Lipoma | 606/181 |
| 2004/0256228 A1 | 12/2004 | Huang | 204/434 |
| 2004/0256248 A1 | 12/2004 | Burke | 205/792 |
| 2004/0256685 A1 | 12/2004 | Chou | 257/414 |
| 2004/0258564 A1 | 12/2004 | Charlton | 422/58 |
| 2004/0260204 A1 | 12/2004 | Boecker | 600/584 |
| 2004/0260324 A1 | 12/2004 | Fukuzawa | 606/181 |
| 2004/0260325 A1 | 12/2004 | Kuhr | 606/181 |
| 2004/0260326 A1 | 12/2004 | Lipoma | 606/182 |
| 2004/0260511 A1 | 12/2004 | Burke | 702/182 |
| 2004/0267105 A1 | 12/2004 | Monfre | 600/344 |
| 2004/0267160 A9 | 12/2004 | Perez | 600/583 |
| 2004/0267229 A1 | 12/2004 | Moerman | 604/500 |
| 2004/0267299 A1 | 12/2004 | Kuriger | 606/181 |
| 2004/0267300 A1 | 12/2004 | Mace | 606/182 |
| 2005/0000806 A1 | 1/2005 | Hsieh | 203/403.1 |
| 2005/0000807 A1 | 1/2005 | Wang | 204/403.81 |
| 2005/0000808 A1 | 1/2005 | Cui | 203/403.14 |
| 2005/0003470 A1 | 1/2005 | Nelson | 435/14 |
| 2005/0004437 A1 | 1/2005 | Kaufmann | 600/300 |
| 2005/0004494 A1 | 1/2005 | Perez | 600/583 |
| 2005/0008537 A1 | 1/2005 | Mosolu | 422/56 |
| 2005/0008851 A1 | 1/2005 | Ezoe | 428/336 |
| 2005/0009191 A1 | 1/2005 | Swenson | 436/43 |
| 2005/0010090 A1 | 1/2005 | Acosta | 600/316 |
| 2005/0010093 A1 | 1/2005 | Ford | 600/345 |
| 2005/0010134 A1 | 1/2005 | Douglas | 600/573 |
| 2005/0010137 A1 | 1/2005 | Hodges | 600/583 |
| 2005/0010198 A1 | 1/2005 | Marchitto | 606/9 |
| 2005/0011759 A1 | 1/2005 | Moerman | 204/403.03 |
| 2005/0013731 A1 | 1/2005 | Burke | 422/56 |
| 2005/0014997 A1 | 1/2005 | Ruchti | 600/310 |
| 2005/0015020 A1 | 1/2005 | Levaughn | 600/583 |
| 2005/0016844 A1 | 1/2005 | Burke | 204/403.1 |
| 2005/0019212 A1 | 1/2005 | Bhullar | 422/56 |
| 2005/0019219 A1 | 1/2005 | Oshiman | 422/82.12 |
| 2005/0019805 A1 | 1/2005 | Groll | 435/6 |
| 2005/0019945 A1 | 1/2005 | Groll | 436/169 |
| 2005/0019953 A1 | 1/2005 | Groll | 436/514 |
| 2005/0021066 A1 | 1/2005 | Kuhr | 606/181 |
| 2005/0027181 A1 | 2/2005 | Goode et al. | |
| 2005/0027211 A1 | 2/2005 | Kuhr | 600/583 |
| 2005/0027562 A1 | 2/2005 | Brown | 705/2 |
| 2005/0033341 A1 | 2/2005 | Vreeke | 606/181 |
| 2005/0034983 A1 | 2/2005 | Chambers | 204/403.01 |
| 2005/0036020 A1 | 2/2005 | Li | 347/100 |
| 2005/0036146 A1 | 2/2005 | Braig | 356/246 |
| 2005/0036906 A1 | 2/2005 | Nakahara | 422/58 |
| 2005/0036909 A1 | 2/2005 | Erickson | 422/61 |
| 2005/0037482 A1 | 2/2005 | Braig | 435/287 |
| 2005/0038329 A1 | 2/2005 | Morris | 600/319 |
| 2005/0038330 A1 | 2/2005 | Jansen | 600/345 |
| 2005/0038463 A1 | 2/2005 | Davar | 606/181 |
| 2005/0038464 A1 | 2/2005 | Schraga | 606/182 |
| 2005/0038465 A1 | 2/2005 | Schraga | 606/182 |
| 2005/0038674 A1 | 2/2005 | Braig | 705/2 |
| 2005/0042766 A1 | 2/2005 | Ohman | 436/174 |
| 2005/0043894 A1 | 2/2005 | Fernandez | 702/19 |
| 2005/0043965 A1 | 2/2005 | Heller | 705/2 |
| 2005/0045476 A1 | 3/2005 | Neel | 204/403.2 |
| 2005/0049473 A1 | 3/2005 | Desai | 600/347 |
| 2005/0050859 A1 | 3/2005 | Coppeta | 53/471 |
| 2005/0054082 A1 | 3/2005 | Pachl | 435/287.2 |
| 2005/0059895 A1 | 3/2005 | Brown | 600/481 |
| 2005/0060194 A1 | 3/2005 | Brown | 705/2 |
| 2005/0067280 A1 | 3/2005 | Reid | 204/403.14 |
| 2005/0067737 A1 | 3/2005 | Rappin | 264/272.19 |
| 2005/0070771 A1 | 3/2005 | Rule | 600/316 |
| 2005/0070819 A1 | 3/2005 | Poux | 600/576 |
| 2005/0070945 A1 | 3/2005 | Schraga | 606/182 |
| 2005/0072670 A1 | 4/2005 | Hasegawa | 204/403.01 |
| 2005/0077176 A1 | 4/2005 | Hodges | 204/403.01 |
| 2005/0077584 A1 | 4/2005 | Uhland | 257/414 |
| 2005/0079542 A1 | 4/2005 | Cullen | 435/7.1 |
| 2005/0080652 A1 | 4/2005 | Brown | 705/2 |
| 2005/0085839 A1 | 4/2005 | Allen | 606/181 |
| 2005/0085840 A1 | 4/2005 | Yi | 606/182 |
| 2005/0086083 A1 | 4/2005 | Brown | 705/2 |
| 2005/0090754 A1 | 4/2005 | Wolf | 600/509 |
| 2005/0090850 A1 | 4/2005 | Toes | 606/182 |
| 2005/0096520 A1 | 5/2005 | Maekawa | 600/365 |
| 2005/0096565 A1 | 5/2005 | Chang | 600/584 |
| 2005/0096586 A1 | 5/2005 | Trautman | 604/46 |
| 2005/0096587 A1 | 5/2005 | Santini, Jr. | 604/66 |
| 2005/0096686 A1 | 5/2005 | Allen | 606/181 |
| 2005/0098431 A1 | 5/2005 | Hodges | 204/403.01 |
| 2005/0098432 A1 | 5/2005 | Grundel | 204/403.2 |
| 2005/0098433 A1 | 5/2005 | Grundel | 204/403.2 |
| 2005/0098434 A1 | 5/2005 | Grundel | 204/403.02 |
| 2005/0100880 A1 | 5/2005 | Chang | 435/4 |
| 2005/0101841 A9 | 5/2005 | Kaylor | 600/300 |
| 2005/0101979 A1 | 5/2005 | Alden | 606/181 |
| 2005/0101980 A1 | 5/2005 | Alden | 606/181 |
| 2005/0101981 A1 | 5/2005 | Alden | 606/181 |
| 2005/0103624 A1 | 5/2005 | Bhullar | 204/403.01 |
| 2005/0106713 A1 | 5/2005 | Phan | 435/287.2 |
| 2005/0109637 A1 | 5/2005 | Iyengar | 205/775 |
| 2005/0112782 A1 | 5/2005 | Buechler | 436/518 |
| 2005/0113658 A1 | 5/2005 | Jacobson | 600/342 |
| 2005/0113717 A1 | 5/2005 | Matzinger | 600/573 |
| 2005/0114062 A1 | 5/2005 | Davies | 702/104 |
| 2005/0114154 A1 | 5/2005 | Wolkowiez | 705/1 |
| 2005/0114444 A1 | 5/2005 | Brown | 709/203 |
| 2005/0118056 A1 | 6/2005 | Swanson | 423/23 |
| 2005/0119681 A1 | 6/2005 | Marshall | 606/181 |
| 2005/0123443 A1 | 6/2005 | Fujiwara | 422/58 |
| 2005/0123680 A1 | 6/2005 | Kang | 427/248.1 |
| 2005/0124869 A1 | 6/2005 | Hefti | 600/316 |
| 2005/0125017 A1 | 6/2005 | Kudrna | 606/181 |
| 2005/0125018 A1 | 6/2005 | Galloway | 606/181 |

| | | | | | | | |
|---|---|---|---|---|---|---|---|
| 2005/0125019 A1 | 6/2005 | Kudrna | 606/182 | 2005/0215923 A1 | 9/2005 | Wiegel | 600/573 |
| 2005/0126929 A1 | 6/2005 | Mansouri | 205/778 | 2005/0215925 A1 | 9/2005 | Chan | 600/583 |
| 2005/0130248 A1 | 6/2005 | Willner | 435/14 | 2005/0216046 A1 | 9/2005 | Yeoh | 606/181 |
| 2005/0130249 A1 | 6/2005 | Parris | 435/14 | 2005/0218024 A1 | 10/2005 | Lang | 206/438 |
| 2005/0130292 A1 | 6/2005 | Ahn | 435/287.1 | 2005/0221276 A1 | 10/2005 | Rozakis | 435/4 |
| 2005/0131286 A1 | 6/2005 | Parker | 600/328 | 2005/0221470 A1 | 10/2005 | Matsumoto | 435/287.1 |
| 2005/0131441 A1 | 6/2005 | Iio | 606/182 | 2005/0222599 A1 | 10/2005 | Czernecki | 606/182 |
| 2005/0133368 A1 | 6/2005 | Davies | 204/403.01 | 2005/0227372 A1 | 10/2005 | Khan | 436/514 |
| 2005/0136471 A1 | 6/2005 | Bhullar | 435/6 | 2005/0228242 A1 | 10/2005 | Kawamura | 600/300 |
| 2005/0136501 A1 | 6/2005 | Kuriger | 435/14 | 2005/0228883 A1 | 10/2005 | Brown | 709/224 |
| 2005/0136529 A1 | 6/2005 | Yang | 435/287 | 2005/0230252 A1 | 10/2005 | Tsai | 204/450 |
| 2005/0136550 A1 | 6/2005 | Yang | 436/514 | 2005/0230253 A1 | 10/2005 | Marquant | 204/451 |
| 2005/0137536 A1 | 6/2005 | Gonnelli | 604/264 | 2005/0232813 A1 | 10/2005 | Karmali | 422/58 |
| 2005/0143675 A1 | 6/2005 | Neel | 600/583 | 2005/0232815 A1 | 10/2005 | Ruhl | 422/66 |
| 2005/0143713 A1 | 6/2005 | Delmore | 604/506 | 2005/0234368 A1 | 10/2005 | Wong | 600/583 |
| 2005/0143771 A1 | 6/2005 | Stout | 606/181 | 2005/0234486 A1 | 10/2005 | Allen | 606/181 |
| 2005/0145490 A1 | 7/2005 | Shinno | 204/403 | 2005/0234487 A1 | 10/2005 | Shi | 600/181 |
| 2005/0145491 A1 | 7/2005 | Amano | 204/403 | 2005/0234488 A1 | 10/2005 | Allen | 606/181 |
| 2005/0145520 A1 | 7/2005 | Ilo | 206/365 | 2005/0234489 A1 | 10/2005 | Allen | 606/181 |
| 2005/0149088 A1 | 7/2005 | Fukuda | 606/181 | 2005/0234490 A1 | 10/2005 | Allen | 606/181 |
| 2005/0149089 A1 | 7/2005 | Trissel | 606/181 | 2005/0234491 A1 | 10/2005 | Allen | 606/181 |
| 2005/0150762 A1 | 7/2005 | Butters | 204/403 | 2005/0234492 A1 | 10/2005 | Tsai | 606/181 |
| 2005/0150763 A1 | 7/2005 | Butters | 204/403 | 2005/0234494 A1 | 10/2005 | Conway | 606/181 |
| 2005/0154277 A1 | 7/2005 | Ting | 600/407 | 2005/0234495 A1 | 10/2005 | Schraga | 606/181 |
| 2005/0154374 A1 | 7/2005 | Hunter | 604/890 | 2005/0235060 A1 | 10/2005 | Brown | 709/224 |
| 2005/0154410 A1 | 7/2005 | Conway | 606/181 | 2005/0239154 A1 | 10/2005 | Feldman | 435/14 |
| 2005/0154616 A1 | 7/2005 | Iliff | 705/3 | 2005/0239156 A1 | 10/2005 | Drucker | 435/14 |
| 2005/0158850 A1 | 7/2005 | Kubo | 435/287.2 | 2005/0239194 A1 | 10/2005 | Takahashi | 435/287.2 |
| 2005/0159656 A1 | 7/2005 | Hockersmith | 600/315 | 2005/0240090 A1 | 10/2005 | Ruchti | 600/316 |
| 2005/0159768 A1 | 7/2005 | Boehm | 606/182 | 2005/0240119 A1 | 10/2005 | Draudt | 600/583 |
| 2005/0164322 A1 | 7/2005 | Heller | 435/14 | 2005/0240207 A1 | 10/2005 | Marshall | 606/181 |
| 2005/0164329 A1 | 7/2005 | Wallace-Davis | 435/25 | 2005/0240778 A1 | 10/2005 | Saito | 713/186 |
| 2005/0165285 A1 | 7/2005 | Iliff | 600/300 | 2005/0245798 A1 | 11/2005 | Yamaguchi | 600/345 |
| 2005/0165393 A1 | 7/2005 | Eppstein | 606/41 | 2005/0245843 A1 | 11/2005 | Day | 600/583 |
| 2005/0165622 A1 | 7/2005 | Neel | 705/2 | 2005/0245844 A1 | 11/2005 | Mace | 600/583 |
| 2005/0169961 A1 | 8/2005 | Hunter | 424/423 | 2005/0245845 A1 | 11/2005 | Roe | 600/583 |
| 2005/0170448 A1 | 8/2005 | Burson | 435/14 | 2005/0245846 A1 | 11/2005 | Day | 600/583 |
| 2005/0171567 A1 | 8/2005 | DeHart | 606/181 | 2005/0245954 A1 | 11/2005 | Roe | 606/181 |
| 2005/0172021 A1 | 8/2005 | Brown | 709/224 | 2005/0245955 A1 | 11/2005 | Schraga | 606/181 |
| 2005/0172022 A1 | 8/2005 | Brown | 709/224 | 2005/0256534 A1 | 11/2005 | Alden | 606/182 |
| 2005/0173245 A1 | 8/2005 | Feldman | 204/403.01 | 2005/0258035 A1 | 11/2005 | Harding | 204/403.01 |
| 2005/0173246 A1 | 8/2005 | Hodges | 204/403.11 | 2005/0258036 A1 | 11/2005 | Harding | 204/403.01 |
| 2005/0175509 A1 | 8/2005 | Nakaminami | 422/82.03 | 2005/0258050 A1 | 11/2005 | Harding | 205/775 |
| 2005/0176084 A1 | 8/2005 | Burkoth | 435/14 | 2005/0265094 A1 | 12/2005 | Harding | 365/203 |
| 2005/0176133 A1 | 8/2005 | Miyashita | 435/287.1 | 2005/0276133 A1 | 12/2005 | Harding | 365/203 |
| 2005/0177071 A1 | 8/2005 | Nakayama | 600/583 | 2005/0278945 A1 | 12/2005 | Feldman | 29/830 |
| 2005/0177201 A1 | 8/2005 | Freeman | 607/46 | 2005/0279631 A1 | 12/2005 | Celentano | 204/403.01 |
| 2005/0177398 A1 | 8/2005 | Watanabe | 705/3 | 2005/0279647 A1 | 12/2005 | Beaty | 205/792 |
| 2005/0178218 A1 | 8/2005 | Montagu | 73/864.34 | 2005/0283094 A1 | 12/2005 | Thym | 600/583 |
| 2005/0181010 A1 | 8/2005 | Hunter | 424/423 | 2005/0284110 A1 | 12/2005 | Lang | 53/473 |
| 2005/0181497 A1 | 8/2005 | Salto | 435/287.1 | 2005/0284757 A1 | 12/2005 | Allen | 204/400 |
| 2005/0182307 A1 | 8/2005 | Currie | 600/300 | 2005/0287620 A1 | 12/2005 | Heller | 435/14 |
| 2005/0187439 A1 | 8/2005 | Blank | 600/310 | 2005/0288637 A1 | 12/2005 | Kuhr | 604/204 |
| 2005/0187444 A1 | 8/2005 | Hubner | 600/322 | 2005/0288698 A1 | 12/2005 | Matsumoto | 606/181 |
| 2005/0192488 A1 | 9/2005 | Bryenton | 600/301 | 2005/0288699 A1 | 12/2005 | Schraga | 606/181 |
| 2005/0196821 A1 | 9/2005 | Monfre | 435/14 | 2006/0000549 A1 | 1/2006 | Lang | 156/320 |
| 2005/0197666 A1 | 9/2005 | Raney | 606/181 | 2006/0003398 A1 | 1/2006 | Heller | 435/14 |
| 2005/0201897 A1 | 9/2005 | Zimmer | 422/82.05 | 2006/0004270 A1 | 1/2006 | Bedard | 600/316 |
| 2005/0202567 A1 | 9/2005 | Zanzucchi | 436/95 | 2006/0004271 A1 | 1/2006 | Peyser | 600/362 |
| 2005/0203358 A1 | 9/2005 | Monfre | 600/331 | 2006/0004272 A1 | 1/2006 | Shah | 600/365 |
| 2005/0203364 A1 | 9/2005 | Monfre | 600/365 | 2006/0006574 A1 | 1/2006 | Lang | 264/165 |
| 2005/0204939 A1 | 9/2005 | Krejci | 101/129 | 2006/0008389 A1 | 1/2006 | Sacherer | 422/102 |
| 2005/0205422 A1 | 9/2005 | Moser | 204/403.06 | 2006/0015129 A1 | 1/2006 | Shahrokni | 606/181 |
| 2005/0205816 A1 | 9/2005 | Hayenga | 251/61.1 | 2006/0016698 A1 | 1/2006 | Lee | 205/777.5 |
| 2005/0209515 A1 | 9/2005 | Hockersmith | 600/316 | 2006/0020228 A1 | 1/2006 | Fowler | 600/583 |
| 2005/0209564 A1 | 9/2005 | Bonner | 604/173 | 2006/0024774 A1 | 2/2006 | Zocchi | 435/14 |
| 2005/0209625 A1 | 9/2005 | Chan | 606/181 | 2006/0025662 A1 | 2/2006 | Buse | 600/347 |
| 2005/0211571 A1 | 9/2005 | Schulein | 205/777.5 | 2006/0029979 A1 | 2/2006 | Bai | 435/7.1 |
| 2005/0211572 A1 | 9/2005 | Buck | 205/778 | 2006/0029991 A1 | 2/2006 | Hagino | 435/14 |
| 2005/0214881 A1 | 9/2005 | Azarnia | 435/7.92 | 2006/0030028 A1 | 2/2006 | Nakaminami | 435/287.2 |
| 2005/0214892 A1 | 9/2005 | Kovatchev | 435/25 | 2006/0030788 A1 | 2/2006 | Wong | 600/583 |
| 2005/0215871 A1 | 9/2005 | Feldman | 600/309 | 2006/0034728 A1 | 2/2006 | Kloepfer | 422/68.1 |
| 2005/0215872 A1 | 9/2005 | Berner | 600/347 | 2006/0040333 A1 | 2/2006 | Zocchi | 435/14 |

| Pub. No. | Date | Name | Class |
|---|---|---|---|
| 2006/0047220 A1 | 3/2006 | Sakata | 600/583 |
| 2006/0047294 A1 | 3/2006 | Mori | 606/181 |
| 2006/0052723 A1 | 3/2006 | Roe | 600/583 |
| 2006/0052724 A1 | 3/2006 | Roe | 600/583 |
| 2006/0052809 A1 | 3/2006 | Karbowniczek | 606/181 |
| 2006/0052810 A1 | 3/2006 | Freeman | 606/181 |
| 2006/0058827 A1 | 3/2006 | Sakata | 606/181 |
| 2006/0058828 A1 | 3/2006 | Shi | 606/181 |
| 2006/0062852 A1 | 3/2006 | Holmes | 424/484 |
| 2006/0063988 A1 | 3/2006 | Schurman | 600/316 |
| 2006/0064035 A1 | 3/2006 | Wang | 600/583 |
| 2006/0079739 A1 | 4/2006 | Chen Wang | 600/300 |
| 2006/0079810 A1 | 4/2006 | Patel | 600/583 |
| 2006/0079811 A1 | 4/2006 | Roe | 600/583 |
| 2006/0079920 A1 | 4/2006 | Schraga | 606/181 |
| 2006/0081469 A1 | 4/2006 | Lee | 204/403.02 |
| 2006/0085020 A1 | 4/2006 | Freeman | 606/181 |
| 2006/0085137 A1 | 4/2006 | Bartkowiak | 702/19 |
| 2006/0086624 A1 | 4/2006 | Tapsak | 205/775 |
| 2006/0088945 A1 | 4/2006 | Douglas | 436/518 |
| 2006/0089566 A1 | 4/2006 | DeHart | 600/573 |
| 2006/0091006 A1 | 5/2006 | Wang | 204/403.02 |
| 2006/0094944 A1 | 5/2006 | Chuang | 600/347 |
| 2006/0094947 A1 | 5/2006 | Kovatchev | 600/365 |
| 2006/0094986 A1 | 5/2006 | Neel | 600/583 |
| 2006/0095061 A1 | 5/2006 | Trautman | 606/185 |
| 2006/0096859 A1 | 5/2006 | Lau | 204/403.14 |
| 2006/0099107 A1 | 5/2006 | Yamamoto | 422/57 |
| 2006/0099703 A1 | 5/2006 | Choi | 435/287.1 |
| 2006/0100542 A9 | 5/2006 | Wong | 600/583 |
| 2006/0100543 A1 | 5/2006 | Raney | 600/583 |
| 2006/0100654 A1 | 5/2006 | Fukuda | 606/181 |
| 2006/0100655 A1 | 5/2006 | Leong | 606/181 |
| 2006/0100656 A1 | 5/2006 | Olson | 606/181 |
| 2006/0106373 A1 | 5/2006 | Cahir | 606/9 |
| 2006/0108236 A1 | 5/2006 | Kasielke | 205/792 |
| 2006/0113187 A1 | 6/2006 | Deng | 204/403.01 |
| 2006/0115857 A1 | 6/2006 | Keen | 435/7.1 |
| 2006/0116562 A1 | 6/2006 | Acosta | 600/316 |
| 2006/0116704 A1 | 6/2006 | Ashby | 606/167 |
| 2006/0116705 A1 | 6/2006 | Schraga | 606/181 |
| 2006/0119362 A1 | 6/2006 | Kermani | 324/324 |
| 2006/0121547 A1 | 6/2006 | McIntire | 435/14 |
| 2006/0121625 A1 | 6/2006 | Clemens | 436/514 |
| 2006/0121759 A1 | 6/2006 | Kasai | 439/188 |
| 2006/0122099 A1 | 6/2006 | Aoki | 514/3 |
| 2006/0122536 A1 | 6/2006 | Haar | 600/581 |
| 2006/0129065 A1 | 6/2006 | Matsumoto | 600/583 |
| 2006/0129172 A1 | 6/2006 | Crossman | 606/181 |
| 2006/0129173 A1 | 6/2006 | Wilkinson | 606/181 |
| 2006/0134713 A1 | 6/2006 | Rylatt | 435/7.92 |
| 2006/0140457 A1 | 6/2006 | Simshauser | 382/124 |
| 2006/0144704 A1 | 7/2006 | Ghesquiere | 204/403.01 |
| 2006/0151323 A1 | 7/2006 | Cho | 204/403.04 |
| 2006/0155215 A1 | 7/2006 | Cha | 600/583 |
| 2006/0155316 A1 | 7/2006 | Perez | 606/181 |
| 2006/0155317 A1 | 7/2006 | List | 606/181 |
| 2006/0156796 A1 | 7/2006 | Burke | 73/61.44 |
| 2006/0157362 A1 | 7/2006 | Schraga | 206/363 |
| 2006/0161078 A1 | 7/2006 | Schraga | 600/583 |
| 2006/0161194 A1 | 7/2006 | Freeman | 606/185 |
| 2006/0166302 A1 | 7/2006 | Clarke | 435/25 |
| 2006/0167382 A1 | 7/2006 | Deshmukh | 600/583 |
| 2006/1051342 | 7/2006 | Yaguchi | 206/306 |
| 2006/0169599 A1 | 8/2006 | Feldman | 205/792 |
| 2006/0173254 A1 | 8/2006 | Acosta | 600/316 |
| 2006/0173255 A1 | 8/2006 | Acosta | 600/316 |
| 2006/0173379 A1 | 8/2006 | Rasch-Menges | 600/583 |
| 2006/0173380 A1 | 8/2006 | Hoenes | 600/583 |
| 2006/0173478 A1 | 8/2006 | Schraga | 606/181 |
| 2006/0175216 A1 | 8/2006 | Freeman | 206/363 |
| 2006/0178573 A1 | 8/2006 | Kermani | 600/347 |
| 2006/0178599 A1 | 8/2006 | Faupel | 600/578 |
| 2006/0178600 A1 | 8/2006 | Kennedy | 600/584 |
| 2006/0178686 A1 | 8/2006 | Schraga | 606/181 |
| 2006/0178687 A1 | 8/2006 | Freeman | 606/181 |
| 2006/0178688 A1 | 8/2006 | Freeman | 606/181 |
| 2006/0178689 A1 | 8/2006 | Freeman | 606/181 |
| 2006/0178690 A1 | 8/2006 | Freeman | 606/181 |
| 2006/0183871 A1 | 8/2006 | Ward | 525/464 |
| 2006/0183983 A1 | 8/2006 | Acosta | 600/316 |
| 2006/0184101 A1 | 8/2006 | Srinivasan | 604/68 |
| 2006/0188395 A1 | 8/2006 | Taniike | 422/57 |
| 2006/0189895 A1 | 8/2006 | Neel | 600/584 |
| 2006/0191787 A1 | 8/2006 | Wang | 204/400 |
| 2006/0195023 A1 | 8/2006 | Acosta | 600/316 |
| 2006/0195047 A1 | 8/2006 | Freeman | 600/583 |
| 2006/0195128 A1 | 8/2006 | Alden | 606/181 |
| 2006/0195129 A1 | 8/2006 | Freeman | 606/181 |
| 2006/0195130 A1 | 8/2006 | Freeman | 606/181 |
| 2006/0195131 A1 | 8/2006 | Freeman | 606/181 |
| 2006/0195132 A1 | 8/2006 | Freeman | 606/181 |
| 2006/0195133 A1 | 8/2006 | Freeman | 606/181 |
| 2006/0196031 A1 | 9/2006 | Hoenes | 29/432 |
| 2006/0196795 A1 | 9/2006 | Windus-Smith | 206/438 |
| 2006/0200044 A1 | 9/2006 | Freeman | 600/583 |
| 2006/0200045 A1 | 9/2006 | Roe | 600/583 |
| 2006/0200046 A1 | 9/2006 | Windus-Smith | 600/583 |
| 2006/0200181 A1 | 9/2006 | Fukuzawa | 606/181 |
| 2006/0200981 A1 | 9/2006 | Bhullar | 29/847 |
| 2006/0200982 A1 | 9/2006 | Bhullar | 29/847 |
| 2006/0204399 A1 | 9/2006 | Freeman | 422/58 |
| 2006/0205029 A1 | 9/2006 | Heller | 435/25 |
| 2006/0205060 A1 | 9/2006 | Kim | 435/287.2 |
| 2006/0206135 A1 | 9/2006 | Uehata | 606/181 |
| 2006/0211127 A1 | 9/2006 | Iwaki | 436/169 |
| 2006/0211927 A1 | 9/2006 | Acosta | 600/316 |
| 2006/0211931 A1 | 9/2006 | Blank | 600/344 |
| 2006/0219551 A1 | 10/2006 | Edelbrock | 204/403.14 |
| 2006/0222567 A1 | 10/2006 | Kloepfer | 422/68.1 |
| 2006/0224171 A1 | 10/2006 | Sakata | 606/181 |
| 2006/0224172 A1 | 10/2006 | Levaughn | 606/181 |
| 2006/0229532 A1 | 10/2006 | Wong | 600/583 |
| 2006/0229533 A1 | 10/2006 | Hoenes | 600/584 |
| 2006/0229651 A1 | 10/2006 | Marshall | 606/181 |
| 2006/0231396 A1 | 10/2006 | Yamaoka | 204/403.14 |
| 2006/0231418 A1 | 10/2006 | Harding | 205/775 |
| 2006/0231442 A1 | 10/2006 | Windus-Smith | 206/438 |
| 2006/0234369 A1 | 10/2006 | Sih | 435/287.1 |
| 2006/0235284 A1 | 10/2006 | Lee | 600/345 |
| 2006/0235454 A1 | 10/2006 | LeVaughn | 606/181 |
| 2006/0241517 A1 | 10/2006 | Fowler | 600/583 |
| 2006/0241666 A1 | 10/2006 | Briggs | 606/181 |
| 2006/0241667 A1 | 10/2006 | Freeman | 606/181 |
| 2006/0241668 A1 | 10/2006 | Schraga | 606/181 |
| 2006/0241669 A1 | 10/2006 | Stout | 606/182 |
| 2006/0247554 A1 | 11/2006 | Roe | 600/583 |
| 2006/0247555 A1 | 11/2006 | Harttig | 600/584 |
| 2006/0247670 A1 | 11/2006 | LeVaughn | 606/181 |
| 2006/0247671 A1 | 11/2006 | Levaughn | 606/182 |
| 2006/0259057 A1 | 11/2006 | Kim | 606/181 |
| 2006/0259058 A1 | 11/2006 | Schiff | 606/181 |
| 2006/0259060 A1 | 11/2006 | Whitson | 606/182 |
| 2006/0264718 A1 | 11/2006 | Ruchti | 600/310 |
| 2006/0264996 A1 | 11/2006 | Levaughn | 606/181 |
| 2006/0264997 A1 | 11/2006 | Colonna | 606/181 |
| 2006/0271083 A1 | 11/2006 | Boecker | 606/181 |
| 2006/0271084 A1 | 11/2006 | Schraga | 606/182 |
| 2006/0276724 A1 | 12/2006 | Freeman | 600/583 |
| 2006/0277048 A1 | 12/2006 | Kintzig | 704/275 |
| 2006/0278545 A1 | 12/2006 | Henning | 206/363 |
| 2006/0282109 A1 | 12/2006 | Jansen | 606/181 |
| 2006/0286620 A1 | 12/2006 | Werner | 435/14 |
| 2006/0287664 A1 | 12/2006 | Grage | 606/181 |
| 2006/0293577 A1 | 12/2006 | Morrison | 600/365 |
| 2007/0004989 A1 | 1/2007 | Dhillon | 600/583 |

| | | | | | | |
|---|---|---|---|---|---|---|
| 2007/0004990 | A1 | 1/2007 | Kistner ............. 600/583 | EP | 0685737 | 9/2002 |
| 2007/0007183 | A1 | 1/2007 | Schulat ............. 209/573 | EP | 0958495 | 11/2002 |
| 2007/0009381 | A1 | 1/2007 | Schulat ............. 422/58 | EP | 0937249 | 12/2002 |
| 2007/0010839 | A1 | 1/2007 | Galloway ........... 606/167 | EP | 0880692 | 1/2004 |
| 2007/0010841 | A1 | 1/2007 | Teo ................. 606/181 | EP | 01374770 | 1/2004 |
| 2007/0015978 | A1 | 1/2007 | Kanayama ........... 600/310 | EP | 1246688 | 5/2004 |
| 2007/0016079 | A1 | 1/2007 | Freeman ............. 600/476 | EP | 1502614 | 2/2005 |
| 2007/0016103 | A1 | 1/2007 | Calasso ............. 600/583 | GB | 2168815 | 6/1986 |
| 2007/0016104 | A1 | 1/2007 | Jansen .............. 600/583 | GB | 233936 A | 6/1999 |

FOREIGN PATENT DOCUMENTS

| | | | | | |
|---|---|---|---|---|---|
| | | | GB | 2335860 A | 10/1999 |
| | | | GB | 2335990 A | 10/1999 |
| DE | 29824204 | 10/2000 | WO | WO 80/01389 | 7/1980 |
| DE | 10032042 | 1/2002 | WO | WO 85/04089 | 9/1985 |
| DE | 10057832 | 2/2002 | WO | WO 86/07632 | 12/1986 |
| DE | 10057832 C1 | 2/2002 | WO | WO 91/09139 | 6/1991 |
| DE | 10142232 | 3/2003 | WO | WO 93/06979 | 4/1993 |
| DE | 10208575 C1 | 8/2003 | WO | WO 93/25898 | 12/1993 |
| DE | 10245721 | 12/2003 | WO | WO 94/27140 | 11/1994 |
| DE | 10361560 A1 | 7/2005 | WO | WO 94/29703 | 12/1994 |
| EP | 0199484 A2 | 10/1986 | WO | WO 94/29704 | 12/1994 |
| EP | 0289 269 | 11/1988 | WO | WO 94/29731 | 12/1994 |
| EP | 0320109 | 6/1989 | WO | WO 95/00662 | 1/1995 |
| EP | 0 364 208 A1 | 4/1990 | WO | WO 95/06240 | 3/1995 |
| EP | 0170375 | 5/1990 | WO | WO 95/10223 | 4/1995 |
| EP | 0136362 | 12/1990 | WO | WO 95/22597 | 8/1995 |
| EP | 0453283 | 10/1991 | WO | WO 96/30431 | 10/1996 |
| EP | 0263948 | 2/1992 | WO | WO 97/02359 | 1/1997 |
| EP | 0374355 | 6/1993 | WO | WO 97/02487 | 1/1997 |
| EP | 0351891 | 9/1993 | WO | WO 97/18464 | 5/1997 |
| EP | 0593096 | 4/1994 | WO | WO 97/30344 | 8/1997 |
| EP | 0415388 | 5/1995 | WO | WO 97/42882 | 11/1997 |
| EP | 0505494 | 7/1995 | WO | WO 97/45720 | 12/1997 |
| EP | 0359831 | 8/1995 | WO | WO 98/03431 | 1/1998 |
| EP | 0471986 | 10/1995 | WO | WO 98/19159 | 5/1998 |
| EP | 0368474 | 12/1995 | WO | WO 98/20332 | 5/1998 |
| EP | 0461601 | 12/1995 | WO | WO 98/20348 | 5/1998 |
| EP | 0429076 | 1/1996 | WO | WO 98/24366 | 6/1998 |
| EP | 0552223 | 7/1996 | WO | WO 98/24373 | 6/1998 |
| EP | 0735363 | 10/1996 | WO | WO 98/35225 | 8/1998 |
| EP | 0505504 | 3/1997 | WO | WO 99/03584 | 1/1999 |
| EP | 0406304 | 8/1997 | WO | WO 99/05966 | 2/1999 |
| EP | 0537761 | 8/1997 | WO | WO 99/07431 A1 | 2/1999 |
| EP | 0795601 | 9/1997 | WO | WO 99/13100 | 3/1999 |
| EP | 0562370 | 11/1997 | WO | WO 99/17854 | 4/1999 |
| EP | 0415393 | 12/1997 | WO | WO 99/18532 | 4/1999 |
| EP | 0560336 | 5/1998 | WO | WO 99/19507 | 4/1999 |
| EP | 0878 708 | 11/1998 | WO | WO 99/19717 | 4/1999 |
| EP | 0 898 936 A2 | 3/1999 | WO | WO 99/27483 | 6/1999 |
| EP | 0505475 | 3/1999 | WO | WO 99/27852 | 6/1999 |
| EP | 0901018 | 3/1999 | WO | WO 99/62576 | 12/1999 |
| EP | 0470649 | 6/1999 | WO | WO 99/64580 | 12/1999 |
| EP | 0 951 939 A2 | 10/1999 | WO | WO 00/06024 | 2/2000 |
| EP | 0847447 | 11/1999 | WO | WO 00/09184 | 2/2000 |
| EP | 0964059 | 12/1999 | WO | WO 00/11578 | 3/2000 |
| EP | 0969097 | 1/2000 | WO | WO 00/15103 | 3/2000 |
| EP | 1021950 | 7/2000 | WO | WO 00/17799 | 3/2000 |
| EP | 0894869 | 2/2001 | WO | WO 00/17800 | 3/2000 |
| EP | 1074832 | 2/2001 | WO | WO 00/18293 | 4/2000 |
| EP | 1093854 | 4/2001 | WO | WO 00/19346 | 4/2000 |
| EP | 1101443 | 5/2001 | WO | WO 00/30186 | 5/2000 |
| EP | 1114995 | 7/2001 | WO | WO 00/32097 | 6/2000 |
| EP | 0736607 | 8/2001 | WO | WO 00/32098 | 6/2000 |
| EP | 0874984 | 11/2001 | WO | WO 00/33236 | 6/2000 |
| EP | 0730037 | 12/2001 | WO | WO 00/39914 | 7/2000 |
| EP | 0636879 | 1/2002 | WO | WO 00/42422 | 7/2000 |
| EP | 01174083 | 1/2002 | WO | WO 00/44084 | 7/2000 |
| EP | 0851224 | 3/2002 | WO | WO 00/50771 | 8/2000 |
| EP | 0759553 | 5/2002 | WO | WO 00/60340 | 10/2000 |
| EP | 0856586 | 5/2002 | WO | WO 00/64022 | 10/2000 |
| EP | 0817809 | 7/2002 | WO | WO 00/67245 | 11/2000 |
| EP | 0872728 | 7/2002 | WO | WO 00/67268 | 11/2000 |
| EP | 0795748 | 8/2002 | WO | WO 00/72452 | 11/2000 |
| | | | WO | WO 01/00090 | 1/2001 |

| | | | | | | |
|---|---|---|---|---|---|---|
| WO | WO 01/15807 | 3/2001 | | WO | WO 03/094752 | 11/2003 |
| WO | WO 01/16578 A1 | 3/2001 | | WO | WO 03/101297 | 12/2003 |
| WO | WO 01/75433 | 3/2001 | | WO | WO 2004/008130 | 1/2004 |
| WO | WO 01/23885 | 4/2001 | | WO | WO 2004/022133 | 3/2004 |
| WO | WO 01/25775 | 4/2001 | | WO | WO 2004/026130 | 4/2004 |
| WO | WO 01/26813 | 4/2001 | | WO | WO 2004/040285 A2 | 5/2004 |
| WO | WO 01/33216 | 5/2001 | | WO | WO 2004/040287 A1 | 5/2004 |
| WO | WO 01/34029 | 5/2001 | | WO | WO 2004/040948 | 5/2004 |
| WO | WO 01/36955 | 5/2001 | | WO | WO 2004/041082 | 5/2004 |
| WO | WO 01/37174 | 5/2001 | | WO | WO 2004/054455 | 7/2004 |
| WO | WO 01/45014 A1 | 6/2001 | | WO | WO 2004/060174 | 7/2004 |
| WO | WO 01/40788 | 7/2001 | | WO | WO 2004/060446 | 7/2004 |
| WO | WO 01/57510 | 8/2001 | | WO | WO 2004/091693 | 10/2004 |
| WO | WO 01/64105 | 9/2001 | | WO | WO 2004/098405 | 11/2004 |
| WO | WO 01/66010 | 9/2001 | | WO | WO 2004/003147 | 12/2004 |
| WO | WO 01/69505 | 9/2001 | | WO | WO 2004/107964 | 12/2004 |
| WO | WO 01/72225 | 10/2001 | | WO | WO 2004/107975 | 12/2004 |
| WO | WO 01/73124 | 10/2001 | | WO | WO 2004/112602 | 12/2004 |
| WO | WO 01/73395 | 10/2001 | | WO | WO 2005/001418 | 1/2005 |
| WO | WO 01/89691 | 11/2001 | | WO | WO 2005/006939 | 1/2005 |
| WO | WO 02/00101 | 1/2002 | | WO | WO 2005/011774 | 2/2005 |
| WO | WO 02/02796 | 1/2002 | | WO | WO 2005/016125 | 2/2005 |
| WO | WO 02/08750 | 1/2002 | | WO | WO 2005/018425 | 3/2005 |
| WO | WO 02/08753 | 1/2002 | | WO | WO 2005/018430 | 3/2005 |
| WO | WO 02/08950 | 1/2002 | | WO | WO 2005/018454 | 3/2005 |
| WO | WO 02/18940 | 3/2002 | | WO | WO 2005/018709 | 3/2005 |
| WO | WO 02/21317 | 3/2002 | | WO | WO 2005/018710 | 3/2005 |
| WO | WO 02/25551 | 3/2002 | | WO | WO 2005/018711 | 3/2005 |
| WO | WO 02/32559 | 4/2002 | | WO | WO 2005/022143 | 3/2005 |
| WO | WO 02/41227 | 5/2002 | | WO | WO 2005/023088 | 3/2005 |
| WO | WO 02/41779 | 5/2002 | | WO | WO 2005/033659 | 4/2005 |
| WO | WO 02/44948 | 6/2002 | | WO | WO 2005/034720 | 4/2005 |
| WO | WO 02/059734 | 8/2002 | | WO | WO 2005/034721 | 4/2005 |
| WO | WO 02/069791 | 9/2002 | | WO | WO 2005/034741 | 4/2005 |
| WO | WO 02/077638 | 10/2002 | | WO | WO 2005/034778 | 4/2005 |
| WO | WO 02/100251 | 12/2002 | | WO | WO 2005/035017 | 4/2005 |
| WO | WO 02/100252 | 12/2002 | | WO | WO 2005/035018 | 4/2005 |
| WO | WO 02/100253 | 12/2002 | | WO | WO 2005/037095 | 4/2005 |
| WO | WO 02/100254 | 12/2002 | | WO | WO 2005/046477 | 5/2005 |
| WO | WO 02/100460 | 12/2002 | | WO | WO 2005/065399 | 7/2005 |
| WO | WO 02/100461 | 12/2002 | | WO | WO 2005/065414 | 7/2005 |
| WO | WO 02/101343 | 12/2002 | | WO | WO 2005/065415 | 7/2005 |
| WO | WO 02/101359 | 12/2002 | | WO | WO 2005/065545 A2 | 7/2005 |
| WO | WO 03/000321 | 1/2003 | | WO | WO 2005/072604 | 8/2005 |
| WO | WO 03/023389 | 3/2003 | | WO | WO 2005/084557 | 9/2005 |
| WO | WO 03/042691 | 5/2003 | | WO | WO 2005/116622 | 12/2005 |
| WO | WO 03/045557 | 6/2003 | | WO | WO 2005/119234 | 12/2005 |
| WO | WO 03/046542 | 6/2003 | | WO | WO 2005/121759 | 12/2005 |
| WO | WO 03/049609 | 6/2003 | | WO | WO 2006/001973 | 1/2006 |
| WO | WO 03/050534 | 6/2003 | | WO | WO 2006/011062 | 2/2006 |
| WO | WO 03/066128 | 8/2003 | | WO | WO 2006/013045 | 2/2006 |
| WO | WO 03/070099 | 8/2003 | | WO | WO 2006/027702 A2 | 3/2006 |
| WO | WO 03/071940 | 9/2003 | | WO | WO 2006/032391 | 3/2006 |
| WO | WO 03/088851 A1 | 10/2003 | | WO | WO 2006/072004 | 7/2006 |

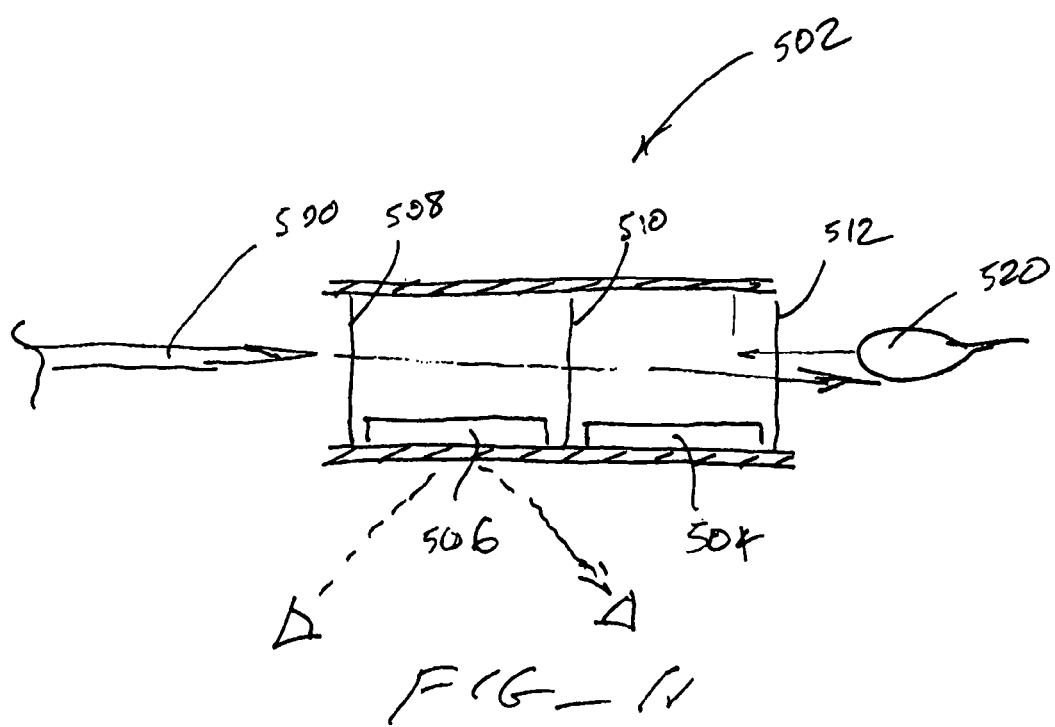
FIG_ N

METHOD AND APPARATUS FOR A POINT OF CARE DEVICE

BACKGROUND OF THE INVENTION

A. Technical Field

The technical field relates to using fluorescence or fluorescence lifetime decay of oxygen sensors to measure multiple parameters simultaneously such as pH, blood gases, electrolytes, immunoassay and hematology in a handheld miniaturized format using inexpensive electronics for illumination, detection, lancet actuation and data communication. Alternatively, electrochemical tests suitable for point of care testing can be employed.

B. Related Art

POC (point of care) testing is attractive because it rapidly delivers results to the medical practitioner and enables faster consultation with the patient enabling the practitioner to commence treatment sooner, perhaps leading towards improved patient outcomes. Relevant art includes the use of screening and monitoring diagnostics for early intervention, such as cardiac markers for early detection of angina, coronary artery occlusion and ruling out chest pain (triage). Examples of POC tests include blood chemistry such as glucose, lactate, electrolytes, as well as hematology, immuno-diagnostics, drugs of abuse, serum cholesterol, fecal occult blood test ("FOBT"), pregnancy, and ovulation. Examples of electrochemical Point of Care devices, which are hand, held are given by the i-STAT where electrochemical tests are carried out on a few drops of blood. Based on Microfabricated thin film electrodes, common tests include creatinine, or glucose on single cartridges, or combined tests such as sodium, potassium, hematocrit and hemoglobin on a single cartridge. Tests are combined on cartridges depending on the application e.g. blood gas panel etc. One disadvantage to this deployment of tests on panel specific cartridges is that in some cases several cartridges may be used to obtain complete POC information from the patient.

Current POC devices such as the i-STAT do not provide an integrated solution for patient self-testing for sample acquisition, testing, analysis and connectivity to remote centralized healthcare. Accordingly it is the object of this invention to provide a portable, highly integrated, multi-parameter measurement instrument where sampling is integrated with measurement processes from 1 µL of blood or less. Integration will allow the broad deployment of tests for a single sample acquisition step. This fully integrated blood sampling and measurement technology platform has been established for glucose spot monitoring, (WO 02/1000254 Lancet launching device integrated on to a blood sampling cartridge) in a multi-test format (100+ tests) employing an electronic blood-sampling device (WO 02/100460 Electric lancet actuator, WO 02/100251 Self optimizing lancing device) embedded within a glucose measurement instrument and a data management system (WO 02/101359 Integrated blood sampling and analysis system with multi use sampling module). Optical measurement of analytes provides the potential to monitor important clinical analytes for Point of Care applications. Fluorescent amplitude or lifetime decay optical measurements of glucose can be made with low-cost, low-power consumption components that are compatible with handheld instrumentation. These components include LED's, plastic optical elements, and CMOS or photodiode light detectors. The opportunity exists to carry out multiple measurements on the same sample to obtain more precise results or to analyze for components other than glucose (U.S. Pat. No. 6,379,969 Optical sensor for sensing multiple analytes)

These POC still use a body fluid sample. Obtaining such a sample using conventional lancing device can be painful. Early methods of lancing included piercing or slicing the skin with a needle or razor. Current methods utilize lancing devices that contain a multitude of spring, cam and mass actuators to drive the lancet. These include cantilever springs, diaphragms, coil springs, as well as gravity plumbs used to drive the lancet. The device may be held against the skin and mechanically triggered to ballistically launch the lancet. Unfortunately, the pain associated with each lancing event using known technology discourages patients from testing. In addition to vibratory stimulation of the skin as the driver impacts the end of a launcher stop, known spring based devices have the possibility of firing lancets that harmonically oscillate against the patient tissue, causing multiple strikes due to recoil. This recoil and multiple strikes of the lancet is one major impediment to patient compliance with a structured glucose monitoring regime.

Another impediment to uncomfortable patient experience of giving a blood sample is the lack of spontaneous blood flow generated by known lancing technology. In addition to the pain as discussed above, a patient may need more than one lancing event to obtain a blood sample since spontaneous blood generation is unreliable using known lancing technology. Thus the pain is multiplied by the number of attempts required by a patient to successfully generate spontaneous blood flow. Different skin thickness may yield different results in terms of pain perception, blood yield and success rate of obtaining blood between different users of the lancing device. Known devices poorly account for these skin thickness variations.

Measurement of glucose concentration is commonly based on the use of an enzyme such as glucose oxidase or glucose dehydrogenase. In such sensing schemes, glucose (substrate) is turned over by an enzyme layer resulting in change in the concentration of another species such as oxygen or hydrogen ion. The change in concentration of these species can be converted into some charge based or optical change at a transducer interface (sensing region). Alternatively, if the enzyme is electrically coupled to an inert electrode, such a reaction results in a change in electron flow at constant applied potential. Both types of transduction mechanisms are widely used in glucose sensing. In the former type of transduction scheme, the reaction zone can be decoupled from the sensing region. Thus, the reaction of the enzyme with the substrate can be brought about in one region and the concentration measurement can be done in another region. In the latter scheme, the enzymatic reaction has to occur in close proximity to the sensing region (electrode surface) for electrical coupling. Some devices may also include analyte detecting member for analyzing sample fluid. Unfortunately, the storage ability of these devices are limited due to the need for some of these elements to be stored in inert environments.

The current sensing technologies do not attempt the separate the reaction zone from the sensing region. One disadvantage of this approach is that the enzyme layer has to be placed in close proximity to the sensing element. This results in considerable difficulty in manufacturing and/or stabilizing the chemistries associated with enzymatic reaction and the transduction scheme. For example in the optical transduction schemes, an oxygen sensing layer such as a silicone rubber film doped with a flurophore, such as Ru Tris Diphenyl Phenanthroline, is coupled to the enzymatic layer containing glucose oxidase. The chemicals used in making these layers interfere with proper functioning of each other. There is often considerable reduction in the enzyme activity. The resultant sensors have limited dynamic range or limited shelf life or both.

SUMMARY OF THE INVENTION

The present invention provides solutions for at least some of the drawbacks discussed above. Specifically, some embodiments of the present invention provide an improved body fluid sampling device. The device may be used to perform a plurality of analyte tests on a single sample. At least some of these and other objectives described herein will be met by embodiments of the present invention.

In one embodiment, the present invention provides a multiple analyte detecting member and multiple lancet solution to measure analyte levels in the body. The invention may use a high-density analyte detecting member design of electrochemical or optical origin using multiple analyte detecting members to measure an analyte in a body fluid. It may use lancets of smaller size than known lancets. The device may be used for multiple lancing events without having to remove a disposable from the device.

The present invention provides solutions for at least some of the drawbacks discussed above. Specifically, some embodiments of the present invention provide an improved fluid sampling device. To improve shelf stable storage, devices and methods for decoupling enzyme layer from the sensing region may be provided. What is desired is a device and method that decouples the enzymatic reaction zone from the sensing region while providing appropriate contacting of the two with the sample to be analyzed. At least some of these and other objectives described herein will be met by embodiments of the present invention.

In one aspect of the present invention, the invention relates to using the electronic tissue penetration device to drive a penetrating member into tissue, causing two separated storage areas to be opened during actuation.

In one embodiment of the present invention, a method of body fluid sampling is provided. The method comprises moving a penetrating member at conforming to a selectable velocity profile or motion waveform; piercing a storage area having a sensing area; piercing another storage area having an enzyme area separate from the sensing area prior to piercing; and causing fluid to first flow to the enzyme area and then to the sensing area. The method may further comprise storing said enzyme area in an inert environment different from an environment for the sensing area.

The system may further comprise means for coupling the force generator with one of the penetrating members.

The system may further comprise a penetrating member sensor positioned to monitor a penetrating member coupled to the force generator, the penetrating member sensor configured to provide information relative to a depth of penetration of a penetrating member through a skin surface.

The depth of penetration may be about 100 to 2500 microns.

The depth of penetration may be about 500 to 750 microns.

The depth of penetration may be, in this nonlimiting example, no more than about 1000 microns beyond a stratum corneum thickness of a skin surface.

The depth of penetration may be no more than about 500 microns beyond a stratum corneum thickness of a skin surface.

The depth of penetration may be no more than about 300 microns beyond a stratum corneum thickness of a skin surface.

The depth of penetration may be less than a sum of a stratum corneum thickness of a skin surface and 400 microns.

The penetrating member sensor may be further configured to control velocity of a penetrating member.

The active penetrating member may move along a substantially linear path into the tissue.

The active penetrating member may move along an at least partially curved path into the tissue.

The driver may be a voice coil drive force generator.

The driver may be a rotary voice coil drive force generator.

The penetrating member sensor may be coupled to a processor with control instructions for the penetrating member driver.

The processor may include a memory for storage and retrieval of a set of penetrating member profiles utilized with the penetrating member driver.

The processor may be utilized to monitor position and speed of a penetrating member as the penetrating member moves in a first direction.

The processor may be utilized to adjust an application of force to a penetrating member to achieve a desired speed of the penetrating member.

The processor may be utilized to adjust an application of force to a penetrating member when the penetrating member contacts a target tissue so that the penetrating member penetrates the target tissue within a desired range of speed.

The processor may be utilized to monitor position and speed of a penetrating member as the penetrating member moves in the first direction toward a target tissue, wherein the application of a launching force to the penetrating member is controlled based on position and speed of the penetrating member.

The processor may be utilized to control a withdraw force to the penetrating member so that the penetrating member moves in a second direction away from the target tissue.

In the first direction, the penetrating member may move toward the target tissue at a speed that is different than a speed at which the penetrating member moves away from the target tissue.

In the first direction the penetrating member may move toward the target tissue at a speed that is greater than a speed at which the penetrating member moves away from the target tissue.

The speed of a penetrating member in the first direction may be the range of about 2.0 to 10.0 m/sec.

The average velocity of the penetrating member during a tissue penetration stroke in the first direction may be about 100 to about 1000 times greater than the average velocity of the penetrating member during a withdrawal stroke in a second direction.

A further understanding of the nature and advantages of the invention will become apparent by reference to the remaining portions of the specification and drawings.

BRIEF DESCRIPTION OF THE DRAWINGS

FIG. 11 shows one embodiment of method for preparing fluid for measurement.

DESCRIPTION OF THE SPECIFIC EMBODIMENTS

The present invention provides a solution for body fluid sampling. Specifically, some embodiments of the present invention provides a method for improving spontaneous blood generation. Some embodiments of the present invention provide an improved body fluid sampling device. For some embodiments of these penetrating member drivers, the invention relates to a new contact point algorithm that is run immediately before the actual lance event. At least some of these and other objectives described herein will be met by embodiments of the present invention.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a chamber" may include multiple chambers, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for analyzing a blood sample, this means that the analysis feature may or may not be present, and, thus, the description includes structures wherein a device possesses the analysis feature and structures wherein the analysis feature is not present.

Figure 1:
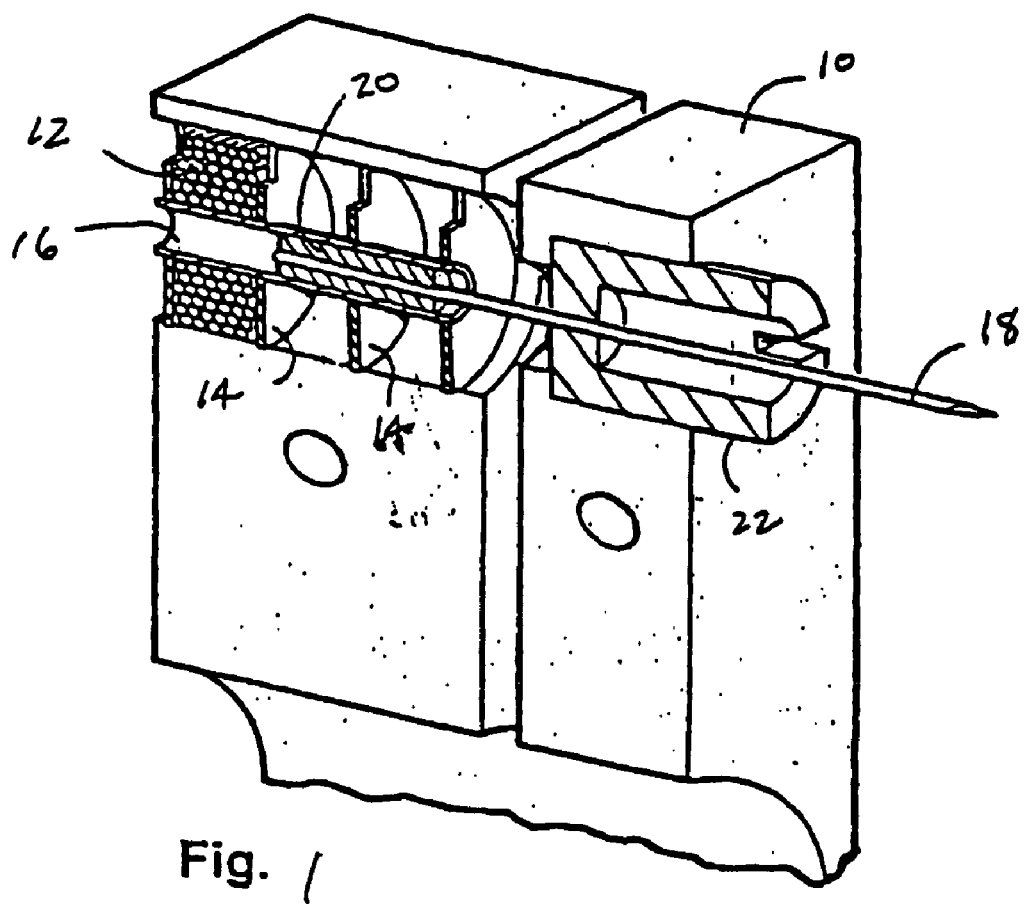
FIG. 1 illustrates an embodiment of a controllable force driver in the form of a cylindrical electric penetrating member driver using a coiled solenoid-type configuration.

The present invention may be used with a variety of different penetrating member drivers. It is contemplated that these penetrating member drivers may be spring based, solenoid based, magnetic driver based, nanomuscle based, or based on any other mechanism useful in moving a penetrating member along a path into tissue. It should be noted that the present invention is not limited by the type of driver used with the penetrating member feed mechanism. One suitable penetrating member driver for use with the present invention is shown in FIG. 1. This is an embodiment of a solenoid type electromagnetic driver that is capable of driving an iron core or slug mounted to the penetrating member assembly using a direct current (DC) power supply. The electromagnetic driver includes a driver coil pack that is divided into three separate coils along the path of the penetrating member, two end coils and a middle coil. Direct current is alternated to the coils to advance and retract the penetrating member. Although the driver coil pack is shown with three coils, any suitable number of coils may be used, for example, 4, 5, 6, 7 or more coils may be used.

Referring to the embodiment of FIG. 1, the stationary iron housing 10 may contain the driver coil pack with a first coil 12 flanked by iron spacers 14 which concentrate the magnetic flux at the inner diameter creating magnetic poles. The inner insulating housing 16 isolates the penetrating member 18 and iron core 20 from the coils and provides a smooth, low friction guide surface. The penetrating member guide 22 further centers the penetrating member 18 and iron core 20. The penetrating member 18 is protracted and retracted by alternating the current between the first coil 12, the middle coil, and the third coil to attract the iron core 20. Reversing the coil sequence and attracting the core and penetrating member back into the housing retracts the penetrating member. The penetrating member guide 22 also serves as a stop for the iron core 20 mounted to the penetrating member 18.

Figure 2A:
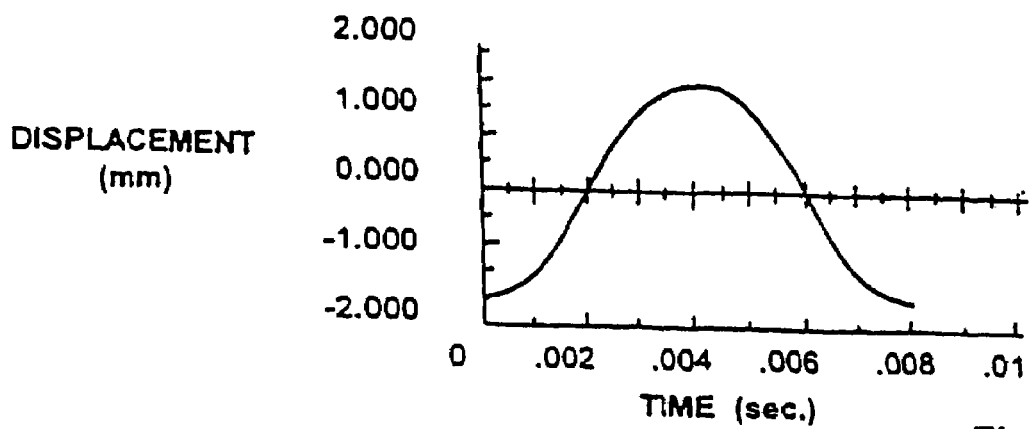
FIG. 2A illustrates a displacement over time profile of a penetrating member driven by a harmonic spring/mass system.
Figure 2B:
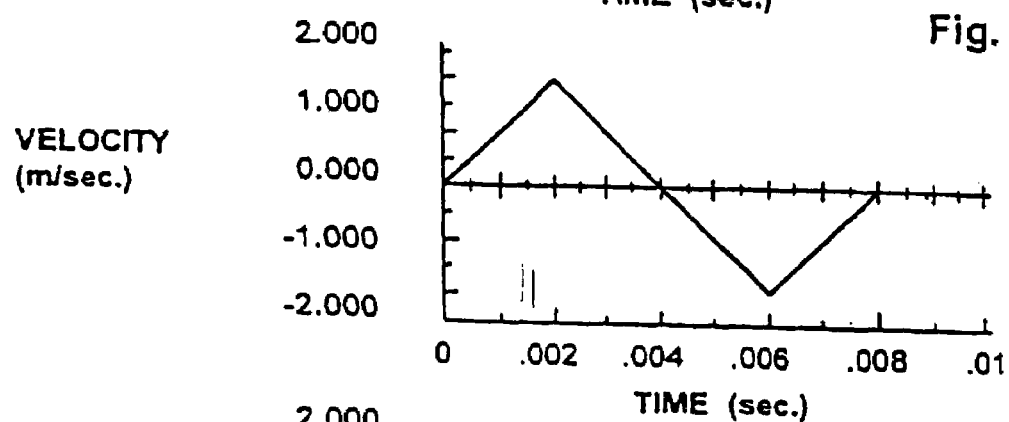
FIG. 2B illustrates the velocity over time profile of a penetrating member driver by a harmonic spring/mass system.
Figure 2C:
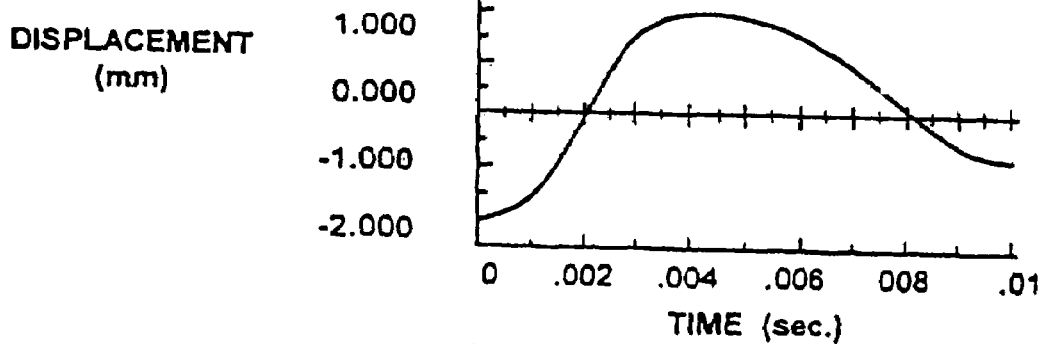
FIG. 2C illustrates a displacement over time profile of an embodiment of a controllable force driver.
Figure 2D:
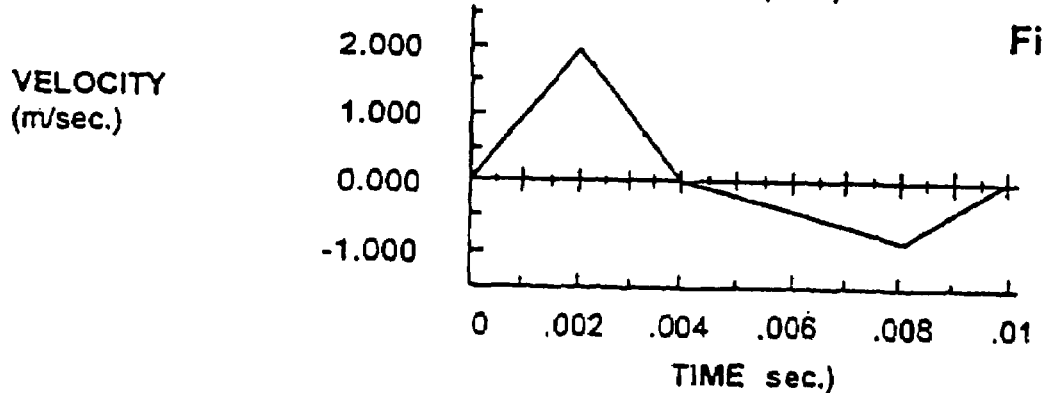
FIG. 2D illustrates a velocity over time profile of an embodiment of a controllable force driver.
Figure 3:
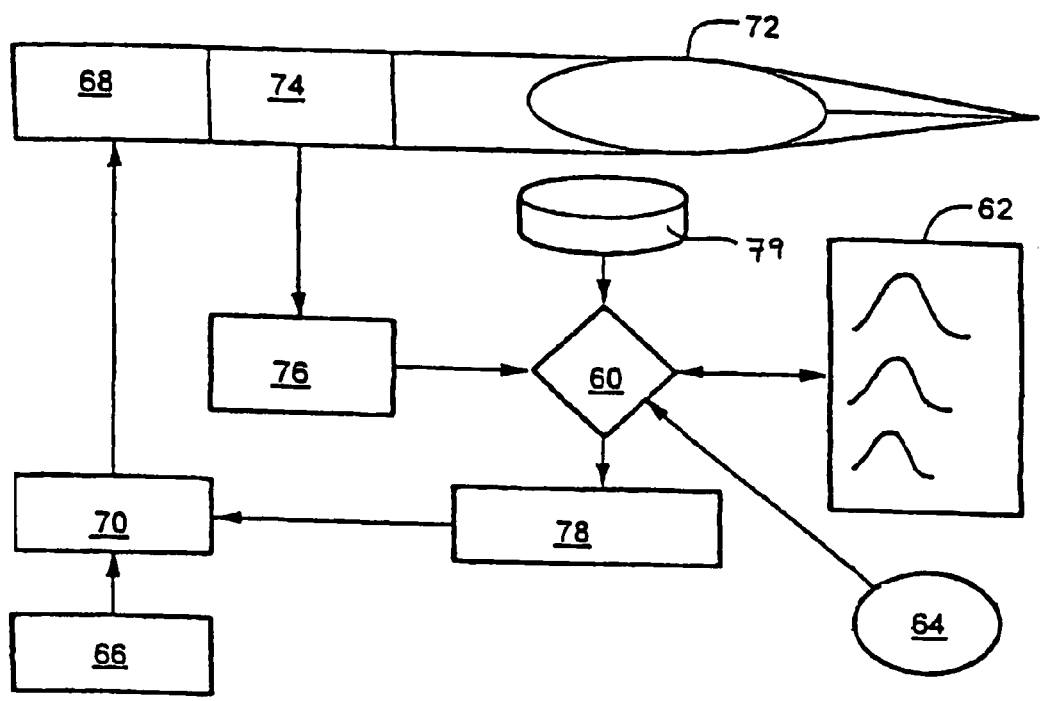
FIG. 3 is a diagrammatic view illustrating a controlled feed-back loop.

As discussed above, tissue penetration devices which employ spring or cam driving methods have a symmetrical or nearly symmetrical actuation displacement and velocity profiles on the advancement and retraction of the penetrating member as shown in FIGS. 2 and 3. In most of the available lancet devices, once the launch is initiated, the stored energy determines the velocity profile until the energy is dissipated. Controlling impact, retraction velocity, and dwell time of the penetrating member within the tissue can be useful in order to achieve a high success rate while accommodating variations in skin properties and minimize pain. Advantages can be achieved by taking into account of the fact that tissue dwell time is related to the amount of skin deformation as the penetrating member tries to puncture the surface of the skin and variance in skin deformation from patient to patient based on skin hydration.

In this embodiment, the ability to control velocity and depth of penetration may be achieved by use of a controllable force driver where feedback is an integral part of driver control. Such drivers can control either metal or polymeric penetrating members or any other type of tissue penetration element. The dynamic control of such a driver is illustrated in FIG. 2C which illustrates an embodiment of a controlled displacement profile and FIG. 2D which illustrates an embodiment of a the controlled velocity profile. These are compared to FIGS. 2A and 2B, which illustrate embodiments of displacement and velocity profiles, respectively, of a harmonic spring/mass powered driver. Reduced pain can be achieved by using impact velocities of greater than about 2 m/s entry of a tissue penetrating element, such as a lancet, into tissue. Other suitable embodiments of the penetrating member driver are described in commonly assigned, copending U.S. patent application Ser. No. 10/127,395, filed Apr. 19, 2002 and previously incorporated herein.

FIG. 3 illustrates the operation of a feedback loop using a processor 60. The processor 60 stores profiles 62 in non-volatile memory. A usher inputs information 64 about the desired circumstances or parameters for a lancing event. The processor 60 selects a driver profile 62 from a set of alternative driver profiles that have been preprogrammed in the processor 60 based on typical or desired tissue penetration device performance determined through testing at the factory or as programmed in by the operator. The processor 60 may customize by either scaling or modifying the profile based on additional user input information 64. Once the processor has chosen and customized the profile, the processor 60 is ready to modulate the power from the power supply 66 to the penetrating member driver 68 through an amplifier 70. The processor 60 may measure the location of the penetrating member 72 using a position sensing mechanism 74 through an analog to digital converter 76 linear encoder or other such transducer. Examples of position sensing mechanisms have been described in the embodiments above and may be found in the specification for commonly assigned, copending U.S. patent application Ser. No. 10/127,395, filed Apr. 19, 2002 and previously incorporated herein. The processor 60 calculates the movement of the penetrating member by comparing the actual profile of the penetrating member to the predetermined profile. The processor 60 modulates the power to the penetrating member driver 68 through a signal generator 78, which may control the amplifier 70 so that the actual velocity profile of the penetrating member does not exceed the predetermined profile by more than a preset error limit. The error limit is the accuracy in the control of the penetrating member.

After the lancing event, the processor 60 can allow the user to rank the results of the lancing event. The processor 60 stores these results and constructs a database 80 for the individual user. Using the database 79, the processor 60 calculates the profile traits such as degree of painlessness, success rate, and blood volume for various profiles 62 depending on user input information 64 to optimize the profile to the individual user for subsequent lancing cycles. These profile traits depend on the characteristic phases of penetrating member advancement and retraction. The processor 60 uses these calculations to optimize profiles 62 for each user. In addition to user input information 64, an internal clock allows storage in the database 79 of information such as the time of day to generate a time stamp for the lancing event and the time between lancing events to anticipate the user's diurnal needs. The database stores information and statistics for each user and each profile that particular user uses.

In addition to varying the profiles, the processor 60 can be used to calculate the appropriate penetrating member diameter and geometry suitable to realize the blood volume required by the user. For example, if the user requires about 1-5 microliter volume of blood, the processor 60 may select a 200 micron diameter penetrating member to achieve these results. For each class of lancet, both diameter and lancet tip geometry, is stored in the processor 60 to correspond with upper and lower limits of attainable blood volume based on the predetermined displacement and velocity profiles.

The lancing device is capable of prompting the user for information at the beginning and the end of the lancing event to more adequately suit the user. The goal is to either change to a different profile or modify an existing profile. Once the profile is set, the force driving the penetrating member is varied during advancement and retraction to follow the profile. The method of lancing using the lancing device comprises selecting a profile, lancing according to the selected profile, determining lancing profile traits for each characteristic phase of the lancing cycle, and optimizing profile traits for subsequent lancing events.

Figure 4:
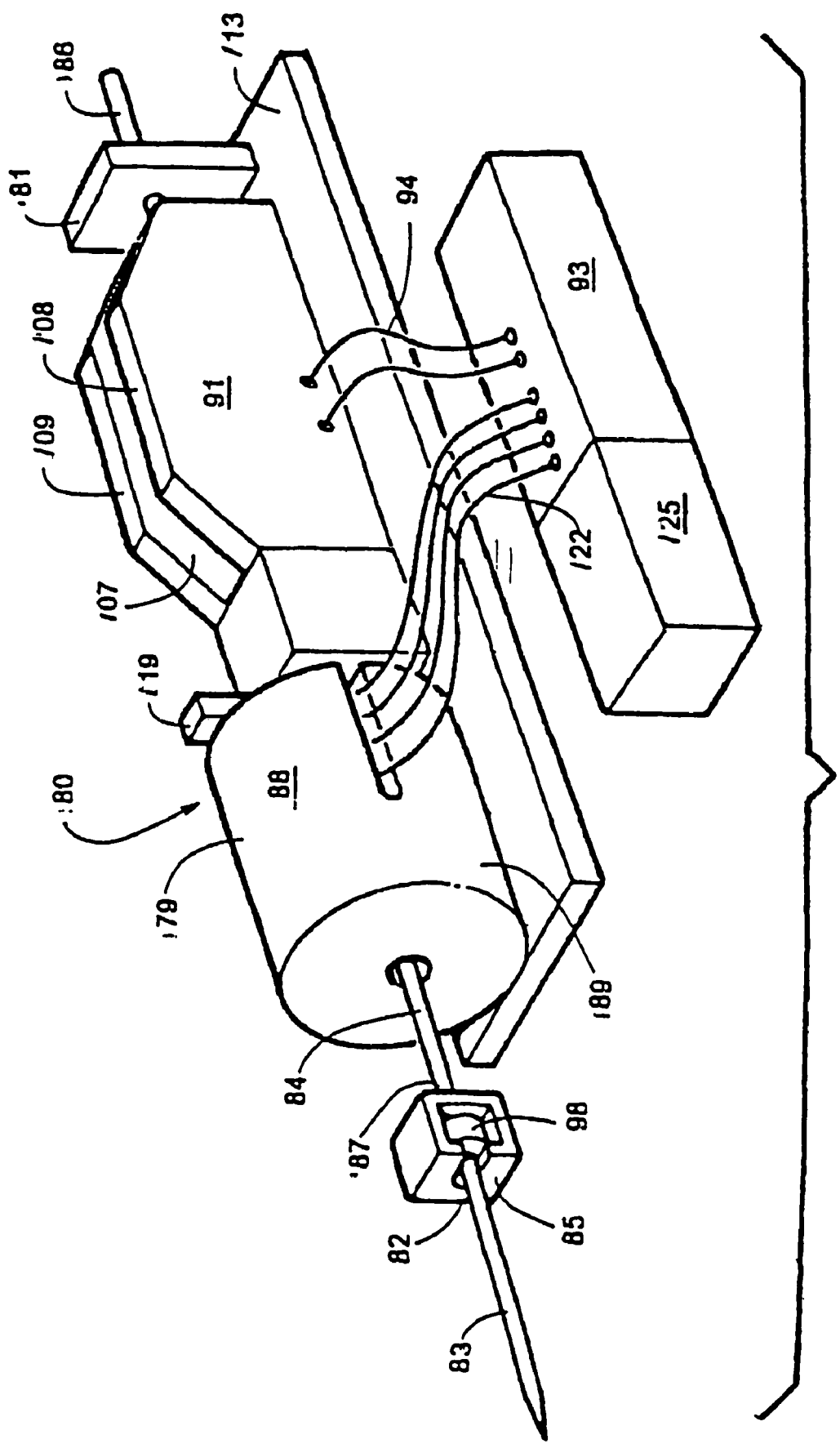
FIG. 4 is a perspective view of a tissue penetration device having features of the invention.

FIG. 4 illustrates an embodiment of a tissue penetration device, more specifically, a lancing device 80 that includes a controllable driver 179 coupled to a tissue penetration element. The lancing device 80 has a proximal end 81 and a distal end 82. At the distal end 82 is the tissue penetration element in the form of a penetrating member 83, which is coupled to an elongate coupler shaft 84 by a drive coupler 85. The elongate coupler shaft 84 has a proximal end 86 and a distal end 87. A driver coil pack 88 is disposed about the elongate coupler shaft 84 proximal of the penetrating member 83. A position sensor 91 is disposed about a proximal portion 92 of the elongate coupler shaft 84 and an electrical conductor 94 electrically couples a processor 93 to the position sensor 91. The elongate coupler shaft 84 driven by the driver coil pack 88 controlled by the position sensor 91 and processor 93 form the controllable driver, specifically, a controllable electromagnetic driver.

Figure 5:
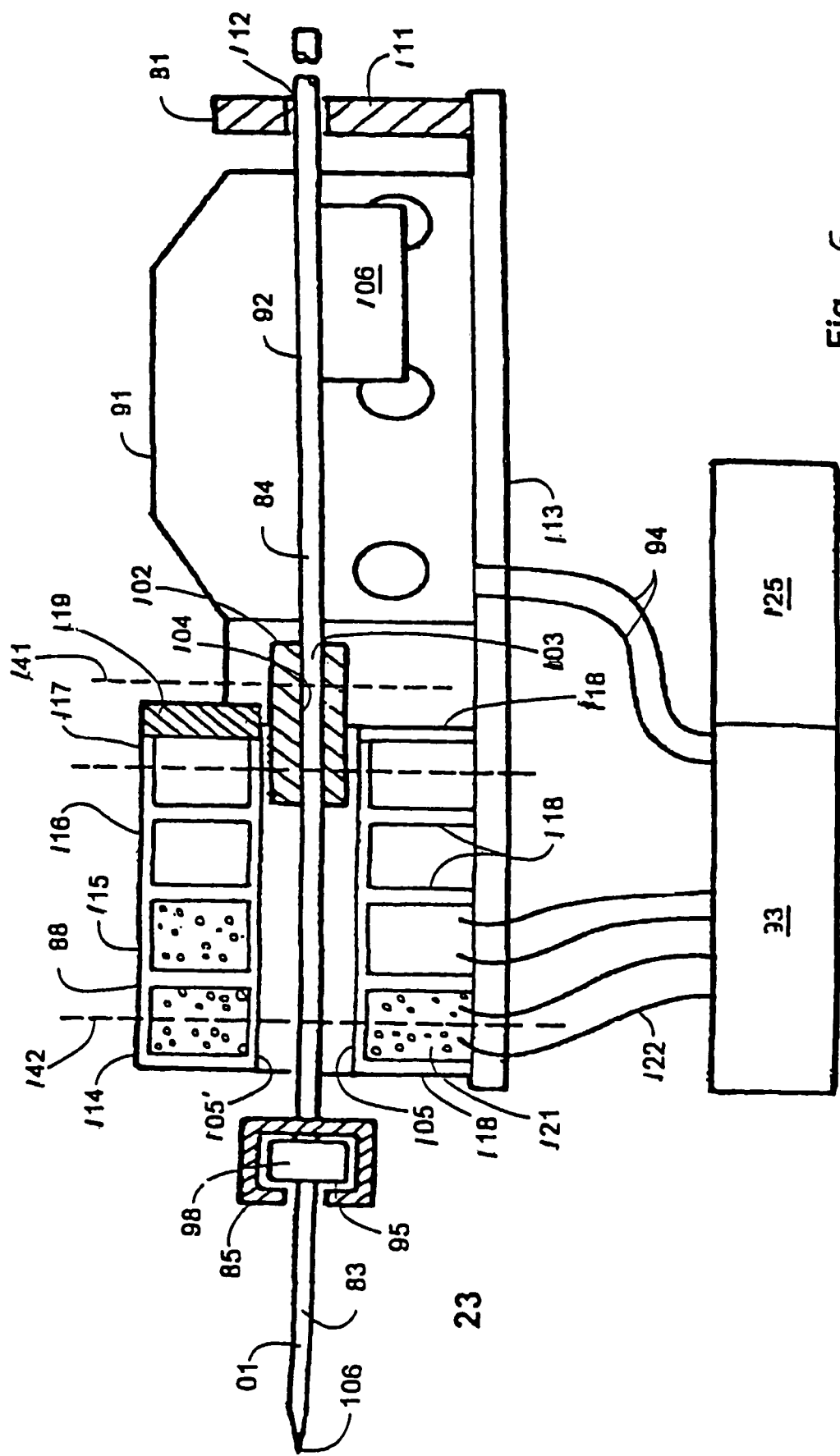
FIG. 5 is an elevation view in partial longitudinal section of the tissue penetration device of FIG. 4.

Referring to FIG. 5, the lancing device 80 can be seen in more detail, in partial longitudinal section. The penetrating member 83 has a proximal end 95 and a distal end 96 with a sharpened point at the distal end 96 of the penetrating member 83 and a drive head 98 disposed at the proximal end 95 of the penetrating member 83. A penetrating member shaft 201 is disposed between the drive head 98 and the sharpened point 97. The penetrating member shaft 201 may be comprised of stainless steel, or any other suitable material or alloy and have a transverse dimension of about 0.1 to about 0.4 mm. The penetrating member shaft may have a length of about 3 mm to about 50 mm, specifically, about 15 mm to about 20 mm. The drive head 98 of the penetrating member 83 is an enlarged portion having a transverse dimension greater than a transverse dimension of the penetrating member shaft 201 distal of the drive head 98. This configuration allows the drive head 98 to be mechanically captured by the drive coupler 85. The drive head 98 may have a transverse dimension of about 0.5 to about 2 mm.

A magnetic member 102 is secured to the elongate coupler shaft 84 proximal of the drive coupler 85 on a distal portion 203 of the elongate coupler shaft 84. The magnetic member 102 is a substantially cylindrical piece of magnetic material having an axial lumen 204 extending the length of the magnetic member 102. The magnetic member 102 has an outer transverse dimension that allows the magnetic member 102 to slide easily within an axial lumen 105 of a low friction, possibly lubricious, polymer guide tube 105' disposed within the driver coil pack 88. The magnetic member 102 may have an outer transverse dimension of about 1.0 to about 5.0 mm, specifically, about 2.3 to about 2.5 mm. The magnetic member 102 may have a length of about 3.0 to about 5.0 mm, specifically, about 4.7 to about 4.9 mm. The magnetic member 102 can be made from a variety of magnetic materials including ferrous metals such as ferrous steel, iron, ferrite, or the like. The magnetic member 102 may be secured to the distal portion 203 of the elongate coupler shaft 84 by a variety of methods including adhesive or epoxy bonding, welding, crimping or any other suitable method.

Proximal of the magnetic member 102, an optical encoder flag 206 is secured to the elongate coupler shaft 84. The optical encoder flag 206 is configured to move within a slot 107 in the position sensor 91. The slot 107 of the position sensor 91 is formed between a first body portion 108 and a second body portion 109 of the position sensor 91. The slot 107 may have separation width of about 1.5 to about 2.0 mm. The optical encoder flag 206 can have a length of about 14 to about 18 mm, a width of about 3 to about 5 mm and a thickness of about 0.04 to about 0.06 mm.

The optical encoder flag 206 interacts with various optical beams generated by LEDs disposed on or in the position sensor body portions 108 and 109 in a predetermined manner. The interaction of the optical beams generated by the LEDs of the position sensor 91 generates a signal that indicates the longitudinal position of the optical flag 206 relative to the position sensor 91 with a substantially high degree of resolution. The resolution of the position sensor 91 may be about 200 to about 400 cycles per inch, specifically, about 350 to about 370 cycles per inch. The position sensor 91 may have a speed response time (position/time resolution) of 0 to about 120,000 Hz, where one dark and light stripe of the flag constitutes one Hertz, or cycle per second. The position of the optical encoder flag 206 relative to the magnetic member 102, driver coil pack 88 and position sensor 91 is such that the optical encoder 91 can provide precise positional information about the penetrating member 83 over the entire length of the penetrating member's power stroke.

An optical encoder that is suitable for the position sensor 91 is a linear optical incremental encoder, model HEDS 9200, manufactured by Agilent Technologies. The model HEDS 9200 may have a length of about 20 to about 30 mm, a width of about 8 to about 12 mm, and a height of about 9 to about 11 mm. Although the position sensor 91 illustrated is a linear optical incremental encoder, other suitable position sensor embodiments could be used, provided they posses the requisite positional resolution and time response. The HEDS 9200 is a two channel device where the channels are 90 degrees out of phase with each other. This results in a resolution of four times the basic cycle of the flag. These quadrature outputs make it possible for the processor to determine the direction of penetrating member travel. Other suitable position sensors include capacitive encoders, analog reflective sensors, such as the reflective position sensor discussed above, and the like.

A coupler shaft guide 111 is disposed towards the proximal end 81 of the lancing device 80. The guide 111 has a guide lumen 112 disposed in the guide 111 to slidingly accept the proximal portion 92 of the elongate coupler shaft 84. The guide 111 keeps the elongate coupler shaft 84 centered horizontally and vertically in the slot 102 of the optical encoder 91.

Figure 6:
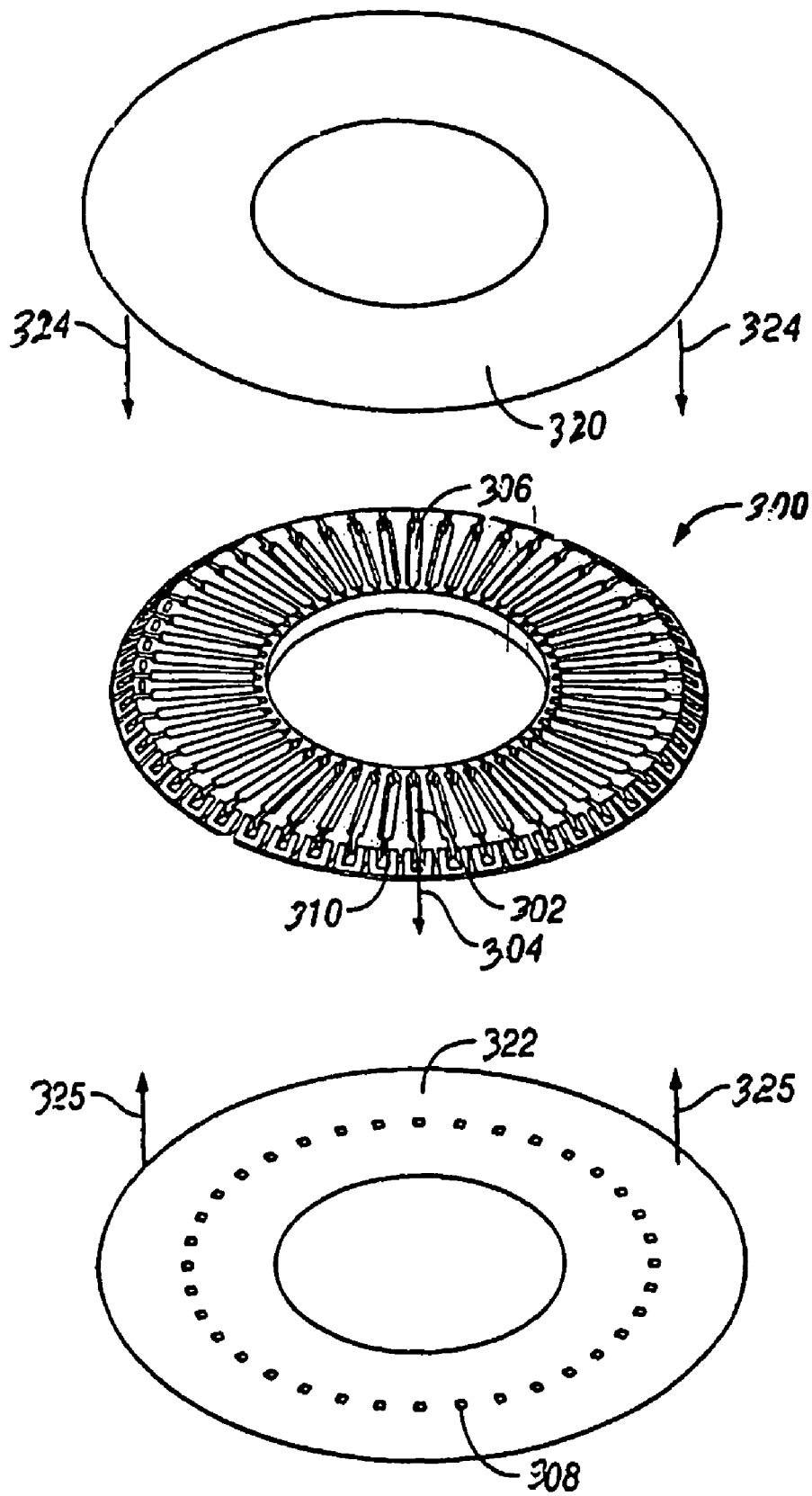
FIG. 6 shows one embodiment of a radial disc for use with the present invention.

Referring now to FIG. 6, a still further embodiment of a cartridge according to the present invention will be described. FIG. 6 shows one embodiment of a cartridge 300 which may be removably inserted into an apparatus for driving penetrating members to pierce skin or tissue. The cartridge 300 has a plurality of penetrating members 302 that may be individually or otherwise selectively actuated so that the penetrating members 302 may extend outward from the cartridge, as indicated by arrow 304, to penetrate tissue. In the present embodiment, the cartridge 300 may be based on a flat disc with a number of penetrating members such as, but in no way limited to, (25, 50, 75, 100, ...) arranged radially on the disc or cartridge 300. It should be understood that although the cartridge 300 is shown as a disc or a disc-shaped housing, other shapes or configurations of the cartridge may also work without departing from the spirit of the present invention of placing a plurality of penetrating members to be engaged, singly or in some combination, by a penetrating member driver.

Each penetrating member 302 may be contained in a cavity 306 in the cartridge 300 with the penetrating member's sharpened end facing radially outward and may be in the same plane as that of the cartridge. The cavity 306 may be molded, pressed, forged, or otherwise formed in the cartridge. Although not limited in this manner, the ends of the cavities 306 may be divided into individual fingers (such as one for each cavity) on the outer periphery of the disc. The particular shape of each cavity 306 may be designed to suit the size or shape of the penetrating member therein or the amount of space desired for placement of the analyte detecting members 308. For example and not limitation, the cavity 306 may have a V-shaped cross-section, a U-shaped cross-section, C-shaped cross-section, a multi-level cross section or the other cross-sections. The opening 310 through which a penetrating member 302 may exit to penetrate tissue may also have a variety of shapes, such as but not limited to, a circular opening, a square or rectangular opening, a U-shaped opening, a narrow opening that only allows the penetrating member to pass, an opening with more clearance on the sides, a slit, a configuration as shown in FIG. 75, or the other shapes.

In this embodiment, after actuation, the penetrating member 302 is returned into the cartridge and may be held within the cartridge 300 in a manner so that it is not able to be used again. By way of example and not limitation, a used penetrating member may be returned into the cartridge and held by the launcher in position until the next lancing event. At the time of the next lancing, the launcher may disengage the used penetrating member with the cartridge 300 turned or indexed to the next clean penetrating member such that the cavity holding the used penetrating member is position so that it is not accessible to the user (i.e. turn away from a penetrating member exit opening). In some embodiments, the tip of a used penetrating member may be driven into a protective stop that hold the penetrating member in place after use. The cartridge 300 is replaceable with a new cartridge 300 once all the penetrating members have been used or at such other time or condition as deemed desirable by the user.

Referring still to the embodiment in FIG. 6, the cartridge 300 may provide sterile environments for penetrating members via seals, foils, covers, polymeric, or similar materials used to seal the cavities and provide enclosed areas for the penetrating members to rest in. In the present embodiment, a foil or seal layer 320 is applied to one surface of the cartridge 300. The seal layer 320 may be made of a variety of materials such as a metallic foil or other seal materials and may be of a tensile strength and other quality that may provide a sealed, sterile environment until the seal layer 320 is penetrate by a suitable or penetrating device providing a preselected or selected amount of force to open the sealed, sterile environment. Each cavity 306 may be individually sealed with a layer 320 in a manner such that the opening of one cavity does not interfere with the sterility in an adjacent or other cavity in the cartridge 800. As seen in the embodiment of FIG. 6, the seal layer 320 may be a planar material that is adhered to a top surface of the cartridge 800.

Depending on the orientation of the cartridge 300 in the penetrating member driver apparatus, the seal layer 320 may be on the top surface, side surface, bottom surface, or other positioned surface. For ease of illustration and discussion of the embodiment of FIG. 6, the layer 320 is placed on a top surface of the cartridge 800. The cavities 306 holding the penetrating members 302 are sealed on by the foil layer 320 and thus create the sterile environments for the penetrating members. The foil layer 320 may seal a plurality of cavities 306 or only a select number of cavities as desired.

In a still further feature of FIG. 6, the cartridge 300 may optionally include a plurality of analyte detecting members 308 on a substrate 322 which may be attached to a bottom surface of the cartridge 300. The substrate may be made of a material such as, but not limited to, a polymer, a foil, or other material suitable for attaching to a cartridge and holding the analyte detecting members 308. As seen in FIG. 6, the substrate 322 may hold a plurality of analyte detecting members, such as but not limited to, about 10-50, 50-100, or other combinations of analyte detecting members. This facilitates the assembly and integration of analyte detecting members 308 with cartridge 300. These analyte detecting members 308 may enable an integrated body fluid sampling system where the penetrating members 302 create a wound tract in a target tissue, which expresses body fluid that flows into the cartridge for analyte detection by at least one of the analyte detecting members 308. The substrate 322 may contain any number of analyte detecting members 308 suitable for detecting analytes in cartridge having a plurality of cavities 306. In one embodiment, many analyte detecting members 308 may be printed onto a single substrate 322 which is then adhered to the cartridge to facilitate manufacturing and simplify assembly. The analyte detecting members 308 may be electrochemical in nature. The analyte detecting members 308 may further contain enzymes, dyes, or other detectors which react when exposed to the desired analyte. Additionally, the analyte detecting members 308 may comprise of clear optical windows that allow light to pass into the body fluid for analyte analysis. The number, location, and type of analyte detecting member 308 may be varied as desired, based in part on the design of the cartridge, number of analytes to be measured, the need for analyte detecting member calibration, and the sensitivity of the analyte detecting members. If the cartridge 300 uses an analyte detecting member arrangement where the analyte detecting members are on a substrate attached to the bottom of the cartridge, there may be through holes (as shown in FIG. 76), wicking elements, capillary tube or other devices on the cartridge 300 to allow body fluid to flow from the cartridge to the analyte detecting members 308 for analysis. In other configurations, the analyte detecting members 308 may be printed, formed, or otherwise located directly in the cavities housing the penetrating members 302 or areas on the cartridge surface that receive blood after lancing.

The use of the seal layer 320 and substrate or analyte detecting member layer 322 may facilitate the manufacture of these cartridges 10. For example, a single seal layer 320 may be adhered, attached, or otherwise coupled to the cartridge 300 as indicated by arrows 324 to seal many of the cavities 306 at one time. A sheet 322 of analyte detecting members may also be adhered, attached, or otherwise coupled to the cartridge 300 as indicated by arrows 325 to provide many analyte detecting members on the cartridge at one time. During manufacturing of one embodiment of the present invention, the cartridge 300 may be loaded with penetrating members 302, sealed with layer 320 and a temporary layer (not shown) on the bottom where substrate 322 would later go, to provide a sealed environment for the penetrating members. This assembly with the temporary bottom layer is then taken to be sterilized. After sterilization, the assembly is taken to a clean room (or it may already be in a clean room or equivalent environment) where the temporary bottom layer is removed and the substrate 322 with analyte detecting members is coupled to the cartridge as shown in FIG. 6. This process allows for the sterile assembly of the cartridge with the penetrating members 302 using processes and/or temperatures that may degrade the accuracy or functionality of the analyte detecting members on substrate 322. As a nonlimiting example, the entire cartridge 300 may then be placed in a further sealed container such as a pouch, bag, plastic molded container, etc . . . to facilitate contact, improve ruggedness, and/or allow for easier handling.

In some embodiments, more than one seal layer 320 may be used to seal the cavities 306. As examples of some embodiments, multiple layers may be placed over each cavity 306, half or some selected portion of the cavities may be sealed with one layer with the other half or selected portion of the cavities sealed with another sheet or layer, different shaped cavities may use different seal layer, or the like. The seal layer 320 may have different physical properties, such as those covering the penetrating members 302 near the end of the cartridge may have a different color such as red to indicate to the user (if visually inspectable) that the user is down to say 10, 5, or other number of penetrating members before the cartridge should be changed out.

Chemical sensor formulations have been developed that are capable of conducting numerous different chemical analyses on small samples, so that the, maximum number of medical tests can be made using the minimum amount of sample. Volume of less than 100 nL are possible. These blood chemistry tests include small molecules such as glucose and lactate, blood gasses (including $pO_2$, $pCO_2$), blood pH, ions ($Na^+$, $Ca^{++}$, $K^+$), and hematology, hematocrit and coagulation and hemoglobin factors, as well as immuno-diagnostics, and DNA testing. Parallel testing can be performed on the sensing cartridge using fluorescence-based detection using oxygen sensors so that a wide variety of tests can be performed using optical sensors for several species that can be interrogated with one illumination source and read with one detector (Wolfbeis O. Sensors and Actuators B 51 (1998) 17-24). Analysis of multiple analytes from a fluid of unknown composition has been described (U.S. Pat. No. 6,379,969 Mauze et al). Analysis of a plurality of metabolites in a hand held diagnostic device using a single cartridge using about 1-3 µL of blood has also been described (US2003/0073931 Universal Diagnostic platform, US2003/0073089 Companion cartridge for disposable diagnostic testing). There is a need for a plurality of POC tests on a single cartridge such that sequential tests may be performed in an integrated fashion without changing the test cartridge.

Figure 10:
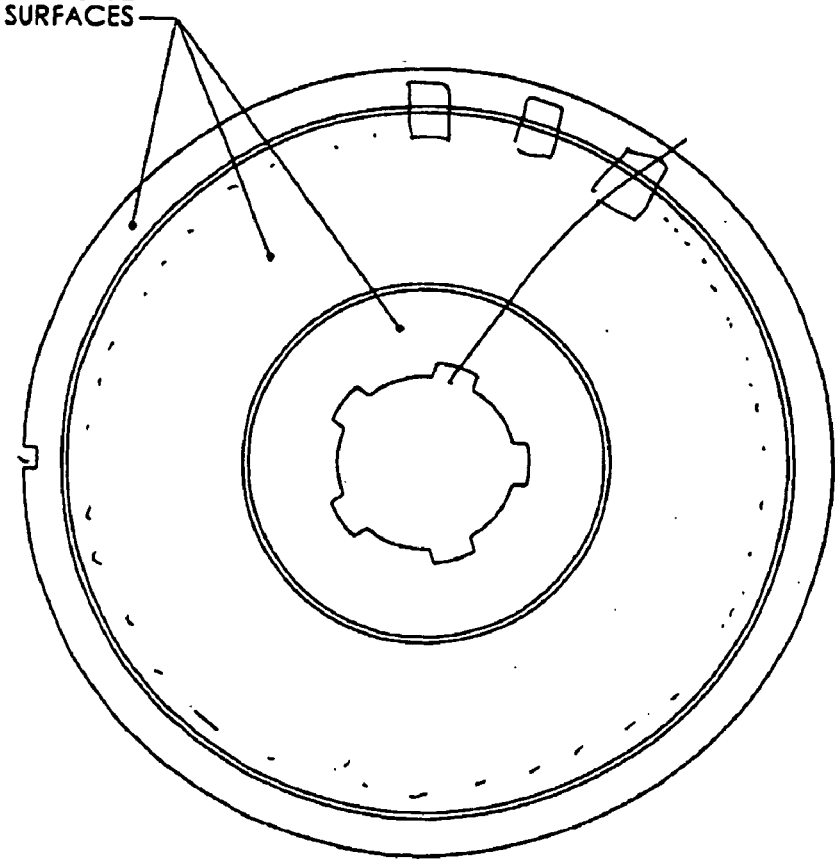
FIG. 10 shows one embodiment of a cartridge having analyte detecting members on the underside.

In one embodiment of the present invention, each cartridge may contain a penetrating member/analyte detecting member combination on a radial disc format, interrogated and read by a single illumination/detection device. Alternatively a series of tests can be measured electrochemically and reported. In one embodiment, only those tests, which are desired at the time the sample is taken need to be reported, though all tests are carried out. This avoids having to change cartridges for a specific combination or panel since bundled tests with menu option. Of course, in some alternative embodiments, several cartridges, each with specific analyte testing capabilities, may be used for given disease state as desired. Test combinations may include a plurality of tests for a single penetrating member/analyte detecting member combination repeated up to 100 times. In one embodiment, the nominal test panel would include blood gasses, electrolytes, metabolites, immunoassay and coagulation as a first choice. Cell counting and hematology are complex and may require almost 75% more space in the analyte detecting member area to complete. This may be accomplished by using the underside of the disk and a second layer if more surface area is required, as seen in FIG. 10. In one embodiment, the cartridge may contain microfluidic channels to fluidly connect fluid receiving sites on the top of the cartridge to those on the bottom.

Figure 7A:
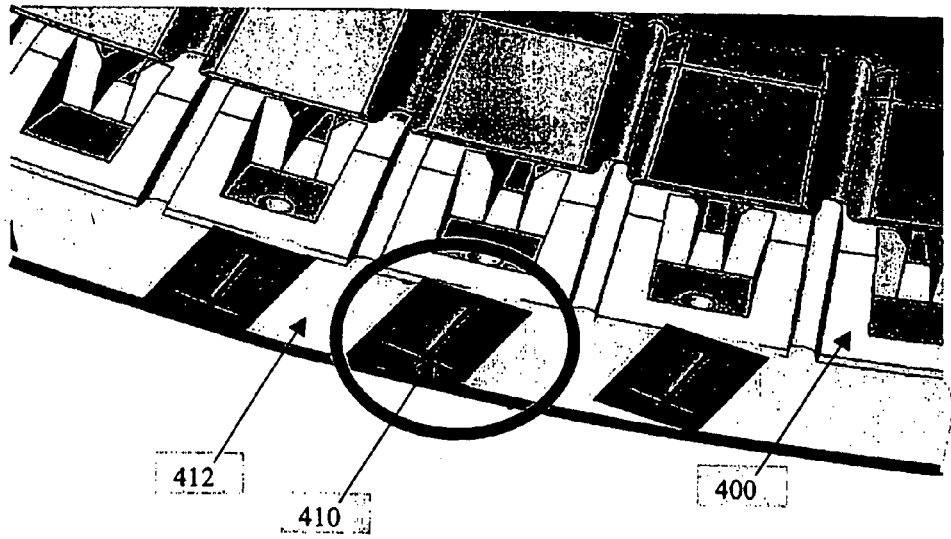
FIGS. 7A and 7B show embodiments of the present invention.
Figure 7B:
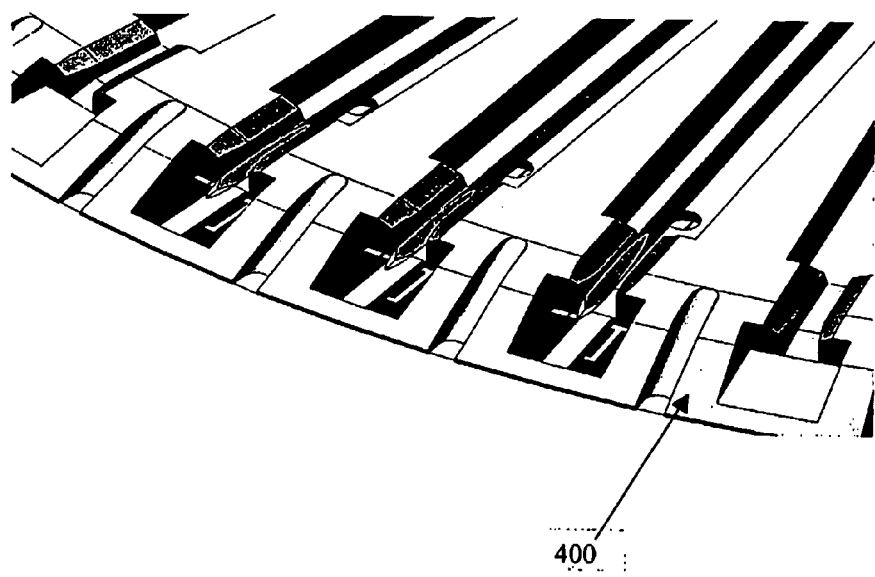
Figure 8:
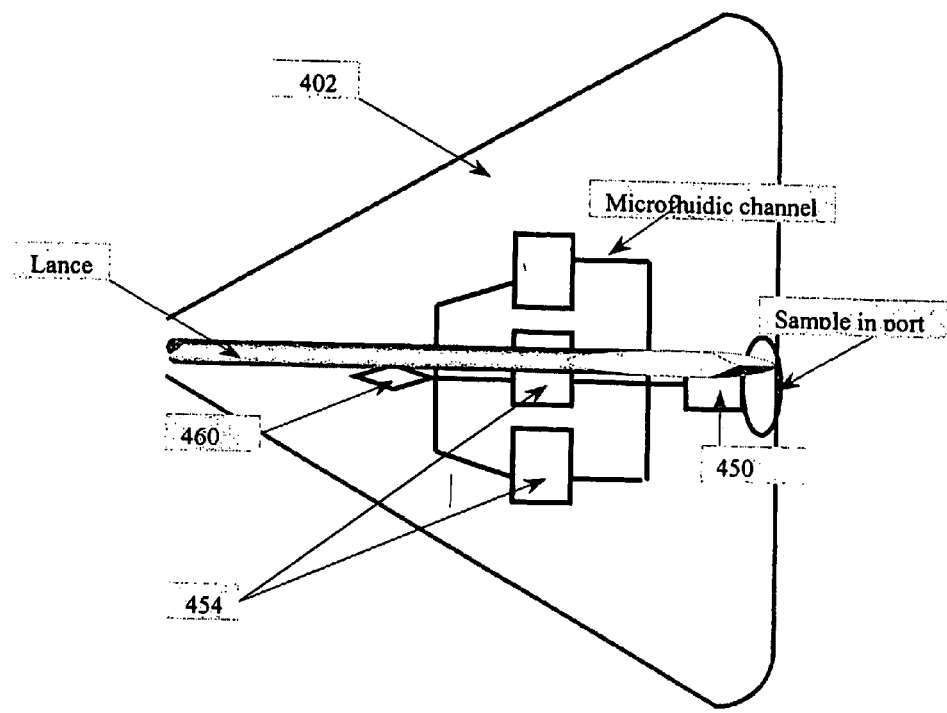
FIG. 8 shows one embodiment of the present invention for performing multiple measurements.
Figure 9:
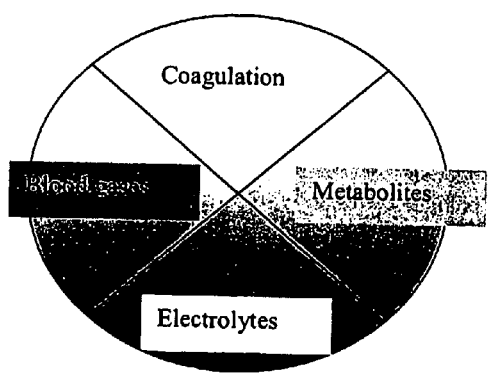
FIG. 9 shows one embodiment of a cartridge configured to measure different analytes.

In one embodiment, the invention is comprised of an electronic lancet driver to penetrate tissue, a single disposable cartridge 400 containing penetrating member/analyte detecting member pairs 402 arranged on a radial disk of about 6 cm in diameter. Penetrating members are coupled to the electronic actuator, which can actuate the penetrating members radially outward from the cartridge to penetrate tissue. As seen in FIG. 7, optical or electrochemical analyte detecting members 410 may be coupled to the cartridge, and positioned on the cartridge to receive blood from the wound created by the penetrating member. In some embodiments, the portion 412 may be an annular ring attached to the cartridge 410, instead of being integrally formed. In one embodiment, capillary forces draw the blood or other fluid sample, which flows from the wound to the surface of the skin, through an opening and then to the analyte detecting member chamber situated, on the support disc (FIGS. 8 and 9). In this embodiment, once blood fills the analyte detecting member, analytical testing can be performed on the sample. Results may be read optically via transparent windows aligned with optical analyte detecting members, or electrochemically from electrodes in contact with the biosensor chemistry.

In one embodiment as seen in FIG. 8, chemical tests are started simultaneously by having the blood fill a prefill chamber 450. It is microfluidically designed so that when enough sample has arrived to fill all the analyte detecting members, the chamber 450 is primed to empty and fill the analyte detecting member chemistry zones 454 instantaneously. It should be understood that the zone 454 associated with each penetrating member may vary. Some embodiments may have 2, 3, 4, 5, 6, 7, 8, 9, 10, or more zones, depending on the types of tests being run and the fluid requirements for each zone. In some embodiments, more than one zone may be measuring the same analyte or they may all be measuring for the same analyte. Some of the zones may be on the top of the cartridge while the remaining are on the underside of the cartridge.

In some embodiments, a blister 460 may be included. The blister 460 may be manufactured under pressure. When the blister 460 is broken (either by the indexing mechanism or another method) the pressure is released and calibration and or washing fluid can be released throughout the test area or zones 454 prior to the arrival of blood or other fluid sample to the test region 454 so that equilibration can take place if required. A vent may also be included to prevent overfill of the cartridge if too much sample is delivered. Additionally and fill indicator may be present to indicate adequate sample fill of the sample chamber. In some embodiments; the vent and/or fill indicator may be coupled to the sample chamber or to the chemistry zones.

FIG. 9 shows a still further embodiment of the present invention where different zones are on each cartridge 400. The cartridge may be divided by different test chemistry regions. In some embodiments, the cartridge 400 may have the same tests associated with each penetrating member. In other embodiments, the cartridge 400 may be divided into 2, 3, 4, 5, 6, 7, 8, 9, 10, or more zones, depending on which tests should be run. Some tests may vary based on the time of day that the testing occurs. The cartridge may be rotated as desired to bring the desired test into position for use with fluid sampling.

It should be understood that embodiments of the present invention may provide at least some of the following advantages. All of the advantages miniaturized, disposable, biohazard etc, as described in commonly assigned copending U.S. patent application Ser. Nos. 10/127,395, 10/324,053, and 10/429,196. The device may have handheld, two way communication, data management (as per US 2003/0073931 A1 Universal diagnostic platform). The device may have integrated sampling/POC testing device for one step sample to read. The device may have blood volume requirement less than 1 microL. The device may have many tests on single analyte detecting member/penetrating member combination. Each segment may have the same test or the cartridge can be divided into regions with a plurality of specific tests. All tests run, subset reported, cost of test only for tests required. Analyte detecting members may be electrochemical or optical (or any combination of both or other analyte detecting member types). The device may include companion cartridge for more complex less common tests, only used if required. In some embodiments as shown in FIG. 10, the underside of a cartridge as described in Ser. No. 10/429,196 may be used for tests requiring larger surface area e.g. washing steps in hematology or cell counting. All tests may start simultaneously by means of an upstream fixed volume chamber which empties instantaneously when full. The device may have vents, seals, fill detectors as described in 10/324,053. Cartridge vent system opens by piercing mechanism to allow on board calibration fluids to start flowing into relevant fluidic structures. The device may optically interrogate from bottom as in F1 optical disclosure. Array detection may be used as in Ser. No. 10/324,053.

In another aspect of the present invention, an improved analyte measurement storage device will be described. The current invention teaches devices and methods for isolating the enzymatic region from the sensing region in such a way that they can be fabricated and stored without interacting with each other during their pre-use phase. However the regions can be properly coupled during their use for proper functioning.

Referring now to FIG. 11, a penetrating member 500 such as one driven by device as taught herein (though not limited in that manner) may be used to puncture a structure 502 containing an enzyme area 504 and a sensing area 506. Septums or seals 508, 510, 512 and may be used to keep these two areas separated prior to use. As a nonlimiting example, the area 504 may be stored in an inert gas (non oxygen) environment, while the area 506 is stored in a different environment. The flow of fluid 520 into the region may be due to gravity, capillary force, vacuum, or other technique. The flow allows the fluid to first gather material from the enzyme area 504 which may prepare the fluid for sensing the area 506. These sensing techniques may be used with optical analyte detecting member as known to those skilled in the art.

In one embodiment of this invention, the enzyme layer is deposited on the surface of a capillary region through which the sample to be analyzed flows to the sensing region where the transduction takes place. The coating can be placed on the wall of the capillary itself, or on the surface of any component of the device such as a penetrating member that comes in contact with the sample as it flows toward the sensing region. As the sample moves through this region it either dissolves the enzyme layer or extracts the enzyme into the sample. The rate of this enzyme uptake by the sample can be adjusted such that by the time sample reaches the sensing region the enzyme has adequately interacted with the analyte to present appropriate sample for detection by the analyte detecting member. This can be achieved by adjusting one or more of the following factors: 1) the length of the coated region along the sample flow path, 2) thickness of the coating, 3) chemical composition of the coating, 4) porosity of the coating, 5) speed of the flow of the sample. These methods and means of achieving the appropriate enzyme uptake may be dependent upon the particular chemistry of enzyme and other reagents and would be readily determined by those familiar with the art of enzyme chemistry. These alternatives are included in this invention by reference.

In another embodiment of this invention, the sensing regions can be located along the flow path of the sample. In such a configuration, the enzyme layer is still coated on the walls along the flow path; the sample picks up different amount of the enzyme as it passes over each of the sensing regions. Thus the sensing region closest to the sample entry port has the least amount of enzyme and the one furthest along the flow path has the most amount of the enzyme. Such as scheme can be advantageously used where the amount of enzyme required for getting optimal analyte detecting member signal depends upon the (unknown) amount of the analyte in the sample. Since the analyte content is not known a priori, series of signals obtained from the sensing regions as a function of the amount of enzyme taken up by the sample can be evaluated and the optimal signal can be used for determining the analyte concentration.

Although these embodiments refer to the enzyme as an example of the chemical that is taken up by the sample for analysis, any other chemical species that is required to be dissolved in on contacted with the sample before analysis could be thus disposed using the teachings of this invention.

The current invention results in several advantages in the devices for analyte sensing and methods of manufacturing the same. Isolation of the enzyme from the sensing regions allows one to use different or incompatibles chemistries such as solvents for manufacturing and depositing the sensing layer and the enzyme layer.

An example is a glucose analyte detecting member based on sensing of oxygen depletion by the reaction of glucose with glucose oxidase. In this type of analyte detecting members, the oxygen analyte detecting member could be made of a silicone rubber layer containing an oxygen sensing fluorophore. The solvents required for depositing this layer are usually lipophilic and will readily reduce the activity of glucose oxidase. These solvents, even in minute quantities, can outgas from the layer and over time gradually deactivate the enzyme. Based on the teachings of this invention, the oxygen-sensing layer and the enzyme layer can be physically isolated from each other. Or, they can be fabricated separately and then assembled together after adequate out gassing of the harmful solvents etc. Alternatively, the two layers can be separated by a physical barrier such as septum during the pre-use storage of the device. At the time of analysis, the barrier can be broken by application of energy (thermal or electrical) or by impact of an object such as a penetrating member. Using such a barrier would enable one to store the layers in different atmospheres. For example, the enzyme could be stored in nitrogen atmosphere while the oxygen sensing layer could be stored in oxygen or another gas composition adequate for calibration at the time of use or stability during storage. If the oxygen analyte detecting member is stored in an oxygen rich atmosphere, the dissolved oxygen could act as a reagent for the glucose-GOD reaction. Such a scheme will provide a baseline for the oxygen consumed by the reaction of glucose that is not limited by the dissolved oxygen content of the sample.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, the location of the penetrating member drive device may be varied, relative to the penetrating members or the cartridge. With any of the above embodiments, the penetrating member tips may be uncovered during actuation (i.e. penetrating members do not pierce the penetrating member enclosure or protective foil during launch). With any of the above embodiments, the penetrating members may be a bare penetrating member during launch. With any of the above embodiments, the penetrating members may be bare penetrating members prior to launch as this may allow for significantly tighter densities of penetrating members. In some embodiments, the penetrating members may be bent, curved, textured, shaped, or otherwise treated at a proximal end or area to facilitate handling by an actuator. The penetrating member may be configured to have a notch or groove to facilitate coupling to a gripper. The notch or groove may be formed along an elongate portion of the penetrating member. With any of the above embodiments, the cavity may be on the bottom or the top of the cartridge, with the gripper on the other side. In some embodiments, analyte detecting members may be printed on the top, bottom, or side of the cavities. The front end of the cartridge maybe in contact with a user during lancing. The same driver may be used for advancing and retraction of the penetrating member. The penetrating member may have a diameters and length suitable for obtaining the blood volumes described herein. The penetrating member driver may also be in substantially the same plane as the cartridge. The driver may use a through hole or other opening to engage a proximal end of a penetrating member to actuate the penetrating member along a path into and out of the tissue. The embodiments herein are adapted for use with lancing devices described in U.S. patent applications Ser. No. 10/127, 395 and U.S. Ser. No. 10/323,624. It should also be understood that the multiple measurement zone configuration is not limited to a radial disc and may be adapted for use with cartridges that are rectangular, square, oval, polygonal, hexagonal, or other shaped in outline. They may be associated with single penetrating member cartridges or multiple penetrating member cartridges.

Any of the features described in this application or any reference disclosed herein may be adapted for use with any embodiment of the present invention. For example, the devices of the present invention may also be combined for use with injection penetrating members or needles as described in commonly assigned, copending U.S. patent application Ser. No. 10/127,395 filed Apr. 19, 2002. An analyte detecting member to detect the presence of foil may also be included in the lancing apparatus. For example, if a cavity has been used before, the foil or sterility barrier will be punched. The analyte detecting member can detect if the cavity is fresh or not based on the status of the barrier. It should be understood that in optional embodiments, the sterility barrier may be designed to pierce a sterility barrier of thickness that does not dull a tip of the penetrating member. The lancing apparatus may also use improved drive mechanisms. For example, a solenoid force generator may be improved to try to increase the amount of force the solenoid can generate for a given current. A solenoid for use with the present invention may have five coils and in the present embodiment the slug is roughly the size of two coils. One change is to increase the thickness of the outer metal shell or windings surround the coils. By increasing the thickness, the flux will also be increased. The slug may be split; two smaller slugs may also be used and offset by ½ of a coil pitch. This allows more slugs to be approaching a coil where it could be accelerated. This creates more events where a slug is approaching a coil, creating a more efficient system.

In another optional alternative embodiment, a gripper in the inner end of the protective cavity may hold the penetrating member during shipment and after use, eliminating the feature of using the foil, protective end, or other part to retain the used penetrating member. Some other advantages of the disclosed embodiments and features of additional embodiments include: same mechanism for transferring the used penetrating members to a storage area; a high number of penetrating members such as 25, 50, 75, 100, 500, or more penetrating members may be put on a disk or cartridge; molded body about a penetrating member becomes unnecessary; manufacturing of multiple penetrating member devices is simplified through the use of cartridges; handling is possible of bare rods metal wires, without any additional structural features, to actuate them into tissue; maintaining extreme (better than 50 micron -lateral- and better than 20 micron vertical) precision in guiding; and storage system for new and used penetrating members, with individual cavities/slots is provided. The housing of the lancing device may also be sized to be ergonomically pleasing. In one embodiment, the device has a width of about 56 mm, a length of about 105 mm and a thickness of about 15 mm. Additionally, some embodiments of the present invention may be used with non-electrical force generators or drive mechanism. For example, the punch device and methods for releasing the penetrating members from sterile enclosures could be adapted for use with spring based launchers. The gripper using a frictional coupling may also be adapted for use with other drive technologies.

Still further optional features may be included with the present invention. For example, with any of the above embodiments, the location of the penetrating member drive device may be varied, relative to the penetrating members or the cartridge. With any of the above embodiments, the penetrating member tips may be uncovered during actuation (i.e. penetrating members do not pierce the penetrating member enclosure or protective foil during launch). The penetrating members may be a bare penetrating member during launch. In some embodiments, the penetrating member may be a patent needle. The same driver may be used for advancing and retraction of the penetrating member. Different analyte detecting members detecting different ranges of glucose concentration, different analytes, or the like may be combined for use with each penetrating member. Non-potentiometric measurement techniques may also be used for analyte detection. For example, direct electron transfer of glucose oxidase molecules adsorbed onto carbon nanotube powder microelectrode may be used to measure glucose levels. In some embodiments, the analyte detecting members may formed to flush with the cartridge so that a "well" is not formed. In some other embodiments, the analyte detecting members may formed to be substantially flush (within 200 microns or 100 microns) with the cartridge surfaces. In all methods, nanoscopic wire growth can be carried out via chemical vapor deposition (CVD). In all of the embodiments of the invention, preferred nanoscopic wires may be nanotubes. Any method useful for depositing a glucose oxidase or other analyte detection material on a nanowire or nanotube may be used with the present invention. Additionally, for some embodiments, any of the cartridge shown above may be configured without any of the penetrating members, so that the cartridge is simply an analyte detecting device. Still further, the indexing of the cartridge may be such that adjacent cavities may not necessarily be used serially or sequentially. As a nonlimiting example, every second cavity may be used sequentially, which means that the cartridge will go through two rotations before every or substantially all of the cavities are used. As another nonlimiting example, a cavity that is 3 cavities away, 4 cavities away, or N cavities away may be the next one used. This may allow for greater separation between cavities containing penetrating members that were just used and a fresh penetrating member to be used next. For any of the embodiments herein, they may be configured to provide the various velocity profiles described.

Application Ser. No. 10/127,395 filed Apr. 19, 2002. This application is also a continuation-in-part of commonly assigned, copending U.S. patent application Ser. No. 10/237,261 filed Sep. 5, 2002. This application is further a continuation-in-part of commonly assigned, copending U.S. patent application Ser. No. 10/420,535 filed Apr. 21, 2003. This application is further a continuation-in-part of commonly assigned, copending U.S. patent application Ser. No. 10/335,142 filed Dec. 31, 2002. All applications listed above are incorporated herein by reference for all purposes. The U.S. provisional applications Ser. Nos. 60/478,693 and 60/478,681 are fully incorporated herein by reference.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited.

Expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A body fluid sampling device comprising:
a cartridge containing a plurality of penetrating members;
a drive force generator coupled to a processor and configured to be coupled to an active one of said penetrating members and to move said active one of said penetrating members;
the processor configured to provide information relative to a depth of penetration of said active one of said penetrating members through a skin surface when said active one of said penetrating members is moved; and
a plurality of analyte detecting members each associated with one of said penetrating members, the plurality of analyte detecting members being attached to a bottom surface of said cartridge, wherein a first portion of the analyte detecting members measure a first analyte and a second portion of the analyte detecting members measure a second analyte.

2. The device of claim 1 wherein the penetrating member driver is coupled to a position sensor in communication with the processor, said position sensor used to detect a position of the active one of said penetrating members while penetrating tissue.

3. The device of claim 1 wherein said first portion of analyte detecting members are all located on one area of the cartridge while said second portion of analyte detecting members are all located on a second area of the cartridge.

4. The device of claim 1 wherein said first portion of analyte detecting members measure analytes related to blood gases.

5. The device of claim 1 wherein said second portion of analyte detecting members measure analytes related to electrolytes.

6. The device of claim 1 wherein said second portion of analyte detecting members measure analytes related to at least one of the following: blood gases, electrolytes, coagulation, or metabolites.

7. The device of claim 1 further comprising a handheld, two way communication, data management system.

8. The device of claim 1 further comprising an integrated sampling/POC testing device for one step sample to read.

9. The device of claim 1 wherein body fluid requirement for each analyte detecting member is less than 1 microliter.

10. The device of claim 1 wherein the processor is configured to measure the first and the second analyte while reporting only those results which are desired at the time the sample is taken.

11. The device of claim 1 wherein said analyte detecting members use either electrochemical, optical, or combinations of the measurement techniques.

12. The device of claim 1 further comprising a companion cartridge wherein additional analyte detecting members are coupled for more complex less common tests if required.

13. The device of claim 1 further comprising vents, seals, and/or fill detectors.

14. The device of claim 1 further comprising a cartridge vent system that opens by piercing mechanism to allow on board calibration fluids to start flowing into relevant fluidic structures.

15. A body fluid sampling device comprising:
a cartridge containing a plurality of penetrating members;
a plurality of analyte detecting members each associated with one of the plurality of penetrating members on said cartridge, wherein a first portion of the analyte detecting members measure a first analyte and a second portion of the analyte detecting members measure a second analyte;
a penetrating member driver for moving an active one of said penetrating members from a first position outward to penetrate tissue; and
many tests on a single penetrating member/analyte detecting member combination.

16. A body fluid sampling device comprising:
a cartridge containing a plurality of penetrating members;
a plurality of analyte detecting members each associated with one of the plurality of penetrating members on said cartridge, wherein a first portion of the analyte detecting members measure a first analyte and a second portion of the analyte detecting members measure a second analyte;
a penetrating member driver for moving an active one of said penetrating members from a first position outward to penetrate tissue;
an upstream fixed volume chamber which empties instantaneously when full so that all tests start simultaneously.

17. A body fluid sampling device comprising:
a cartridge containing a plurality of penetrating members;
a plurality of analyte detecting members each associated with one of the plurality of penetrating members on said cartridge, wherein a first portion of the analyte detecting members measure a first analyte and a second portion of the analyte detecting members measure a second analyte;
a penetrating member driver for moving an active one of said penetrating members from a first position outward to penetrate tissue;
an array detection having a storage area having a sensing area;
another storage area having an enzyme area separate from the sensing area prior to tissue piercing;
wherein said storage areas and sensing area are positioned to cause fluid to first flow to the enzyme area and then to the sensing area.

18. A method of body fluid sampling comprising:
moving a penetrating member conforming to a selectable velocity profile or motion waveform;
piercing a storage area having a sensing area;
piercing another storage area having an enzyme area separate from the sensing area prior to piercing;
causing fluid to first flow to the enzyme area and then to the sensing area.

19. The method of claim 18 further comprising storing said enzyme area in an inert environment different from an environment for the sensing area.

20. A device for body fluid sampling usable with a cartridge housing a plurality of penetrating members, the device comprising:
a housing;
a penetrating member driver coupled to said housing and for use with said cartridge;
a processor for controlling said penetrating member driver to move at least one of said penetrating members at velocities which conform with a selectable velocity profile;
a storage area having a sensing area;
another storage area having an enzyme area separate from the sensing area prior to piercing;
wherein said penetrating member pierces opens both storage areas upon member actuation and causes body fluid to first flow to the enzyme area and then to the sensing area.

* * * * *